US012589140B2

(12) United States Patent　　　　(10) Patent No.: US 12,589,140 B2
Mayadas et al.　　　　　　　　　　　　(45) Date of Patent: Mar. 31, 2026

(54) ANTIGEN-PRESENTING NEUTROPHIL-DERIVED DENDRITIC CELLS AND METHODS OF USE THEREOF

(71) Applicant: The Brigham and Women's Hospital, Inc., Boston, MA (US)

(72) Inventors: Tanya Mayadas, Jamaica Plain, MA (US); Vijaya Mysore, West Roxbury, MA (US); Xavier Cullere, Newton, MA (US); Jon C. Aster, Lexington, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1004 days.

(21) Appl. No.: 17/424,431

(22) PCT Filed: Jan. 22, 2020

(86) PCT No.: PCT/US2020/014642
　§ 371 (c)(1),
　(2) Date: Jul. 20, 2021

(87) PCT Pub. No.: WO2020/154424
　PCT Pub. Date: Jul. 30, 2020

(65) Prior Publication Data
　US 2022/0106566 A1　Apr. 7, 2022

Related U.S. Application Data

(60) Provisional application No. 62/795,498, filed on Jan. 22, 2019.

(51) Int. Cl.
　*A61K 39/00*　　(2006.01)
　*A61K 38/19*　　(2006.01)
　(Continued)

(52) U.S. Cl.
　CPC ........ *A61K 39/0005* (2013.01); *A61K 38/193* (2013.01); *A61K 40/19* (2025.01);
　(Continued)

(58) Field of Classification Search
　CPC .............. A61K 38/193; A61K 39/0005; A61K 39/4615; A61K 39/4622;
　(Continued)

(56) References Cited

U.S. PATENT DOCUMENTS 5,679,356 A * 10/1997 Bonnem ................ A61K 39/39
　　　　　　　　　　　　　　　　　　　424/278.1
2007/0014795 A1　1/2007 Dhodapkar et al.
　(Continued)

FOREIGN PATENT DOCUMENTS

JP　　2001061469 A　　3/2001
JP　　2004189724 A　　7/2004
　(Continued)

OTHER PUBLICATIONS

Silla, L.M.R., et al (1995) Potentiation of lysis of leukemia cells by a bispecific antibody to CD33 and CD16 (FcγRIII) expressed by human natural killer (NK) cells British Journal of Haematology 89; 712-718 (Year: 1995).*
　(Continued)

*Primary Examiner* — Joanne Hama
*Assistant Examiner* — Audrey L Buttice
(74) *Attorney, Agent, or Firm* — QUARLES & BRADY LLP

(57)　　　　　　　ABSTRACT

Methods and compositions for use in generating or promoting an immune response to cancer or an infection, comprising promoting differentiation of neutrophils into dendritic cells using a combination of GMCSF and (i) an immune complex comprising an antigen and an antibody comprising an Fc region that binds to FcγRIIA or FcγRIIIB, (ii) a
　(Continued)

conjugate comprising an antigen and an anti-FcγRIIIB antibody, or (iii) an anti-FcγRIIIB antibody.

14 Claims, 31 Drawing Sheets

Specification includes a Sequence Listing.

(51) Int. Cl.

| | |
|---|---|
| *A61K 40/19* | (2025.01) |
| *A61K 40/24* | (2025.01) |
| *A61K 40/42* | (2025.01) |
| *A61K 47/68* | (2017.01) |
| *A61P 35/00* | (2006.01) |
| *C07K 16/28* | (2006.01) |
| *C12N 5/0784* | (2010.01) |

(52) U.S. Cl.
CPC .......... *A61K 40/24* (2025.01); *A61K 40/4201* (2025.01); *A61K 40/421* (2025.01); *A61K 47/6849* (2017.08); *A61P 35/00* (2018.01); *C07K 16/283* (2013.01); *A61K 2039/505* (2013.01); *C12N 5/0639* (2013.01); *C12N 2501/22* (2013.01); *C12N 2501/998* (2013.01); *C12N 2506/11* (2013.01)

(58) Field of Classification Search
CPC .... A61K 39/464401; A61K 39/464411; A61K 39/39; A61K 47/6849; A61K 2039/505; A61K 2039/572; A61P 35/00; C07K 16/283; C07K 2317/75; C12N 5/0639; C12N 2501/22; C12N 2501/998; C12N 2506/11

See application file for complete search history.

(56) References Cited

U.S. PATENT DOCUMENTS

| | | | |
|---|---|---|---|
| 2012/0039916 A1 | 2/2012 | Zurawski et al. |
| 2013/0109073 A1 | 5/2013 | Chang et al. |
| 2015/0126398 A1 | 5/2015 | Takashima et al. |
| 2017/0137530 A1 | 5/2017 | Baehner et al. |
| 2017/0321189 A1 | 11/2017 | Karlsson-Parra et al. |
| 2018/0250336 A1 | 9/2018 | Eruslanov et al. |
| 2018/0318439 A1 | 11/2018 | Govindan et al. |

FOREIGN PATENT DOCUMENTS

| | | |
|---|---|---|
| JP | 2013535508 A | 9/2013 |
| JP | 2017212902 A | 12/2017 |
| WO | WO 2020/154424 | 7/2020 |

OTHER PUBLICATIONS

Mende, I., et al (2005) Highly efficient antigen targeting to M-DC8+ dendritic cells via FcγRIII/CD16-specific antibody conjugates International Immunology (17)5; 539-547 (Year: 2005).*

Matsushima, H., et al (2013) Neutrophil differentiation into a unique hybrid population exhibiting dual phenotype and functionality of neutrophils and dendritic cells Blood 121(10); 1677-1689 (Year: 2013).*

Vossebeld, P.J.M., et al (1997) The anti-FcγRIII Mab 3G8 induces neutrophil activation via a cooperative action of FcγRIIIb and FcγRIIa Int. J. Biochem. Cell Biol. 29(3); 465-473 (Year: 1997).*

Hanke, T., et al (1992) Construction of solid matrix-antibody-antigen complexes containing simian immunodeficiency virus p27 using tag-specific monoclonal antibody and tag-linked antigen Journal of general virology 73; 653-660 (Year: 1992).*

Krishna, U., et al (2014) GM-CSF modulates autoantibody production and skin blistering in experimental epidermolysis bullosa and acquisita J Immunol 192(2); 559-571 (Year: 2014).*

Zhao, W., et al (2018) Revisiting GM-CSF as an adjuvant for therapeutic vaccines Cellular & Molecular Immunology 15; 187-189 (Year: 2018).*

Abbas et al., "Functional diversity of helper T lymphocytes," Nature, Oct. 1996, 383(6603):787-93.

Alvarez et al., "Mechanisms and consequences of dendritic cell migration," Immunity, Sep. 19, 2008, 29(3):325-42.

Blander, "Regulation of the cell biology of antigen cross-presentation," Annual Review of Immunology, Apr. 26, 2018, 36:717, 41 pages Bournazos et al., "Fcγ receptor function and the design of vaccination strategies," Immunity, Aug. 15, 2017, 47(2):224-33

Bruggeman et al., "Enhanced effector functions due to antibody defucosylation depend on the effector cell Fcγ receptor profile," The Journal of Immunology, Jul. 1, 2017, 199(1):204-11

Bruhns et al., "Specificity and affinity of human Fcγ receptors and their polymorphic variants for human IgG subclasses," Blood, The Journal of the American Society of Hematology, Apr. 16, 2009, 13(16):3716-25.

Burleson et al., "Evaluation of cell-mediated immune function using the cytotoxic T-Lymphocyte assay," Immunotoxicity Testing, Jun. 2018, 199-208

Carreno et al., "A dendritic cell vaccine increases the breadth and diversity of melanoma neoantigen-specific T cells," Science, May 15, 2015, 348(6236):803-8.

Cassidy et al., "Synthesis of viral proteins in polymorphonuclear leukocytes infected with influenza A virus," Journal of Clinical Microbiology, Jul. 1988, 26(7):1267-70.

Chen et al., "Endocytosis of soluble immune complexes leads to their clearance by FcγRIIIB but induces neutrophil extracellular traps via FcγRIIA in vivo," Blood, The Journal of the American of Hematology, Nov. 22, 2012, 120(22):4421-31.

Derer et al., "Increasing FcγRIIa affinity of an FcγRIII-optimized anti-EGFR antibody restores neutrophil-mediated cytotoxicity." Mabs, Mar. 1, 2014, 6(2):409-21.

Derer et al., "Ratios of FcγRIIa and FcγRIII Binding Affinities Govern the Efficacy of PMN-Mediated Cytotoxicity-Implications for Fc-Engineering Approaches of Therapeutic Antibodies," Blood, Nov. 15, 2013, 122(21):3466, 2 pages.

Ferrara et al., "Unique carbohydrate-carbohydrate interactions are required for high affinity binding between FcγRIII and antibodies lacking core fucose," Proceedings of the National Academy of Sciences, Aug. 2, 2011, 108(31):12669-74.

Fites et al., "An unappreciated role for neutrophil-DC hybrids in immunity to invasive fungal infections," PLoS Pathogens, May 21, 2018, 14(5):e1007073, 32 pages Gillis et al., "Contribution of human FcγRs to disease with evidence from human polymorphisms and transgenic animal studies," Frontiers in Immunology, May 30, 2014, 5:254, 14 pages.

Guilliams et al., "The function of Fcγ receptors in dendritic cells and macrophages," Nature Reviews Immunology, Feb. 2014, 14(2):94-108.

Hasenberg et al., "Catchup: a mouse mode for imaging-based tracking and modulation of neutrophil granulocytes," Nature Methods, May 2015, 12(5):445-52.

Hu et al., "Towards personalized, tumour-specific, therapeutic vaccines for cancer," Nature Reviews Immunology, Mar. 2018, 18(3):168-82.

Hufford et al., Influenza-infected neutrophils within the infected lungs act as antigen presenting cells for anti-viral CD8+ T cells, PLoS One, Oct. 2012, 7(10):e46581, 10 pages.

Hutchison et al., "Identifying neoantigens for use in immunotherapy," Mammalian Genome, Dec. 2018, 29(11):714-30.

Ivan et al., "Human Fc receptors: critical targets in the treatment of autoimmune diseases and transplant rejections," Human Immunology, Jul. 1, 2006, 67(7):479-91.

Jefferis, Glycosylation as a strategy to improve antibody-based therapeutics. Nature Reviews Drug Discovery, Mar. 2009, 8(3):226-34.

(56)          References Cited

OTHER PUBLICATIONS

Larochelle et al., "Epstein-Barr virus infects and induces apoptosis in human neutrophils," Blood, The Journal of the American Society of Hematology, Jul. 1, 1998, 92(1):291-9.

Lehmann et al., "Direct delivery of antigens to dendritic cells via antibodies specific for endocytic receptors as a promising strategy for future therapies," Vaccines, Jun. 2016, 4(2):8, 32 pages.

Lindsley et al., "The biology and clinical impact of genetic lesions in myeloid malignancies," Blood, The Journal of the American Society of Hematology, Nov. 28, 2013, 122(23):3741-8

Linette et al., "Neoantigen vaccines pass the immunogenicity test," Trends in Molecular Medicine, Oct. 1, 2017, 23(10):869-71.

Mackensen et al, "Homing of intravenously and intralymphatically injected human dendritic cells generated in vitro from CD34+ hematopoietic progenitor cells," Cancer Immunology, Immunotherapy, Jun. 1, 1999, 48(2-3):118-22.

Macri et al., "Targeting dendritic cells: a promising strategy to improve vaccine effectiveness," Clinical & Translational Immunology, Mar. 2016, 5(3):e66, 8 pages.

Mayadas et al., "The multifaceted functions of neutrophils," Annual Review of Pathology: Mechanisms of Disease, Jan. 2014, 9:181, 42 pages.

Mizushima et al., "Structural basis for improved efficacy of therapeutic antibodies on defucosylation of their Fc glycans," Genes to Cells, Nov. 2011, 16(11):1071-80.

Nimmerjahn et al., Fcγ receptors as regulators of immune responses. Nature Reviews Immunology, Jan. 2008, 8(1):34-47.

Ott et al., "An immunogenic personal neoantigen vaccine for patients with melanoma," Nature, Jul. 2017, 547(7662):217-21.

Palucka et al., "Dendritic-cell-based therapeutic cancer vaccines," Immunity, Jul. 2013, 39(1):38-48.

PCT International Preliminary Report on Patentability in International Appln. No. PCT/US2020/014642, dated Aug. 5, 2021, 10 pages.

PCT International Search Report and Written Opinion in International Appln. No. PCT/US2020/014642, dated Apr. 2, 2020, 11 pages.

Peipp et al., "Antibody fucosylation differentially impacts cytotoxicity mediated by NK and PMN effector cells," Blood, The Journal of the American Society of Hematology, Sep. 15, 2008, 112(6):2390-9.

Perussia et al., "Antibody 3G8, specific for the human neutrophil Fc receptor, reacts with natural killer cells," The Journal of Immunology, Mar. 1, 1984, 132(3):1410-5.

Phillips et al., "Clinical tolerogenic dendritic cells: exploring therapeutic impact on human autoimmune disease," Frontiers in Immunology, Oct. 12, 2017, 8:1279, 9 pages.

Radford et al., "Dendritic cells and cancer immunotherapy," Current Opinion in Immunology, Apr. 2014. 27:26-32.

Rafiq et al., "Immune complex-mediated antigen presentation induces tumor immunity," The Journal of Clinical Investigation, Jul. 2002, 110(1):71-9.

Regnault et al., "Fcγ receptor-mediated induction of dendritic cell maturation and major histocompatibility complex class I-restricted antigen presentation after immune complex internalization," Journal of Experimental Medicine, Jan. 18, 1999, 189(2):371-80

Renkvist et al., "A listing of human tumor antigens recognized by T cells," Cancer Immunology Immunotherapy, Mar. 2001, 50(1):3-15.

Rogers et al., "IgG Fc receptor III homologues in nonhuman primate species: genetic characterization and ligand interactions," The Journal of Immunology, Sep. 15, 2006, 177(6):3848-56.

Rosenblatt et al., "Individualized vaccination of AML patients in remission is associated with induction of antileukemia immunity and prolonged remissions," Science Translational Medicine, Dec. 2016, 8(368):368ra171, 8 pages.

Rungelrath et al., "Neutrophils in innate immunity and systems biology-level approaches," Wiley Interdisciplinary Reviews: Systems Biology and Medicine, Jan. 2020, 12(1):e1458.

Saez-Lopez et al., "Immediate-early antigen expression and modulation of apoptosis after in vitro infection of polymorphonuclear leukocytes by human cytomegalovirus," Microbes and Infection, Jul. 2005, 7(9-10):1139-49

Schuurhuis et al., "Immune complex-loaded dendritic cells are superior to soluble immune complexes as antitumor vaccine," The Journal of Immunology, Apr. 2006, 176(8):4573-80.

Shi et al., "IL-15/IL-15Rα/CD80-expressing AML cell vaccines eradicate minimal residual disease in leukemic mice," Blood Advances, Nov. 2018, 2(22):3177-92.

Su et al., "Expression profile of FcγRIIb on leukocytes and its dysregulation in systemie lupus erythematosus," The Journal of Immunology, Mar. 2007, 178(5):3272-80

Subedi et al., "The immunoglobulin Gl N-glycan composition affects binding to each low affinity Fc γ receptor," Mabs, Nov. 2016, 8(8):1512-24.

Takashima et al., "Neutrophil plasticity: acquisition of phenotype and functionality of antigen-presenting cell," Journal of Leukocyte Biology, Oct. 2015, 98(4):489-96.

Tanyi et al., "Personalized cancer vaccine effectively mobilizes antitumor T cell immunity in ovarian cancer," Science Translational Medicine, Apr. 2018, 10(436), 15 pages.

Teku et al., "Pan-cancer analysis of neoepitopes," Scientific Reports, Aug. 2018, 8(1), 10 pages.

Treffers et al., "Neutrophils in cancer," Immunological Reviews, Sep. 2016, 273(1):312-28.

Tsokos et al., "New insights into the immunopathogenesis of systemic lupus erythematosus," Nature Reviews Rheumatology, Dec. 2016, 12(12):716-30.

Tsuboi et al., "Human neutrophil Fcγ receptors initiate and play specialized nonredundant roles in antibody-mediated inflammatory diseases," Immunity, Jun. 2008, 28(6):833-46.

Unkeless et al., "Function of human FcγRIIA and FcγRIIIB," Seminars in Immunology, Feb. 1995, 7(1), 37-44.

Van Acker et al., "Dendritic cell-based immunotherapy of acute myeloid leukemia," Journal of Clinical Medicine, May 2019, 8(5):579, 14 pages.

Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, Aug. 1999, 190(3):355-66.

Van Willigen et al., "Dendritic cell cancer therapy: vaccinating the right patient at the right time," Frontiers in Immunology, Oct. 2018, 9:2265, 13 pages Vieira et al., "The half-lives of serum immunoglobulins in adult mice," European Journal of Immunology, Feb. 1988, 18(2):313-6

Vigneron et al., "Database of T cell-defined human tumor antigens: the 2013 update," Cancer Immunity Archive, Jan. 2013, 13(3), 6 pages Villadangos et al., "Intrinsic and cooperative antigen-presenting functions of dendritic-cell subsets in vivo," Nature Reviews Immunology, Jul. 2007, 7(7):543-55

Wang et al., "Toll-like receptor-mediated activation of neutrophils by influenza A virus," Blood, The Journal of the American Society of Hematology, Sep. 2008, 112(5):2028-34

Webster et al., "Acute myeloid leukemia in the elderly: therapeutic options and choice," Leukemia & Lymphoma, Feb. 2018, 59(2):274-87

Wen et al., "Immunoregulatory functions of immune complexes in vaccine and therapy," EMBO Molecular Medicine, Oct. 2016, 8(10):1120-33.

Yamamoto et al., "Role of adaptor TRIF in the MyD88-independent toll-like receptor signaling pathway," Science, Aug. 2003, 301(5633):640-3.

Yan et al., "Recent progress in GM-CSF-based cancer immunotherapy," Immunotherapy, Mar. 2017, 9(4):347-60.

Zhang et al., "Fc engineering approaches to enhance the agonism and effector functions of an anti-OX40 antibody," Journal of Biological Chemistry, Dec. 2016, 291(53):27134-46

(56)           References Cited

OTHER PUBLICATIONS

Zhao et al., "Neutrophils may be a vehicle for viral replication and dissemination in human H5N1 avian influenza," Clinical Infectious Diseases, Dec. 2008, 47(12):1575-8.

JP Office Action in Japanese Appln. No. 2021-542444, mailed on Dec. 19, 2023, 12 pages (with English translation).

\* cited by examiner

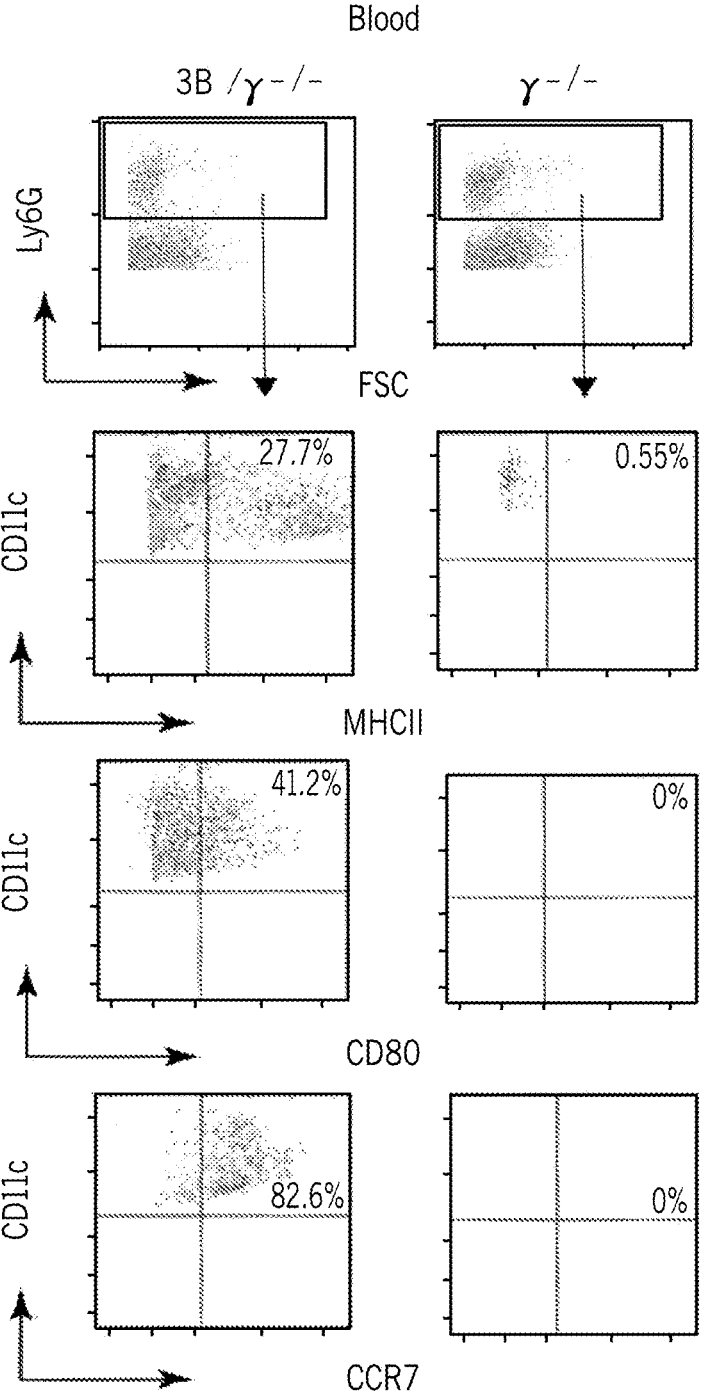
FIG. 4A, continued

CD8

|  | FVD | CD3/CD8 | CD62L$^{lo}$/CD44$^{hi}$ | CD62L$^{lo}$/CD44$^{hi}$/Tetr$^+$ | CD62$^{lo}$/CD44$^{hi}$/PD1$^+$ |
|---|---|---|---|---|---|
| FITC-OVA | 75.74±2.26 | 13.83±0.45 | 28.62±6.72 | 0.61±0.07 | 0.62±0.15 |
| 2A3B/γ$^{-/-}$ + 3G8-OVA | 81.78±1.08 | 12.65±0.80 | 28.14±5.88 | 3.28±1.11** | 1.23±0.31 |
| γ$^{-/-}$ + 3G8-OVA | 77.08±1.81 | 12.91±0.54 | 27.82±5.61 | 0.42±0.10 | 0.79±0.20 |

CD4

|  | FVD | CD3/CD4 | CD4/CD25 | CD4/CD69 | CD4/Foxp3$^+$ | CD4/Ki67$^+$ | CD4/Tbet$^+$ |
|---|---|---|---|---|---|---|---|
| FITC-OVA | 80.94±4.33 | 17.28±1.08 | 0.48±0.11 | 0.26±0.06 | 6.31±2.64 | 13.39±1.87 | 5.97±0.69 |
| 2A3B/γ$^{-/-}$ + 3G8-OVA | 85.31±2.34 | 19.66±0.42 | 1.30±0.19 | 0.34±0.1 | 8.19±2.93 | 18.56±1.4 | 5.10±0.49 |
| γ$^{-/-}$ + 3G8-OVA | 81.52±3.73 | 18.20±1.28 | 1.11±0.17 | 0.33±0.09 | 4.56±1.38 | 16.71±1.57 | 4.17±1.07 |

Ratio

|  | CD8$^+$/Treg$^+$ | CD8Tet$^+$/Treg$^+$ | CD4 Teff$^+$/Treg$^+$ |
|---|---|---|---|
| FITC-OVA | 6.69±1.63 | 0.32±0.09 | 0.83±0.43 |
| 2A3B/γ$^{-/-}$ + 3G8-OVA | 5.02±1.68 | 0.92±0.30 | 0.52±0.18 |
| γ$^{-/-}$ + 3G8-OVA | 9.01±3.06 | 0.30±0.11 | 0.68±0.27 |

FIG. 7E

ANTIGEN-PRESENTING NEUTROPHIL-DERIVED DENDRITIC CELLS AND METHODS OF USE THEREOF

CLAIM OF PRIORITY

This application is a § 371 National Stage Application of PCT/US2020/014642, filed Jan. 22, 2020, which claims the benefit of U.S. Provisional Patent Application Ser. No. 62/795,498, filed on Jan. 22, 2019. The entire contents of the foregoing are hereby incorporated by reference.

FEDERALLY SPONSORED RESEARCH OR DEVELOPMENT

This invention was made with Government support under Grant No. HL065095 awarded by the National Institutes of Health. The Government has certain rights in the invention.

SEQUENCE LISTING

This application is being filed electronically and includes an electronically submitted Sequence Listing in .txt format. The .txt file contains a sequence listing entitled "12931901059_ST25.txt" created on Dec. 17, 2025, and is 659 bytes in size. The Sequence Listing contained in this .txt file is part of the specification and is hereby incorporated by reference herein in its entirety.

TECHNICAL FIELD

Described herein are methods and compositions for use in generating or promoting an immune response to cancer or an infection, comprising promoting differentiation of neutrophils into dendritic cells using a combination of GMCSF and (i) an immune complex comprising an antigen and an antibody to the antigen comprising an Fc region that binds to FcγRIIA or FcγRIIIB, (ii) a conjugate comprising an antigen and an anti-FcγRIIIB antibody, or (iii) an anti-FcγRIIIB antibody.

BACKGROUND

Dendritic cells (DC) are essential for presenting antigen to naive T cells in lymphoid organs. DC uptake of extracellular proteins leads to presentation of peptide on MHCII while peptides generated from cytosolic proteins are loaded on MHCI to activate naïve CD4$^+$ helper and CD8$^+$ cytotoxic T cells, respectively. DCs also cross-present antigen, wherein extracellular antigens taken into vesicles gain access to the cytosol and MHCI pathway to prime CD8$^+$ T cells. This property is thought to be exclusive to DCs and exploited for cell-based immunotherapy to treat cancer as well as infections[1, 2, 3].

SUMMARY

The present invention is based, at least in part, on the discovery that FcγR mediated antigen intake by neutrophils results in their differentiation into migratory dendritic-like cells that activate naïve CD4+ and CD8+ T cells.

Neutrophils, specialized for microbe elimination, can acquire functions of antigen presenting cells following cytokine stimulation. Here we show that the uptake of antigen-containing immune-complexes converts neutrophils into cells with dendritic cell-like features (neutrophil-derived DCs, NDDC) that activate naïve CD4+ and CD8+ T cells and, in vivo, induce a delayed-type-hypersensitivity response and tumor immunity. Neutrophils from humanized mice show that both FcγRIIIB and FcγRIIA support the generation of NDDCs. Intravenously delivered antigen-conjugated antibody against neutrophil FcγRIIIB in mice generates NDDCs in blood and spleen, supports CD8 T cell proliferation and cytolytic functions and in the presence of GM-CSF reduces tumor growth. Likewise, antigen-conjugated anti-FcγRIIIB converts human neutrophils into NDDCs. Thus, FcγRIIIB-mediated antigen delivery can be exploited to elicit effective acquired immunity to tumors and pathogens.

Thus provided herein are in vitro methods for generating a population of dendritic cells (DCs). The methods comprise providing a population of neutrophils comprising neutrophils that express one or both of FcγRIIA and/or FcγRIIIB; contacting the neutrophils in culture with Granulocyte-macrophage colony-stimulating factor (GM-CSF) and an immune complex (IC) comprising an antigen and an antibody, wherein the antibody comprises an antigen binding portion that binds to the antigen and an Fc region that binds to FcγRIIA and/or FcγRIIIB; and maintaining the population of neutrophils in culture in the presence of GM-CSF and IC under conditions and for a time sufficient for the neutrophils to differentiate into DCs.

In some embodiments, the antigen comprises a tag, and an antibody that binds to the tag portion of the antigen.

In some embodiments, the antigen is a tumor antigen. These cells can be used, e.g., in a method of treating cancer. Also provided herein are methods of treating a subject who has cancer, comprising administering to the subject an effective amount of cells generated by this method.

In some embodiments, the antigen is from a pathogen. These cells can be used, e.g., in a method of treating an infection wherein the antigen is from the pathogen with which the subject is infected. Also provided herein are methods of treating a subject who is infected with a pathogen, comprising administering to the subject an effective amount of these cells generated, wherein the antigen is from the pathogen with which the subject is infected.

Also provided herein are conjugates (e.g., fusion protein or chemical conjugate) comprising (i) an antigen, and (ii) an antibody comprising an antigen-binding domain that binds to FcγRIII. In some embodiments, the antigen is a tumor antigen or an antigen from a pathogen.

Further, provided herein are in vitro methods for generating a population of dendritic cells (DCs). The methods comprise providing a population of neutrophils comprising neutrophils that express one or both of FcγRIIA and/or FcγRIIIB; contacting the population of neutrophils in culture with the conjugates described herein, and optionally Granulocyte-macrophage colony-stimulating factor (GM-CSF), and maintaining the population of neutrophils in culture in the presence of the conjugate and GM-CSF under conditions and for a time sufficient for the neutrophils to differentiate into DCs.

In some embodiments, the antigen is a tumor antigen. These DCs can be used, e.g., in a method of treating cancer. Also provided are methods of treating a subject who has cancer, comprising administering to the subject an effective amount of DCs generated by these methods.

In some embodiments, the antigen is from a pathogen. These DCs can be used, e.g., in a method of treating an infection wherein the antigen is from the pathogen with which the subject is infected. Also provided are methods of treating a subject who is infected with a pathogen, the administering to the subject an effective amount of these DCs, wherein the antigen is from the pathogen with which the subject is infected.

In addition, provided herein are methods for treating a subject, comprising administering to the subject an effective amount of a conjugate as described herein comprising (i) an antigen, and (ii) an antibody comprising an antigen-binding domain that binds to FcγRIII, and optionally Granulocyte-macrophage colony-stimulating factor (GM-CSF). In some embodiments, the subject has cancer, and the antigen is a tumor antigen. In some embodiments, the subject has an infection with a pathogen, and the antigen is from the pathogen.

Also provided herein are methods for generating a population of dendritic cells (DCs) comprising providing a population of neutrophils that express one or both of FcγRIIA and/or FcγRIIIB, e.g., from a subject; contacting the neutrophils in culture with an antibody that comprises an antigen binding portion that binds to the antigen and an Fc region that binds to FcγRIIA and/or FcγRIIIB; and maintaining the population of neutrophils in culture under conditions and for a time sufficient for the neutrophils to differentiate into DCs.

In some embodiments, the population of neutrophils is maintained in the presence of GM-CSF and/or IC.

Also provided herein are populations of dendritic cells generated by a method described herein, e.g., for use in a method of treating a subject, preferably a subject from whom the population of neutrophils was obtained.

In some embodiments, the population of neutrophils comprising neutrophils that express one or both of FcγRIIA and/or FcγRIIIB was obtained from a subject, and the method further comprises administering the differentiated dendritic cells to the subject from whom the population of neutrophils was obtained.

In some embodiments, the subject has a myeloid neoplasm or an infection e.g., a bacterial, fungal, or viral infection.

Also provided herein are methods of treating a subject who has a myeloid neoplasm or an infection, e.g., a bacterial, fungal, or viral infection. The methods include administering to the subject an effective amount of an antibody comprising an antigen-binding domain that binds to FcγRIII In some embodiments, the subject has a myeloid neoplasm selected from the group consisting of acute myeloid leukemia (AML), myelodysplastic syndrome (MDS), or myeloproliferative neoplasms (MPN).

"The term "antigen" comprises any structure which is capable of inducing an immune response in an organism either by itself or when coupled to a suitable carrier molecule or cell. Therefore, antigens according to the present invention include low molecular compounds which serve as haptens as well as whole cells such as tumor cells as well as the parts thereof such as polypeptides, oligopeptides derived therefrom, lipids such as glycolipids, polysaccharides and nucleic acids.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGs., and from the claims.

DESCRIPTION OF DRAWINGS

FIGS. 5A-G. A) Gating strategy to assess purity of murine neutrophils isolated from bone marrow of mice. Cells were stained with CD11b, Ly6G, MHCII, CD11c and CD115 and evaluated. B) Gating strategy for the expression of DC markers CD11c and MHCII, co-stimulatory molecules CD80 and CD86 and migratory receptor CCR7 on NDDCs generated from neutrophils treated with model ICs or their individual components. Representative strategy for OVA-IC generated NDDC is shown Single cells were gated using FSC-H and FSC-A. All the live cells that are negative for lineage markers (CD3, NK1.1, CD19) and negative for fixable viability dye were further gated for CD11c, MHCII and Ly6G. Positive cells were then checked for expression of CD80, CD86 and CCR7. C) NDDC were generated using the indicated model ICs or individual components. After 3 days, cells were analyzed for XCR1, CD8a and CD103 (DC1 subsets) or Siglec-H (plasmacytoid DC marker) on CD11c$^+$ MHCII$^+$ Ly6G$^+$ cells. Data is a comparison between mean±s.e.m of OVA versus OVA-IC or anti-OVA for all model ICs based on one way ANOVA and Dunnett's multiple comparison test. D) Gating strategy for the expression of DC markers, co-stimulatory molecules and CCR7 on neutrophils cultured with normal sera (NHS), SLE patient sera or ICs generated with RNP and IgG from normal or anti-RNP positive SLE sera. Representative strategy for SLE-sera generated NDDC is shown. E) Subset analysis of XCR1, CD8a and CD103 (DC1 subsets) on NDDC generated from NHS, SLE patient sera or ICs generated with RNP and IgG from normal or anti-RNP positive SLE sera. F) Gating strategy for blood samples from human controls and SLE patients analyzed for CD80, CCR7 and DC subset markers. G) NDDCs derived from WT and MyD88$^{-/-}$ TRIF$^{-/-}$ were analyzed for CD11c, MHCII and Ly6G expression (top panel). The positive cells were further evaluated for CD86, CD80 (middle panel) and CCR7 (bottom panel). The student t-test for unpaired comparisons with Dunn-Bonferoni was used **P<0.005.

Figure 6:
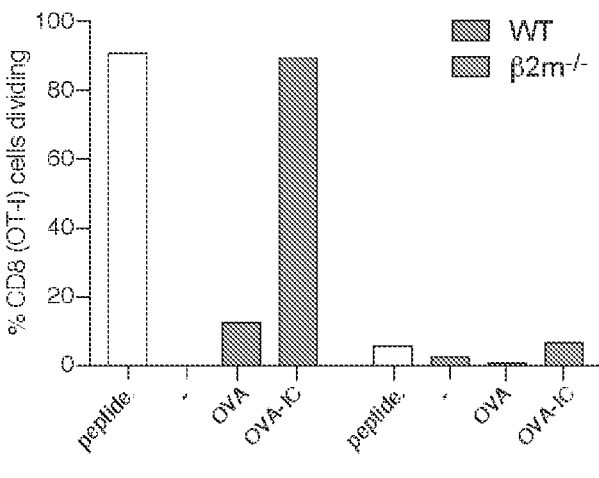
Figure 6:
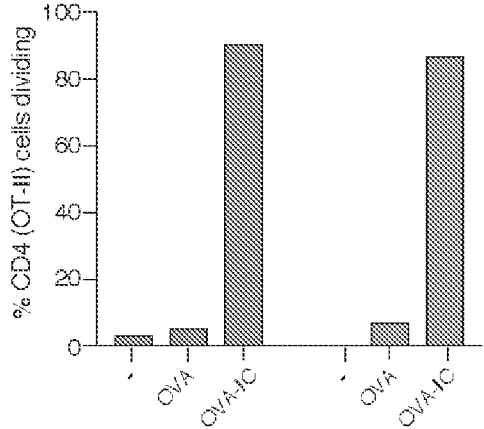

FIG. 6. Neutrophils isolated from WT and β2 microglobulin deficient (−/−) mice were treated with GM-CSF alone (−), OVA or OVA-ICs and cultured for 3 days. Adherent NDDCs were co-cultured with CFSE labeled OT-I T cells or OT-II T cells. As a positive control for OT-I proliferation GM-CSF generated NDDC were pulsed with the OVA peptide SIINFEKL (SEQ ID NO: 1). Percent proliferation was measured by CFSE dye dilution.

FIGS. 7A-E. A) Anti-FcγRIIIB 3G8 antibody conjugated to FITC-OVA (3G8-OVA) was given i.v. to mice. After 3.5 hrs blood was isolated and internalization of FITC-OVA, FcγRIIIB (CD16) and FcγRIIA (CD32) was assessed. Anti-CD16 antibody REA 589 binds to an epitope distinct from 3G8. Gating strategy of FITC-OVA, FcγRIIIB and FcγRIIA is shown. B) Gating strategy to determine basal level of FcγRIIIB and FcγRIIA expression on CD115$^+$ and Ly6C$^{hi}$ cells in humanized transgenic mice expressing FcγRIIIB+ FcγRIIA. Mean±s.e.m. for FcγRIIIB and FcγRIIA are given for CD115$^+$Ly6C$^{hi}$ population (n=4). C) Gating strategy to assess the presence of 3G8-OVA positive events in CD11c$^+$ MHCII$^+$ NDDCs in spleen of 2A3B/γ$^{-/-}$ and γ$^{-/-}$ mice 72 hrs after 3G8-OVA conjugate i.v. injection. D) Regression analysis was used to compare slope curve co-efficients (tumor growth rate) between the different groups. A Prism regression analysis was used and tested for whether slopes and intercepts differ. Overall comparison was done using a one-way ANOVA and Dunnett's multiple comparison. Trendlines for tumor volume of all groups were created using Excel and are shown. Tumor growth in 2A3B/γ$^{-/-}$+ 3G8-OVA was compared to WT+FITC-OVA, γ$^{-/-}$+3G8-OVA and 3B/γ$^{-/-}$, P<0.005. E) Table of T cell subset analysis of spleen harvested from mice injected with B16F10-OVA. Spleens were analyzed for OVA-peptide specific effector CD8 T cells (CD62$^{lo}$ CD44$^{hi}$) using MHCI-tetramers and markers for CD8 effector, CD4 and Treg cells. Results for T cell activation markers (CD25; CD69) proliferation marker (Ki67), transcriptional regulators (t-bet) and PD1 are also shown. P<0.05 in 2A3B/γ$^{-/-}$+3G8-OVA compared to other groups.

Figure 8:
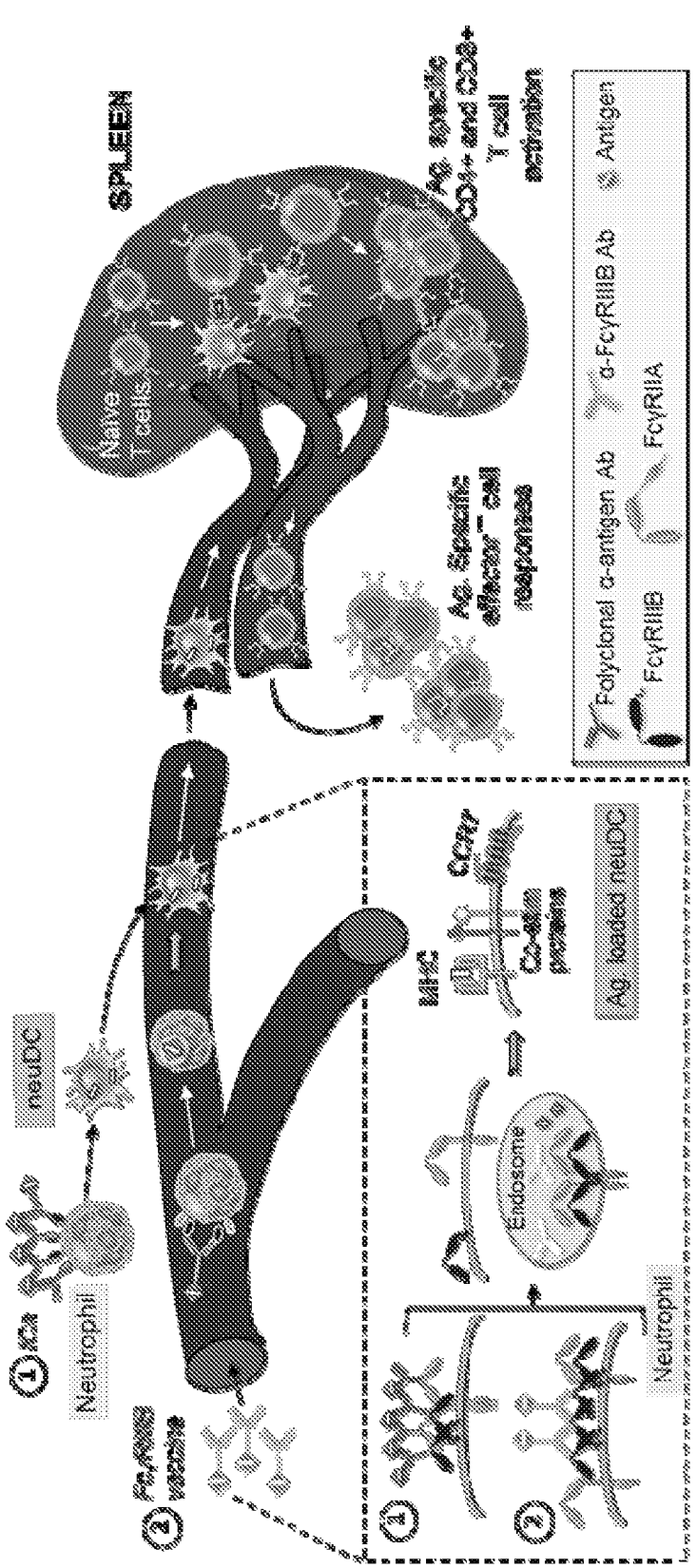

FIG. 8. FcγR mediated antigen-antibody uptake leads to neutrophil differentiation into antigen loaded dendritic cells that promote antigen specific T cell responses. Neutrophils incubated ex vivo with antigen-antibody immune complexes (ICs) enhances antigen uptake (1). Anti-FcγRIIIB-antigen (protein or peptide) conjugate (FcγRIIIB vaccine) injected i.v selectively binds to and triggers antigen internalization by neutrophils (2). FcγR engagement by method 1) or 2) transmits signals that promote neutrophil differentiation into dendritic cells and the efficient loading of antigen on MHCI and MHCII. NDDCs injected i.v. (1) or generated in vivo (2) migrate to the spleen. Here they present antigen to naive CD4+ and CD8+ T cells to generate antigen specific effector T cells that migrate out of the spleen to promote T cell helper and cytolytic responses, respectively.

FIGS. 9A-D. A) Schematic illustration of a NDDC vaccine, comprising an anti-FcγRIIIB antibody conjugated to a tumor antigen. B) Schematic illustration of a method using only anti-FcγRIIIB antibody (without an exogenous antigen) to target a neutrophil. C) Quantitation of the ELISPOT assay, which detected IFN generation by activated T cells, for one experiment is shown. This experiment is one representative of two experiments for an independent Normal donor and Patient 1 (diagnosed with acute myeloid leukemia) and Patient 2 (diagnosed with myeloid dysplastic syndrome). D) Representative images are shown for indicated samples that were incubated with Isotype control or with Vaccine.

DETAILED DESCRIPTION

In humans, 60-70% of circulating blood leukocytes are neutrophils, which destroy pathogens and are considered end-differentiated immune effector cells with a limited life span[4]. However, neutrophils cultured with the survival factor GM-CSF and cytokines can acquire DC phenotypic markers and functional characteristics[5] and have been detected in inflammatory lesions in mice and human patients[5, 6]. The potency of neutrophil-derived DCs in effector immunity, the identification of molecular pathways that can potentially drive neutrophil-derived DCs to migrate and cross-present, and strategies for possibly harnessing these cells for therapeutic gain remain largely unexplored.

Low affinity FcγRs present on myeloid cells bind antigen-antibody immune-complexes (IC) to mediate several immunological functions[7, 8]. In mice, FcγRIII and FcγRIV require the immunoreceptor tyrosine-based activation motif (ITAM) containing γ-chain for cell surface expression and signaling and mice with γ-chain deficiency (γ−/−) are protected from tissue injury in several autoimmune disease models. However, the repertoire of FcγRs in mice and non-human primates differs from humans[7, 8]. Humans express the low affinity ITAM-containing single polypeptide FcγRIIA on neutrophils, monocytes, eosinophils, DCs and platelets while the glycophosphatidylinositol (GPI)-linked FcγRIIIB is almost exclusively expressed on neutrophils. The γ-chain associated FcγRIIIA is expressed on natural killer cells and monocytes/macrophages[9]. FcγRIIA promotes neutrophil cytotoxic functions[10] and on DCs, enhances maturation and cross-presentation[11] as does its murine counterparts[12]. Transgenic expression of FcγRIIA in mice increases susceptibility to autoimmune mediated injury, can drive an anti-tumor vaccine response[11, 12] and promotes anaphylaxis[9]. Much less is known about FcγRIIIB function. It promotes some neutrophil functions in collaboration with FcγRIIA[10] and can alone support IC-induced neutrophil accumulation[13]. In addition, FcγRIIIB, like FcγRIIA, can endocytose ICs and support uptake of ICs deposited within blood vessel walls[14]. FcγRIIB is an inhibitory receptor conserved in humans and mice that is primarily expressed on B cells, macrophages and DCs[8]. It is also detected on neutrophils but primarily in individuals with the infrequent FcγRIIB.4 promoter haplotype[15].

Figure 4A:
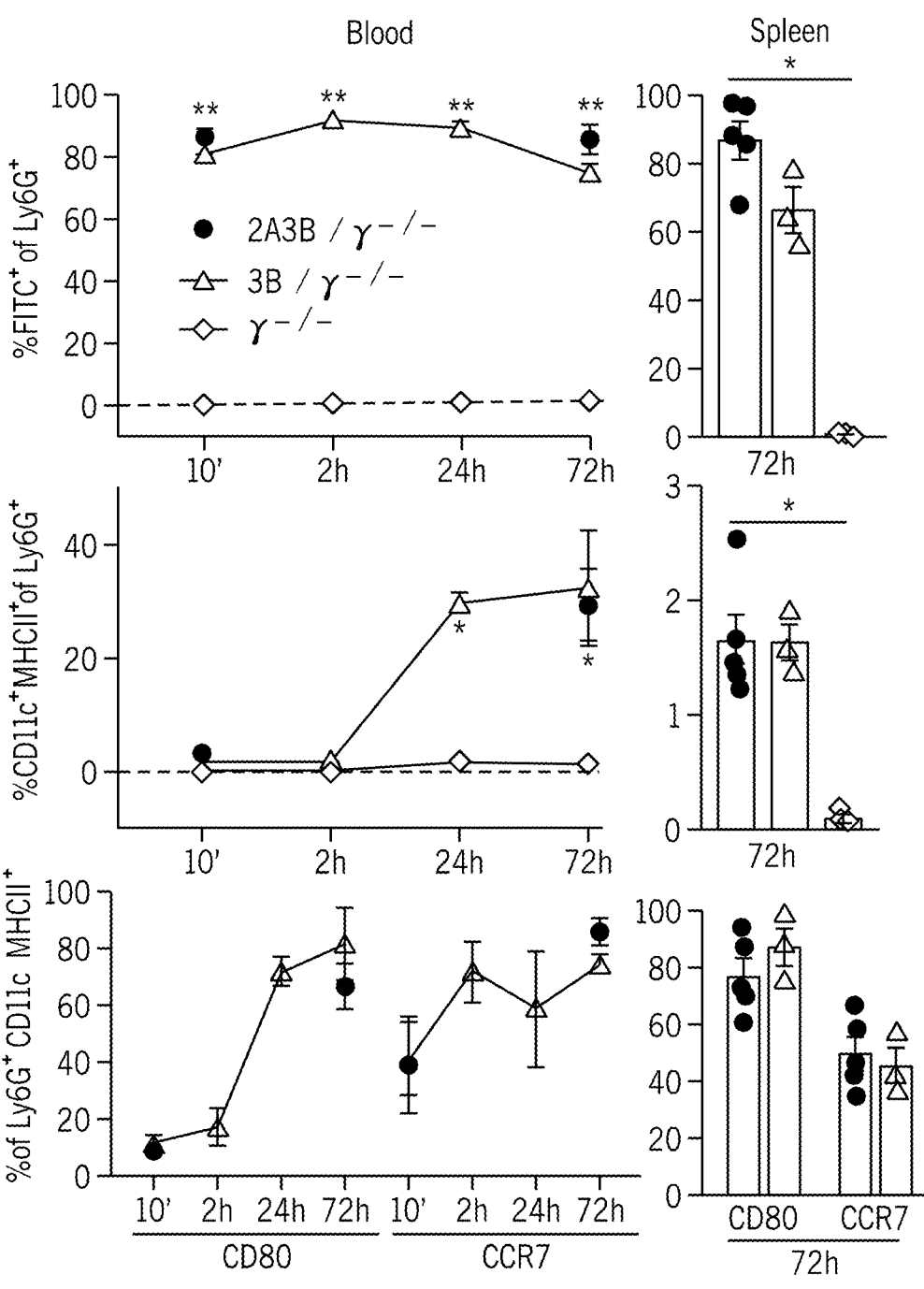
FIGS. 4A-G: Engagement of FcγRIIIB on blood neutrophils with antigen conjugated to antibody generates immunogenic DCs. Wild-type, γ$^{-/-}$, FcγRIIA(2A)/γ$^{-/-}$, FcγRIIIB (3B)/γ$^{-/-}$ and FcγRIIIB+FcγRIIA (2A3B)/γ$^{-/-}$ mice were used A) Anti-FcγRIIIB 3G8 antibody conjugated to FITC-OVA (3G8-OVA) was given i.v. to mice and FITC-OVA uptake (top panel) and neutrophil and DC markers (middle and bottom panel) were assessed in the blood and spleen at indicated times. Representative FACs profiles in blood are shown. One way ANOVA was performed to compare the mean±s.e.m. between γ$^{-/-}$ and 3B/γ$^{-/-}$ or 2A3B/γ$^{-/-}$ mice, P<0.005. B) Mice were given an i.v. injection of 3G8-OVA at day –3 and CFSE labeled OT-I CD8 T cells at day 0. At day 3, spleens were harvested and CD8 proliferation was assessed by CFSE dilution. Representative histograms of CD8 dividing cells (bar) in spleen and starting CD8 population (Con, light grey) are shown. ANOVA and Dunnett's correction was used to determine the significance between γ$^{-/-}$ and 2A3B/γ$^{-/-}$ or 3B/γ$^{-/-}$ mice, P<0.005. C) Mice were given an i.v. injection at day –10 of 3G8-OVA, and at day 0, OVA-peptide-pulsed and unpulsed target wild-type splenocytes labeled with high and low CFSE, respectively. The spleen was harvested 16 hrs later and the % of target cells killed evaluated. Mean±s.e.m. was evaluated and compared for statistical significance using ANOVA and Dunnett's correction. WT were compared to 2A3B/γ$^{-/-}$, 3B/γ$^{-/-}$, 2A/γ$^{-/-}$ and γ$^{-/-}$. P<0.005. D-F) Mice were given GM-CSF i.p. injections daily from day –10 to day –5 and an i.v. injection of 3G8-OVA or FITC-OVA at day –10. B16F10-OVA cells were implanted subcutaneously at day 0. D) Tumor growth was assessed. Number of mice per group is in parenthesis, scale bar=5 μmm and statistical analysis of tumor growth rate was described in FIG. 7. p<0.005 between 2A3B/γ$^{-/-}$+3G8-OVA and other groups. E) At harvest, spleens were analyzed for OVA-peptide specific effector CD8 T cells (CD62$^{lo}$ CD44$^{hi}$) using MHCI-tetramers, CD4 and Treg cells. One-way ANOVA with Dunnett's multiple comparison was used for significance in 2A3B/γ$^{-/-}$ versus γ$^{-/-}$ and WT. *P<0.05. F) Human whole blood pretreated with GM-CSF was incubated with 3G8-OVA or FITC-isotype control and % FITC positive neutrophils were determined at indicated times. FcγRIIIB internalization was assessed using anti-FcγRIIIB antibody REA (589) that binds to an epitope distinct from 3G8. FcγRIIA levels were evaluated using antibody IV.3. Multiple t-test was used to evaluate the significance between the isotype and 3G8-OVA at the indicated time points, **P<0.005. G) Blood treated as in F) was subjected to Hetasep treatment to isolate leukocytes and RBC lysis. Cells were cultured for 2 days and analyzed for neutrophil (CD10, CD15) and DC markers (CD11c, MHCII). This population was further examined for co-stimulatory molecules, CD80, CD86, chemokine receptor CCR7 and DC subset markers (XCR1, Clec9A, CD141). Multiple t-test comparison was done for significance between Isotype and 3G8-OVA treated blood samples, *P<0.05 and **P<0.005.
Figures 4B, 4C:
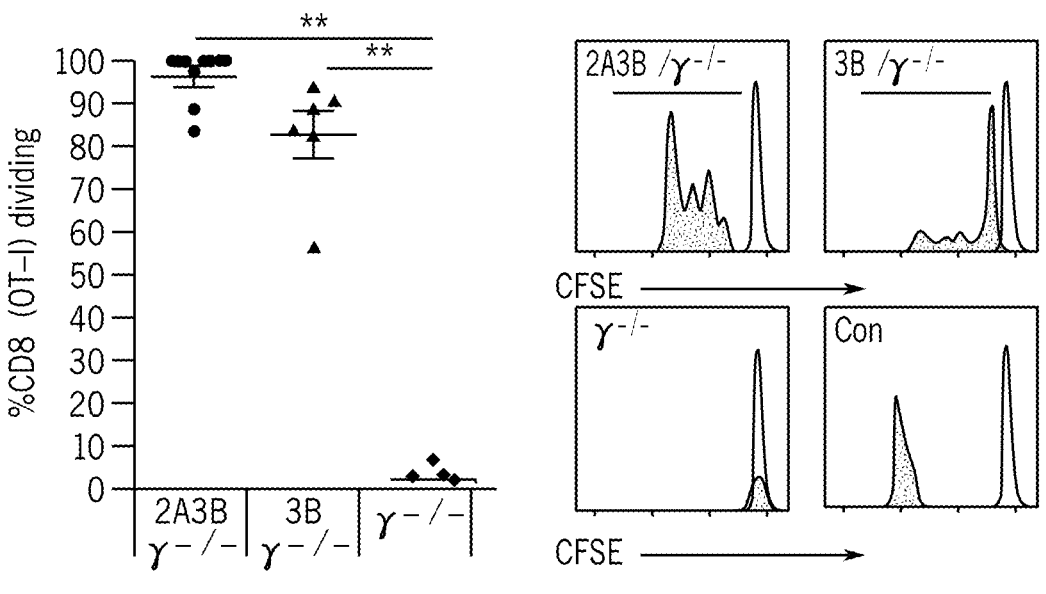

Without wishing to be bound by theory, as shown herein, blood neutrophil FcγR-mediated antigen uptake transduces signals that simultaneously drives antigen uptake and neutrophil differentiation into a mature DC-like phenotype thus ensuring large number of antigen loaded DCs that accumulate in the spleen and promote MHCI and MHCII dependent T cell activation (see schematic in FIG. 8). The presence of NDDC in an antibody-mediated model of kidney inflammation and in SLE patients that have high circulating levels of immune complexes suggests that immune complexes can promote NDDC generation in vivo. The coupling of FcγR-mediated antigen-antibody uptake to differentiation may avoid autoimmune responses as it would preferentially favor the presentation of peptide derived from opsonized, non-self antigens to CD8$^+$ cytotoxic cells[11, 12] as is the case during secondary exposure to antigen. Engaging FcγRIIIB alone is sufficient to trigger neutrophil differentiation into migratory, cross-presenting DCs. This identifies a new role for this elusive neutrophil specific GPI-linked receptor in linking innate and adaptive immunity in response to blood borne antigens and indicates that IC-induced differentiation does not require ITAM signaling. However, despite comparable abilities to stimulate T cell proliferation in vitro (FIGS. 2B-C), mice expressing both FcγRIIA and FcγRIIIB had superior CTL proliferation, target cell killing (FIGS. 4B-C). In classical DCs, durable T cell responses require co-delivery of TLR ligand and/or additional co-stimulatory signals[1]. The FcγR-dependent generation of NDDCs occurred in the absence of adjuvants and, instead required GM-CSF. Clinically, generating DCs ex vivo from the abundant blood neutrophils could circumvent the current need for apheresis in the generation of autologous DCs for cancer immunotherapy[1]. Neutrophil cultures with tumor cells opsonized with anti-tumor antibodies monoclonal antibodies known to exhibit both ADCC and a vaccine effect via FcγRs[11] could also promote antigen sampling of opsonized tumor cells and concurrently drive neutrophil to DC differentiation. The intravenous immunization with FcγRIIIB antibody-antigen conjugates may represent a robust platform to both generate large quantities of DCs in situ and deliver antigen for optimal T cell activation and cross-presentation. Notably, although pro- and anti-tumorigenic functions for neutrophils in cancer have been described[32] the engagement of FcγRs, well-known opsonic receptors in host defense, may harness the neutrophils pro-tumorigenic capacity. In summary, the present studies have identified FcγRIIIB mediated delivery of antigen as a new pathway for both generating DCs and delivering antigen to a compartment favorable for cross-presentation. This process, optionally combined with GM-CSF treatment, can be exploited to generate immunogenic DCs to combat cancer and infection Thus, provided herein are methods to induce antigen specific immunity (e.g., to treat cancer or infection). These methods deliver antigen to neutrophils such that antigen uptake triggers neutrophil differentiation into antigen presenting DCs that activate CD4+ T helper and CD8+ T cytotoxic cells. The methods of delivery are 1) antigen-antibody immune complexes that engage the uniquely human FcγRIIA and GPI-linked FcgRIIIB or murine counterparts on neutrophils to generate NDDCs in vitro that are then administered to patients, and 2) an anti-FcγRIIIB antibody conjugated to antigen (vaccine) that engages activating human FcγRIIIB, known to be selectively expressed on the surface of human neutrophils to generate NDDCs in vivo. In addition to inducing neutrophil differentiation into DCs, the above methods of antigen delivery result in antigen presentation that is superior to presentation of soluble antigen, which is consistent with the published finding in classical DCs that presentation of antigen that is in immune complexes surpasses that of soluble antigen (Wen et al., EMBO Mol Med 8, 1120-1133 (2016).

Thus, described herein are two methods for treating subjects. Either of method 1 or 2 can be used to treat patients with cancer or infectious diseases to increase antigen specific immunity, with potential use as a preventative vaccine to reduce risk of cancer or infection.

As used in this context, to "treat" cancer means to ameliorate at least one symptom of the cancer. Administration of a therapeutically effective amount of a compound described herein for the treatment of a cancer can result in decreased or stabilized tumor burden, decreased or stabilized tumor size, decreased or stabilized tumor growth rate, decreased or stabilized tumor serum markers, and decreased or stabilized risk of metastasis. The subjects can be, e.g., mammals, e.g., human or veterinary subjects. Although humans are used as examples herein, other mammals can also be treated using the present methods, with species-appropriate antibodies and other reagents.

The methods generally include identifying a subject who has a tumor, e.g., a cancer. As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. In general, the methods described herein can be practiced on subjects with solid tumors or hematopoietic tumors, which are malignancies of cells of the immune system. Methods for identifying or diagnosing subjects with cancers are known in the art.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers evaluated or treated by the methods described herein include epithelial cancers, such as a lung cancer (e.g., non-small-cell lung cancer (NSCLC)), breast cancer, colorectal cancer, kidney cancer, head and neck cancer, prostate cancer, or ovarian cancer. Epithelial malignancies are cancers that affect epithelial tissues.

Additional examples of cancers that are potential targets of NDDC therapy include hematologic malignancies. As used herein, the term "hematologic neoplasms" includes cancers that arise for progenitor cells in the bone marrow, such as acute leukemias, myeloproliferative neoplasms, and myelodysplastic syndromes; that arise from peripheral lymphoid tissues, such as non-Hodgkin lymphoma, Hodgkin lymphoma, and leukemias or mature T and B cells (such as chronic lymphocytic leukemia); or that arise from plasma cells or plasma cell precursors (such as multiple myeloma and lymphoplasmacytic lymphoma).

In some embodiments, cancers evaluated or treated by the methods described herein include myeloid neoplasms, malignancies of the immune system, e.g., acute myeloid leukemia (AML), myelodysplastic syndrome (MDS), or myeloproliferative neoplasms (MPN).

Method 1—Cell Therapy

The first methods includes the use of neutrophils that are exposed to antigen-antibody immune complexes that bind to FcγRIIA and/or FcγRIIIB in the presence of GMCSF, to promote their differentiation into dendritic cells (DCs). These DCs are referred to herein as NDDCs, and are expected to be more effective in promoting CD4+ T cell and CD8+ T cell proliferation than DCs generated by GM-CSF plus soluble antigen. Large number of neutrophils can be harvested in a single blood draw as neutrophils represent 55-70% of circulating leukocytes in humans. The method delivers antigen in vitro in immune complexes that engage activating FcγRs to both promote differentiation and facilitate antigen presentation to CD4 T cells and cross-presentation to CD8 cells, a specialized characteristic of classical DCs.

In general, the methods include providing a population of neutrophils. Preferably the neutrophils are autologous, but HLA compatible heterologous neutrophils can also be used. Methods for obtaining neutrophils from a sample of peripheral blood are known in the art and can include commercially available human neutrophil enrichment kit (EASY-SEP). In some embodiments, the population of neutrophils is enriched for cells expressing FcγRIIA and/or FcγRIIIB, e.g., using FACS, microfluidic devices, or other cell sorting methods.

The neutrophils are incubated in the presence of GMCSF (e.g., 5-15 ng/ml, e.g., 8-12 ng/ml, e.g., 10 ng/ml GMCSF) and antigen-antibody immune complexes. These immune complexes include a tumor associated antigen (e.g., a Cancer Testis (CT) antigen, a protein that is normally expressed only on human germ line cells, but is also present in a subset of malignant tumors), e.g., a CT antigen listed in Table A, or a neoantigen that arises from tumor-specific mutations. Neoantigens can arise from any genomic mutation altering protein sequence. See, e.g., Hu, Ott, Wu "Towards personalized, tumor-specific, therapeutic vaccines for cancer." Nat Rev Immunol. 2018 March; 18(3):168-182; Vigneron et al., Cancer Immun. 2013; 13: 15; Hutchison and Pritchard, Mamm Genome. 2018; 29(11): 714-730; Teku and Vihinen, Sci Rep. 2018; 8: 12735; Renkvist et al., Cancer Immunology and Immunotherapy 2001; 50:3-15.

TABLE A

| Tumor antigens (CT Antigens) |
|---|
| MAGEA1 |
| MAGEA2 |

12

TABLE A-continued

| Tumor antigens (CT Antigens) |
|---|
| MAGEA3 |
| MAGEA4 |
| MAGEA5 |
| MAGEA6 |
| MAGEA8 |
| MAGEA9 |
| MAGEA10 |
| MAGEA11 |
| MAGEA12 |
| BAGE |
| BAGE2 |
| BAGE3 |
| BAGE4 |
| BAGE5 |
| MAGEB1 |
| MAGEB2 |
| MAGEB5 |
| MAGEB6 |
| MAGEB3 |
| MAGEB4 |
| GAGE1 |
| GAGE2A |
| GAGE3 |
| GAGE4 |
| GAGE5 |
| GAGE6 |
| GAGE7 |
| GAGE8 |
| SSX1 |
| SSX2 |
| SSX2b |
| SSX3 |
| SSX4 |
| CTAG1B |
| LAGE-1b |
| CTAG2 |
| MAGEC1 |
| MAGEC3 |
| SYCP1 |
| BRDT |
| MAGEC2 |
| SPANXA1 |
| SPANXB1 |
| SPANXC |
| SPANXD |
| SPANXN1 |
| SPANXN2 |
| CT70/BI818097 |
| SPINLW1 |
| TSSK6 |
| ADAM29 |
| CCDC36 |
| LOC440934 |
| SYCE1 |
| CPXCR1 |
| TSPY3 |
| TSGA10 |
| HIWI, MIWI, PIWI |
| PIWIL2 |
| ARMC3 |
| AKAP3 |
| Cxorf61 |
| PBK |
| C21orf99 |
| OIP5 |
| CEP290 |
| CABYR |
| SPAG9 |
| MPHOSPH1 |
| ROPN1 |
| PLAC1 |
| CALR3 |
| PRM1 |
| PRM2 |
| CAGE1 |
| TTK |
| LY6K |
| IMP-3 |

| 13 | | 14 |
|---|---|---|
| TABLE A-continued | | TABLE A-continued |
| Tumor antigens (CT Antigens) | | Tumor antigens (CT Antigens) |

| | | |
|---|---|---|
| AKAP4 | | ARX |
| DPPA2 | 5 | SPEF2 |
| KIAA0100 | | GPAT2 |
| DCAF12 | | TMEM108 |
| SEMG1 | | NOL4 |
| POTED | | PTPN20A |
| POTEE | | SPAG4 |
| POTEA | 10 | MAEL |
| POTEG | | RQCD1 |
| POTEB | | PRAME |
| POTEC | | TEX101 |
| POTEH | | SPATA19 |
| GOLGAGL2 FA | | ODF1 |
| SPANXN3 | 15 | ODF2 |
| SPANXN4 | | ODF3 |
| SPANXN5 | | ODF4 |
| XAGE1D | | ATAD2 |
| XAGE1C | | ZNF645 |
| XAGE1B | | MCAK |
| XAGE1 | | SPAG1 |
| XAGE2 | 20 | SPAG6 |
| XAGE3 | | SPAG8 |
| XAGE-3b | | SPAG17 |
| XAGE-4/RP11-167P23.2 | | FBXO39 |
| XAGE5 | | RGS22 |
| DDX43 | | cyclin A1 |
| SAGE1 | 25 | C15orf60 |
| ADAM2 | | CCDC83 |
| PAGE5 | | TAF7L |
| CT16.2 | | TDRD1 |
| PAGE1 | | TDRD6 |
| PAGE2 | | TDRD4 |
| PAGE2B | 30 | TEX15 |
| PAGE3 | | FATE1 |
| PAGE4 | | TPTE |
| LIPI | | CT45A1 |
| VENTXP1 | | CT45A2 |
| IL13RA2 | | CT45A3 |
| TSP50 | 35 | CT45A4 |
| CTAGE1 | | CT45A5 |
| CTAGE-2 | | CT45A6 |
| CTAGE5 | | HORMAD1 |
| SPA17 | | HORMAD2 |
| ACRBP | | CT47A1 |
| CSAG1 | | CT47A2 |
| CSAG2 | 40 | CT47A3 |
| DSCR8 | | CT47A4 |
| MMA1b | | CT47A5 |
| DDX53 | | CT47A6 |
| CTCFL | | CT47A7 |
| LUZP4 | | CT47A8 |
| CASC5 | 45 | CT47A9 |
| TFDP3 | | CT47A10 |
| JARID1B | | CT47A11 |
| LDHC | | CT47B1 |
| MORC1 | | SLCO6A1 |
| DKKL1 | | TAG |
| SPO11 | 50 | LEMD1 |
| CRISP2 | | HSPB9 |
| FMR1NB | | CCDC110 |
| FTHL17 | | ZNF165 |
| NXF2 | | SPACA3 |
| CDCA1 | | CXorf48 |
| PEPP2 | 55 | THEG |
| OTOA | | ACTL8 |
| CCDC62 | | NLRP4 |
| GPATCH2 | | COX6B2 |
| CEP55 | | LOC348120 |
| FAM46D | | CCDC33 |
| TEX14 | | LOC196993 |
| CTNNA2 | 60 | PASD1 |
| FAM133A | | LOC647107 |
| LOC130576 | | TULP2 |
| ANKRD45 | | CT66/AA884595 |
| ELOVL4 | | PRSS54 |
| IGSF11 | | RBM46 |
| TMEFF1 | 65 | CT69/BC040308 |
| TMEFF2 | | TEKT5 |

15

TABLE A-continued

Tumor antigens (CT Antigens)

NR6A1
TMPRSS12
TPPP2
PRSS55
DMRT1
EDAG, NDR
DNAJB8
CSAG3B
CTAG1A
GAGE12B
GAGE12C
GAGE12D
GAGE12E
GAGE12F
GAGE12G
GAGE12H
GAGE12I
GAGE12J
GAGE13
LOC728137
MAGEA2B
MAGEA9B/LOC728269
NXF2B
SPANXA2
SPANXB2
SPANXE
SSX4B
SSX5
SSX6
SSX7
SSX9
TSPY1D
TSPY1E
TSPY1F
TSPY1G
TSPY1H
TSPY1I
TSPY2
XAGE1E
XAGE2B/CTD-2267G17.3

Where neoantigens are used, preferably the neoantigens expressed in an individual subject are identified and used, e.g., as described in Hu et al., Nat Rev Immunol. 2018 March; 18(3):168-182; Ott et al., Nature. 2017 Jul. 13; 547(7662):217-221; Carreno et al., Science. 2015 348 (6236): 803-808; and Linette and Carreno, Trends Mol Med. 2017 October; 23(10):869-871.

In some embodiments, the tumor antigen is bound to an antibody that recognizes the antigen (via the antigen-binding domain) and binds to FcγRIIA and/or FcγRIIIB (via the Fc domain) to cause clustering of the receptors on the cell surface, which in turn leads to the internalization of the FcγRs and the bound antibody-antigen complexes. In some embodiments, the antibody is IgG, preferably IgG isolated from the individual subject who will be treated. In some embodiments, to purify IgG, serum samples are incubated with Protein G high-capacity agarose beads; other methods for purifying IgG from a subject can be used. Alternatively, IgG from other individuals, e.g., commercially available IgG can be used. Recombinant IgG can also be used. Preferably for human subjects human or humanized IgG is used. In some embodiments, the antibodies are selected or optimized for binding FcγRIIIB and/or FcγRIIA. The Fab regions recognize antigen while the Fc region bind FcγRs. The affinity for Fc is influenced by the FcγRIIA and FcγRIIIB variant and the IgG subclass. Four subclasses of human IgG1 (IgG1-4) exist. The binding affinity of IgG to FcγRIIA and/or FcγRIIIB is highest for IgG1 and IgG3 (Bruhns et al., Blood 113, 3716-3725 (2009); Ivan and Colovai, Hum Immunol 67, 479-491 (2006); Bruggeman et al., J Immunol 199, 204-211 (2017)). Since lower complement activating capacity favors FcγR binding, IgG1 would be preferred over IgG3. Most anti-tumor therapeutic antibodies are also IgG1. FcγR binding is influenced by N-linked glycosylation at Asn297 in the Fc domain. The core N-linked glycoforms can be modified with galactose, fucose and/or sialic acid to generate up to 500 different glycoforms (Jefferis, Nat Rev Drug Discov 8, 226-234 (2009)). Hypofucosylation favors IgG1 interaction with FcγRIIIB while effects on FγRIIA are minimal (Bruhns et al., Blood 113, 3716-3725 (2009); Bruggeman et al., J Immunol 199, 204-211 (2017); Jefferis, Nat Rev Drug Discov 8, 226-234 (2009); Mizushima et al., Genes Cells 16, 1071-1080 (2011); Ferrara et al., Proc Natl Acad Sci USA 108, 12669-12674 (2011); Subedi and Barb, MAbs 8, 1512-1524 (2016); Peipp et al., Blood 112, 2390-2399 (2008)). Thus, IgG1 that is hypofucosylated will be generated to engage neutrophil FcγRIIA and FcγRIIIB See, e.g., Derer et al., MAbs. 2014 Mar. 1; 6(2): 409-421; Zhang et al., J Biol Chem. 2016 Dec. 30; 291(53): 27134-27146; Derer et al., Blood 2013 122:3466; Bruhns et al., Blood 2009 113:3716-3725.

In some embodiments, the antibody is an antibody that recognizes the antigen and binds it directly. For example, existing or new therapeutic antibodies to tumor extracellular or intracellular antigens (e.g., HER2/neu for breast cancer, EGFR for many epithelial tumors like non-small cell lung carcinoma, colorectal cancer, (see, e.g., Corraliza-Gorjon et al., 2017 Front Immunol. doi.org/10.3389/fimmu.2017.01804) or PRL-3, an intracellular cancer related phosphatase that is externalized (Trenevska et al., 2017 Front Immunol. doi.org/10.3389/fimmu.2017.01001); alternatively, the antigen can be produced as a fusion protein with a tag to which the antibody binds. For example, in some embodiments, the antigen-antibody complexes are generated by a method in which the antigen is generated with a "tag" (e.g. KLH, currently used in patients, Wimmers et al., Scientific Reports 7, Article number: 43486 (2017), or polyhistidine, FLAG, Softag1 and Softag3, and Streptag II (see, e.g., Arnau et al., Protein Expression and Purification 48 (2006) 1-13) or human peptide sequence to which a humanized antibody binds. For example, a humanized mouse anti-KLH monoclonal antibody (Abcam, Sino Biologicals, Rockland Immunochemicals) can be used. In this way, antibodies would not have to be tailored to each antigen. The antigen/antibody immune complexes would be incubated with neutrophils to generate NDDC presenting antigen.

The neutrophils can also be incubated in the presence of tumor cells opsonized with anti-tumor antibodies, resulting in neutrophil uptake of debris and antigens and subsequent differentiation into antigen presenting DCs.

The neutrophils can also be incubated with anti-FcgRIIIB (3G8)-antigen conjugate (described in Method 2) and FcgRIIA (IV3)-antigen conjugate where IV3 specifically recognizes FcgRIIA. Another embodiment is a bispecific antibody that contain antigen-binding sites for FcgRIIIB and FcgRIIA in one IgG molecule and would therefore engage and cluster both receptors simultaneously (Sedykh et al., 2018. Bispecific antibodies: design, therapy, perspectives Drug Des Devel Ther. 12: 195-208).

The neutrophils are incubated in the presence of the immune complexes and GMCSF for long enough for the cells to mature into dendritic-type cells (as noted above, referred to herein as NDDCs), e.g., for 2-5 days.

The NDDCs can optionally be maintained in culture for a further time to allow for proliferation. The cells can then be washed, optionally purified and/or concentrated, and administered to a subject, e.g., intravenously. Recovered NDDCs may also be frozen before use.

As shown herein, intravenous delivery of in vitro generated NDDCs with antigen-antibody complexes made with the "model" antigen ovalbumin (OVA) and anti-OVA results in their accumulation in the spleen. Immunized mice exhibited immunity to B16F10-OVA melanoma, which is typically associated with antigen specific CD8 T cells in tumor draining lymph nodes. This immunity was reversed if CD8 T cells are depleted from the mice. In addition, the immunized mice showed a delayed type hypersensitivity response to antigen, which suggested that NDDCs stimulate CD4 T cell functions.

These features are superior to the following two current technologies exploited for delivery of antigen:

The present methods provide an advantage over currently-used technologies that rely on blood apheresis to isolate autologous monocytes followed by generation of antigen loaded DCs in vitro by culturing cells with cytokines and antigen followed by reintroduction of cells into patients (see, e.g., Van Willigen et al., Frontiers in Immunol. 2018 Oct. 1; 9:2265; Tanyi et al., Sci Transl Med. 2018 Apr. 11; 10(436)). Unlike blood monocytes that only represent a small population of peripheral blood cells (2%), neutrophils represent 55-70% of peripheral blood leukocytes, which allows large numbers of these cells to be isolated from a single blood draw and differentiated into NDDCs, eliminating the need for blood apheresis. Presentation of antigen within an immune complex that engages FcγRIIA and FcγRIIIB also promotes antigen cross-presentation and activation of CD8 T cells, which is minimal when soluble antigen is given alone.

Method 2—Anti-FcγRIIIB Antibodies Conjugated to Antigen

Also provided herein are methods in which a construct comprising an anti-FcγRIIIB antibody conjugated to a tumor antigen is used, either in vitro/ex vivo to prepare cells for use in a cell therapy method, or in vivo to stimulate an immune response to the antigen.

As shown herein, incubation of neutrophils expressing human FcγRIIIB or FcγRIIIB+FcγRIIA with anti-FcγRIIIB-OVA conjugate (vaccine) resulted in antigen uptake and neutrophil transdifferentiation into NDDCs. Neutrophils lacking FcγRIIIB did not respond to this treatment. Human neutrophils incubated with anti-FcγRIIIB antibody conjugated to antigen (vaccine) internalized the antigen and differentiate into NDDCs.

Thus in some embodiments, the conjugate is incubated with human neutrophils in the presence of GMCSF, e.g., as described above in Method 1, to drive differentiation into NDDCs that can then be administered to a subject in need thereof.

In in vivo experiments, intravenous delivery of the anti-FcγRIIIB-OVA antigen conjugate led to antigen uptake and the generation of NDDCs in blood that accumulated in the spleen. Immunized mice developed antigen specific cytolytic CD8 T cells as assessed in an in vivo CD8 T cell proliferation and cytotoxic T-lymphocyte (CTL) assay, and developed antigen (i.e. OVA) specific CD8 T cells in a B16F10-OVA melanoma model. Mice that were treated with anti-FcgRIIIB-OVA antigen and 5 consecutive injections of GM-CSF developed antigen (i.e. OVA) specific CD8+ T cells in a B16F10-OVA melanoma model and exhibited a significant reduction in tumor growth.

Thus in some embodiments, the conjugate is delivered intravenously to a subject, optionally in addition to GMCSF. These methods can be used to deliver the antigen intravenously to promote neutrophil differentiation in vivo into NDDC that in turn generate antigen specific cytolytic T cells. The in vivo generation of NDDCs has the advantage of allowing neutrophils to uptake additional antigen, through phagocytosis and trogocytosis of tumor cells as they are differentiating into NDDCs.

The present methods provide an advantage over currently-used technologies that rely on injection of antigen conjugated antibody to classical DC receptors and require the inclusion of adjuvants such as toll like receptor agonists for efficacy (Macri et al., Clin Transl Immunology. 2016 Mar. 18; 5(3):e66; these adjuvants are not needed using the present methods. The route of delivery to access relevant classical DC subset also remains a challenge. The DC receptors targeted in the currently-used technologies are often present in other cell types, which increases the possibility of unwanted side effects while the approach described herein specifically targets FcγRIIIB that is almost exclusively expressed on neutrophils. In addition, as noted above, targeting neutrophils versus DCs is advantageous as neutrophils represent the largest fraction of circulating leukocytes, which increases the number of antigen presenting cells that can be generated in vivo as well as in vitro.

Figure 9A:
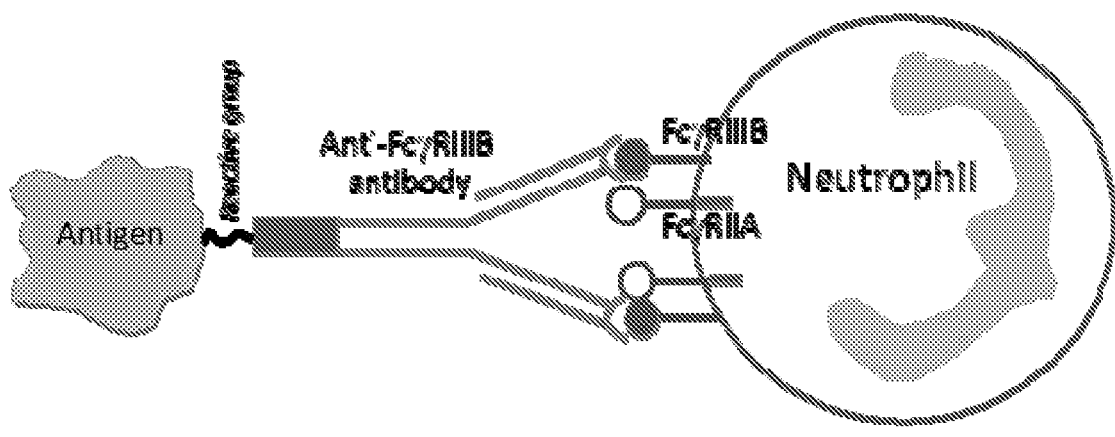

In the present methods, a construct comprising an anti-FcγRIIIB antibody conjugated to a tumor antigen is used (see, e.g., FIG. 9A). Tumor antigens are described above. Anti-FcγRIIIB antibodies are known in the art, as are methods of making them. Anti-FcγRIIIB antibodies are commercially available, e.g., from Abbexa Ltd; Abcam; Abeomics; antibodies-online; Aviva Systems Biology; Biogems International, Inc.; BioLegend; Biorbyt; CEDARLANE; Cell Sciences; Creative Diagnostics; Elabscience Biotechnology Inc.; EXBIO Praha, a.s.; GeneTex; Invitrogen Antibodies; LifeSpan BioSciences; MBL International; Miltenyi Biotec; MyBioSource.com; NSJ Bioreagents; OriGene Technologies; Peninsula Laboratories International, Inc.; ProSci, Inc; R&D Systems; Santa Cruz Biotechnology, Inc.; Signalway Antibody LLC; Sino Biological, Inc.; SouthernBiotech; STEMCELL Technologies, Inc.; and United States Biological. In some embodiments, the antibody is 3G8 (e.g., available from biolegend, Santa Cruz Biotechnology, and others; see, e.g., Perussia and Trinchieri, J Immunol. 1984 March; 132(3):1410-5). These antibodies can be used as-is or modified, e.g., to reduce immunogenicity or alter half-life.

In some embodiments, the antibody also recognizes FcγRIIIA (CD16a: a transmembrane isoform of the GPI-linked FcγRIIIB, CD16b) that is present on macrophages and NK cells. In some embodiments, the antibody is a FcγRIIIB specific antibody that does not bind to FcγRIIIA Method 3—Anti-FcγRIIIB Antibodies (Not Conjugated to Antigen)

Figure 9B:
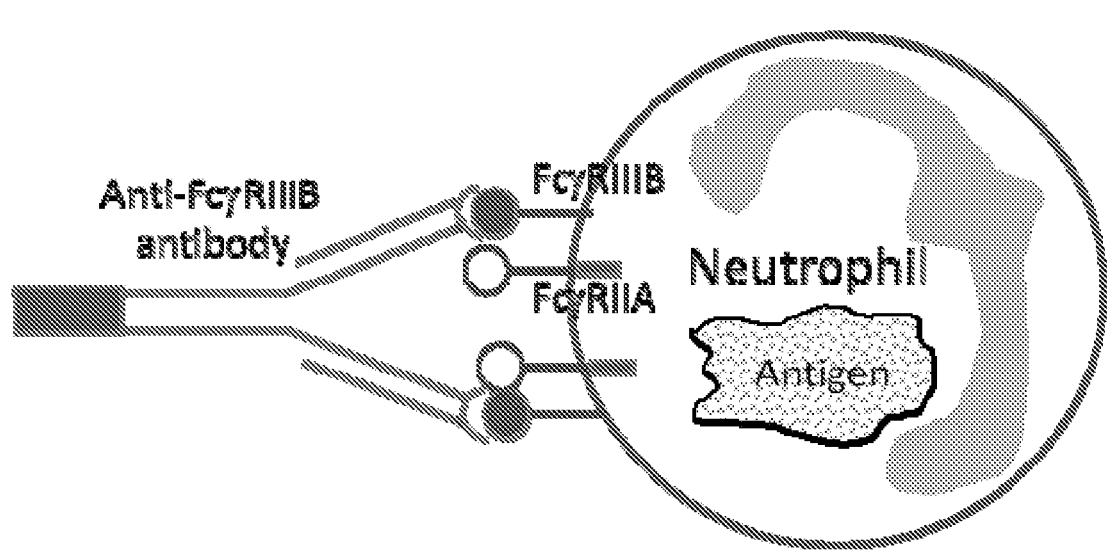

In some embodiments, the anti-FcγRIIIB can be used alone (without a relevant conjugated antigen, see for example FIG. 9B, e.g., for conditions in which neutrophils are the source of antigens, including but not limited to myeloid neoplasms and infections where the neutrophil acquires the antigen following uptake of the pathogen or infected cellular debris or following the infection of the neutrophil itself by the pathogen.

Myeloid Neoplasms

A special cancer treatment problem is found in myeloid neoplasms (including acute myeloid leukemia (AML), myelodysplastic syndrome (MDS), and myeloproliferative neoplasms (MPN)), common tumors of older adults derived from progenitors of the innate immune system that harbor driver and passenger mutations (Lindsley and Ebert, 2013)

that result in neoantigens. These tumors usually relapse after treatment with current chemotherapy regimens, and patients are often too old and/or too sick to tolerate allogeneic stem cell transplantation (Webster and Pratz, 2018).

Several immunotherapy strategies have been developed for these tumors, particularly AML, that involve ex vivo manipulation of the tumor cells to convert them into antigen presenting cells. These methods, which are still being evaluated in preclinical studies and in clinical trials, variously involve transduction of tumor cells in a GMP laboratory with cDNAs encoding antigen-presenting molecules and costimulatory molecules (Shi et al., 2018); fusion of tumor cells with autologous dendritic cells that express these molecules (Rosenblatt et al., 2016); or loading of autologous dendritic cells with tumor neoantigens (for review, see (Van Acker et al., 2019)), each followed by reinfusion back into the patient. In some embodiments, the methods described herein use the FcγRIIIB antibody (without exogenous antigen) to convert neutrophils that originate from a mutated clone into NDDCs. This can be done in vitro using neutrophils from the subject as described above in Method 1, or in vivo, which would eliminate the need for ex vivo manipulation, as well as the need to isolate large numbers of autologous dendritic cells, which can be challenging due to their low abundance, thus requiring blood apheresis. FcγRIIIB antibody-induced NDDCs, loaded with endogenous neoantigens on MHCI, should stimulate the activation of autologous T cells to kill the malignant myeloid cells, including leukemia stem cells that lie at the root of these neoplasms. This strategy does not require ex vivo manipulation of the tumor cells, nor does it require any knowledge of the tumor neoantigens. This is a strategy in which the cancer cells are induced to initiate an immune response against themselves, and as such represents a substantial advance over currently available methods.

Infectious Disease

Neutrophils may also be a source of immunogenic "foreign" antigens in infectious diseases via uptake of pathogens (e.g., bacteria, fungus and virus) or infected cellular material or by direct infection by certain organism such as intracellular bacteria (Rungelrath et al., 2020), herpes viruses (Larochelle et al., 1998; Saez-Lopez et al., 2005) and influenza A virus (Cassidy et al., 1988; Hufford et al., 2012; Wang et al., 2008; Zhao et al., 2008). Virally infected neutrophils were shown to stimulate effector CD8 T cells to generate IFNg but not cytotoxic responses (Hufford et al., 2012), a requisite for anti-tumor immunity. Furthermore, neutrophils were not shown to prime naive CD8 T cells, which is an essential property restricted to classical antigen presenting cells such as DCs and required for subsequent initiation of immune responses (Hufford et al., 2012). The observed ability to present peptide on MHCI for recognition by effector CD8 T cells and subsequent target cell killing is a common property of most nucleated cells that has evolved to protect the host against pathogens. Moreover, the virally infected neutrophils don't express MHCII necessary for activation of naive and effector CD4 T cells (Hufford et al., 2012), which support CD8 T cell responses and other immune functions and thus have limited antigen presenting functions. These methods include the use of an FcγRIIIB antibody (without exogenous antigen) to convert neutrophils that are directly infected or have taken up pathogen into NDDCs in vivo that promote activation of naive CD4 and CD8 T cells and promote CD8 T cell cytolytic functions as has been shown with the anti-FcγRIIIB-antigen conjugate (FIG. 4C). This can be done in vitro, as described above in Method 1 using neutrophils from the subject, or in vivo by administration of the anti-FcγRIIIB antibody. As above, this does not require any knowledge of the immunogenic pathogen-derived antigen.

Antibodies

The term "antibody" as used herein refers to an immunoglobulin molecules, preferably IgG, as well as modified forms, or antigen-binding fragments, variants, or derivatives thereof. The antibody can be polyclonal, monoclonal, recombinant, chimeric, de-immunized or humanized, fully human, non-human, (e.g., murine), or single chain antibody. In some embodiments the antibody has effector function and can fix complement. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume* 1 (*Springer Protocols*) (Springer; 2nd ed., May 21, 2010); Lo, *Antibody Engineering: Methods and Protocols* (*Methods in Molecular Biology*) (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010). When antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735.

Modified forms of antibodies, or antigen-binding fragments, variants, or derivatives thereof described herein can be made from whole precursor or parent antibodies using techniques known in the art. Exemplary techniques are discussed in more detail herein. Antibodies, or antigen-binding fragments, variants, or derivatives thereof described herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof described herein also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular embodiments, antibodies, or antigen-binding fragments, variants, or derivatives thereof described herein will not elicit a deleterious immune response in the animal to be treated, e.g., in a human. In certain embodiments, binding molecules, e.g., antibodies, or antigen-binding fragments thereof described herein are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, VH and VL sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., FcγRIII-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

In some embodiments, a humanized version of the 3G8 antibody is used. 3G8 is a well-characterized mouse IgG k1 mAb specific for FγRIII (CD16). A humanized 3G8 antibody will be as generated using standard methods. The most common method, as described for FcγRIIA mouse antibody, IV.3 (Chen et al. Ann Rheum Dis 78, 228-237 (2019)), is the grafting of the complementary determining regions (CDR) of the heavy and light chains of the mouse 3G8 antibody on to the closest human germline variable heavy and variable kappa chain genes. As the CDR grafting may result in a loss of affinity to the epitope (Safdari et al., Biotechnol Genet Eng Rev 29, 175-186 (2013)), variants with improved binding will be generated by amino acid substitutions in the CDR-grafted domain. These substitutions may follow those identified for a humanized bispecific EGFRxCD16 antibody that used 3G8 as one of the source antibodies (Asano et al., FEBS J 279, 223-233 (2012)).

Methods for conjugating antigens to antibodies are also known in the art. For example, an antibody polypeptide described herein may comprise, consist essentially of, or consist of a fusion protein. These fusion proteins are chimeric molecules which comprise, for example, an immunoglobulin FcγRIII-binding antibody and at least one heterologous tumor antigen sequence. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof described herein may further be recombinantly fused to a heterologous polypeptide at the N- or C-terminus or chemically conjugated (including covalent and non-covalent conjugations) to polypeptides or other compositions.

Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure and Molecular Properties*, T. E. Creighton, W. H. Freeman and Company, New York 2nd Ed., (1993); *Posttranslational Covalent Modification of Proteins*, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

Those skilled in the art will appreciate that conjugates can be assembled using a variety of techniques depending on the selected agent to be conjugated. For example, conjugates with biotin can be prepared, e.g., by reacting an FCγRIII-antibody polypeptide with an activated ester of biotin such as the biotin N-hydroxysuccinimide ester. Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody- Toxin Conjugates", Immunol. Rev. 62 (1982), 119-158. For example, common coupling methods can be used to link antibodies to antigens via free amino, carboxylic acid, or sulfhydryl groups. Some commonly used cross-linking reagents include glutaraldehyde (links molecules to N-terminus of peptides), carbodiimide (EDC) (attaches to C-terminus of peptide); succinimide esters (e.g., MBS, SMCC) (binds free amino group and Cysteine residues); benzidine (BDB) (links to Tyrosine residues), periodate (attaches to carbohydrate groups); isothiocyanate; carbodiimide/activated ester (EDC/NHS) coupling; A reactive azide group can be site specifically introduced to the protein surface using enzymatic ligation as a posttranslational modification, which can in turn be conjugated to an alkyne-containing polymer using highly efficient click chemistry. See, e.g., Paeth et al., Methods Enzymol. 2017; 590:193-224.

The antibodies described herein can be fused to heterologous polypeptides to increase the in vivo half-life of the polypeptides or for use in immunoassays using methods known in the art. For example, in some embodiments, PEG can be conjugated to the antibodies described herein to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Treating and Reducing Risk of Infections Disease

In some embodiments of the methods and compositions described herein, in place of a tumor antigen, an antigen associated with a pathogen is used. The pathogen can be, e.g., a viral, bacterial, fungal, or parasitic pathogen; antigens include viruses as well as their parts and any prokaryotic organism such as bacteria as well as eukaryotic organisms. For example, the pathogen can be, or can be associated with, *E. faecium, S. aureus, K. pneumoniae, A. baumanii, P. aeruginosa,* and *Enterobacter* species, *Clostridium botulinum, Mycobacterium tuberculosis,* HIV, HBV, HCV, human papilloma virus, *Salmonella typhi* (typhoid), *Vibrio cholera, Yersinia pestis,* tuberculosis, malaria/*Plasmodium falciparum,* dengue virus, influenza virus, Lyssa virus, measles virus, *Neisseria meningitidis* type B, smallpox, Chagas' disease, trypanosomiasis, leishmaniasis, babesiosis, or Lyme disease. Methods for identifying peptides for use in targeting these pathogens are known in the art. See, e.g., Verma et al., Vaccine. 2018 Jun. 27; 36(28):4014-4022 (typhoid); Vakli et al., Comput Biol Chem. 2018 February; 72:16-25 (leishmaniasis); Cockburn and Seder, Nat Immunol. 2018 November; 19(11):1199-1211 (malaria); Earla et al., J Anc Dis Prev Rem 2014, Vol 2(1): R1-001; and Delany et al., EMBO Mol Med. 2014 June; 6(6): 708-720. Specific examples include Tat protein, gag p24/p41 and nef for HIV/AIDS (Steinman, Proc (Bayl Univ Med Cent) 21, 3-8 (2008)); Plasmodia Circumsporozoite for Malaria (Steinman, Proc (Bayl Univ Med Cent) 21, 3-8 (2008)); Yersinia Pestis LcrV for pneumonia (Steinman, Proc (Bayl Univ Med Cent) 21, 3-8 (2008)); Leishmania major LACK (Leishmania activated C kinase) antigen for Leishmaniasis (Steinman, Proc (Bayl Univ Med Cent) 21, 3-8 (2008)); Pneumoniae capsular serotype antigen for *Streptococcus pneumonia* (Reglinski et al., NPJ Vaccines 3, 53 (2018); Vi capsular polysaccharide for Salmonella Typhi (Li et al., NPJ Vaccines 3, 1 (2018)); ZIKV non-structural-1 (NS1) protein for Zika virus (Brault et al., Sci Rep 7, 14769 (2017); Major outer membrane protein (MOMP) for Chlamydia trachomatis serovar E, cause of infectious blindness (ocular trachoma) (Pal et al., Infect Immun 73, 8153-8160 (2005)).

The methods and compositions can be used to treat a subject who has an infection, or to elicit an immune response that reduces risk of a later-acquired infection or reduces severity of a later-acquired infection.

Pharmaceutical Compositions and Methods of Administration

The methods described herein can include the use of pharmaceutical compositions comprising an anti-FcγRIII antibody as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic agents, and the like, compatible with pharmaceutical administration. Supplementary active compounds can also be incorporated into the compositions, e.g., GMCSF can be included in the FcgRIII antibody-antigen conjugate immunization. The compositions can also include an adjuvant to increase T cell response. For example, nanoparticles that enhance T cell response can be included, e.g., as described in Stano et al., Vaccine (2012) 30:7541-6 and Swaminathan et al., Vaccine (2016) 34:110-9. See also Panagioti et al., Front. Immunol., 16 Feb. 2018; doi.org/10.3389/fimmu.2018.00276. Alternatively or in addition, an adjuvant comprising poly-ICLC (carboxymethylcellulose, polyinosinic-polycytidylic acid, and poly-L-lysine double-stranded RNA), Imiquimods, CpG oligodeoxynuceotides and formulations (IC31, QB10), AS04 (aluminium salt formulated with 3-O-desacyl-4'-monophosphoryl lipid A (MPL)), ASO1 (MPL and the saponin QS-21), and/or MPLA can also be used. See, e.g., Coffman et al., Immunity. 2010 Oct. 29; 33(4): 492-503; Martins et al., EBioMedicine 3:67-78, 2016; Del Giudice, Seminars in Immunology, 2018, doi.org/10.1016/j.smim.2018.05.001; and Aurisicchio et al., Journal of Experimental & Clinical Cancer Research 2018; 37:86.

Pharmaceutical compositions are typically formulated to be compatible with its intended route of administration. Examples of routes of administration include parenteral, e.g., intravenous administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Materials and Methods

The following materials and methods were used in the Examples below.

Mice

All mice were on a C57B1/6 background and include: wild-type mice, FcR $\gamma^{-/-}$ (Takai et al., Cell 76, 519-529 (1994)), $\gamma^{-/-}$ mice expressing human Fc$\gamma$Rs (Fc$\gamma$RIIA/$\gamma^{-/-}$, Fc$\gamma$RIIIB/$\gamma^{-/-}$ and Fc$\gamma$RIIA+Fc$\gamma$RIIIB/$\gamma^{-/-}$) (Tsuboi et al., Immunity 28, 833-846 (2008)), $\beta$2m$^{-/-}$ (Koller et al., Science 248, 1227-1230 (1990)) (The Jackson Laboratory #002087), MyD88/TRIF$^{-/-}$ (Yamamoto et al., Science 301, 640-643 (2003)), "Catchup" mice expressing tdTomato under the Ly6G promoter (Hasenberg et al., Nat Methods 12, 445-452 (2015)), OT-I (expressing the transgenic T cell receptor recognizing ovalbumin residues residues 257-264 (SIINFEKL; SEQ ID NO:1)) in the context of H2K$^b$ (The Jackson Laboratory #003831), OT-I/beta actin-GFP (obtained by crossing OT-I mice with beta actin-GFP mice) and beta-actin RFP (The Jackson Laboratory, #005884). Animals were maintained in a specific pathogen-free facility. All in vivo experiments were conducted with age and sex matched animals. The Brigham and Women's Hospital Animal Care and Use Committee approved all procedures in this study.

Human Volunteers and SLE Patients and Sera

For studies with SLE patients, peripheral blood samples were obtained from healthy controls and patients with SLE who fulfilled the 1997 ACR classification criteria. The study was approved by the IRB of the Instituto Nacional de Ciencias Méedicas y Nutrición Salvador Zubirán (IRE-2297) and all participants signed informed consent forms. Healthy volunteers without family history of autoimmune diseases were recruited as controls. The clinical and demographic characteristics of the study participants are summarized in Table 1. Human SLE serum samples were obtained from the Lupus Clinic at the Beth Israel Deaconess Medical Center and Instituto Nacional de Ciencias Medicas y de la Nutricion Salvador Zubiran. For studies on normal human neutrophils, and collection of normal sera, blood samples were obtained from healthy volunteers according to protocols for protection of human subjects approved by the Brigham and Women's Hospital Institutional Review Board (P001694/PHS). All volunteer subjects gave written informed consent.

TABLE 1

Demographic and clinical characteristics of study population.

| | SLE patient (SLE) n = 15 | Normal (N) n = 6 |
|---|---|---|
| Female n (%) | 13 (86.6%) | 4 (66.6%) |
| Age n (%) | 37.3 ± 4.2 | 25.6 ± 1.1 |
| SLEDAI mean ± SEM | 6.26 ± 1.9 | |
| Nephritis n (%) | 8 (53%) | |
| C3 mg/dL | 90.6 ± 8.8 | |
| C4 mg/dL | 23.3 ± 3.8 | |
| dsDNA IU/mL | 84.1 ± 32.2 | |
| ESR mm/hr | 9.3 ± 4.4 | |
| CRP mg/L | 0.46 ± 0.15 | |

Abbreviations: SLE, systemic lupus erythematosus; HC, healthy control; SEM, standard error of the mean; SLEDAI, systemic lupus erythematosus disease activity index; dsDNA, double stranded DNA antibodies; ESR, erythrocyte sedimentation rate; CRP, C-reactive protein.

Reagents

Murine GM-CSF (#315-03), human GM-CSF (#300-03), murine G-CSF (#AF-250-05), were from Peprotech. BSA (#A-7970), OVA (#A5503) anti-BSA rabbit antibody (#B7276) and anti-OVA rabbit antibody (#C6534) were form Sigma Aldrich. FITC-OVA (#023020) was from Thermofisher). NIP-OVA (11 NIPs per OVA) and anti-NIP human IgG1 (chimeric antibody with lambda light mouse chains and heavy human chains) were a gift from Richard Blumberg (Brigham and Women's Hosp, Boston). Anti-Fc$\gamma$RIIIB (3G8) (Biolegend) conjugated to FITC-OVA (#023020, Thermofisher) at a ratio of 2 FITC-OVA:1 IgG was generated by Biolegend as described below.

Accutase cell detachment solution (#07920) was from STEMCELL Technologies. FACS antibodies used, including catalog numbers, clones and dilutions, are in Table 2.1 and 2.2. For depletion experiments, anti-mouse CD4 (GK1.5, #BE0003), anti-mouse CD8 (2.43, #BE0061) and rat IgG2b Isotype control (LTF-2, #BE0090) were obtained from BioCell.

TABLE 2.1

Flow cytometric analysis of murine bone marrow derived neutrophils and NDDC

| Antibody | Fluorophore | Company | Clone | Cat# | Dilution |
|---|---|---|---|---|---|
| CD3 | BV605 | BioLegend | 17A2 | 100237 | 1:100 |
| CD11c | BV605 | BioLegend | N418 | 117334 | 1:100 |
| F4/80 | BV605 | BioLegend | BM8 | 123133 | 1:100 |
| CD80 | BV605 | BioLegend | 16-10A1 | 104729 | 1:100 |
| NK-1.1 | BV605 | BioLegend | PK136 | 108739 | 1:100 |
| Ly-6G | BV605 | BioLegend | 1A8 | 127639 | 1:100 |
| CCR7 | Pe/Cy7 | BioLegend | 4B12 | 120123 | 1:100 |
| Ly-6G | PB | BioLegend | 1A8 | 127611 | 1:100 |
| Ly-6C | PB | BD | Al-21 | 562727 | 1:100 |
| CD11b | PB | BioLegend | M1/70 | 101224 | 1:100 |
| CD103 | PB | BioLegend | 2E7 | 121421 | 1:100 |
| Ly-6C | PB | BioLegend | HK1.4 | 128013 | 1:100 |
| CD86 | PB | BioLegend | GL-1 | 105022 | 1:100 |
| Ly-6G | Pe/Cy7 | BioLegend | 1A8 | 127618 | 1:100 |
| CD115 | Pe/Cy7 | BioLegend | AFS98 | 135524 | 1:100 |
| CD40 | Pe/Cy7 | BioLegend | 3/23 | 124622 | 1:100 |
| CD103 | Pe/Cy7 | BioLegend | 2E7 | 121425 | 1:100 |
| CD11b | Pe/Cy7 | BioLegend | M1/70 | 101216 | 1:100 |
| CD8a | Pe/Cy7 | BioLegend | 53-6.7 | 100722 | 1:100 |
| CD8a | PerCP | BioLegend | 53-6.7 | 100732 | 1:100 |
| CCR7 | PerCP | BioLegend | G043H7 | 353242 | 1:100 |
| MHC class II | PerCP | BioLegend | AF6-120.1 | 116415 | 1:100 |
| Ly-6G | PerCP | BioLegend | 1A8 | 127616 | 1:100 |
| Ly-6G | APC | BioLegend | 1A8 | 127614 | 1:100 |
| CD11c | APC | BioLegend | N418 | 117310 | 1:100 |
| Ly-6C | AF647 | BioLegend | HK1.4 | 128009 | 1:100 |
| CD8a | APC | BioLegend | 53-6.7 | 100711 | 1:100 |
| CD115 | APC | BioLegend | AFS98 | 135509 | 1:100 |
| CD11b | Pe | BioLegend | ICRF44 | 301306 | 1:100 |
| CD86 | Pe | BioLegend | 34F | 200308 | 1:100 |
| CCR7 | Pe | BioLegend | 4B12 | 120105 | 1:100 |
| CD11c | Pe | BioLegend | N418 | 117307 | 1:100 |
| CD115 | Pe | eBioscience | AFS98 | 12-1152-82 | 1:100 |
| Ly-6G | FITC | BioLegend | 1A8 | 127606 | 1:100 |
| CD80 | FITC | BioLegend | 16-10A1 | 104705 | 1:100 |
| CD8a | FITC | BioLegend | 5H10-1 | 100804 | 1:100 |
| H-2 K$^b$ OVA Tetramer (OVA257-264 [SIINFEKL] (SEQ ID NO: 1) | Pe | NIH | | | 1:600 |
| CD3 | BV605 | BioLegend | 17A2 | 100237 | 1:100 |
| Foxp3 | PB | BioLegend | MF-14 | 126419 | 1:100 |
| CD69 | PB | BioLegend | H1.2F3 | 104527 | 1:100 |
| CD4 | PB | BioLegend | GK1.5 | 100443 | 1:100 |
| CD4 | PB | BioLegend | RM4-4 | 116008 | 1:100 |
| CD69 | Pe/Cy7 | BD | H1.2F3 | 552879 | 1:100 |
| CD25 | Pe/Cy7 | BioLegend | PC6.1 | 102016 | 1:100 |
| CD44 | Pe/Cy7 | BioLegend | IM7 | 103030 | 1:100 |
| CD62l | APC | BioLegend | MEL-14 | 104411 | 1:100 |
| Ki67 | PerCP | BioLegend | B56 | 561284 | 1:100 |
| T-bet | AF647 | BioLegend | 4B10 | 644803 | 1:100 |
| PD-1 | APC | BioLegend | RMP1-30 | 109112 | 1:100 |
| CTLA-4 | APC | BioLegend | UC10-4B9 | 106310 | 1:100 |
| CD3 | APC | BioLegend | 145-2C11 | 100311 | 1:100 |
| PD-1 | Pe | BioLegend | RMP1-14 | 114117 | 1:100 |
| MHC class II | Pe | eBioscience | NIMR-4 | 12-5322-81 | 1:100 |
| CD25 | PE-CF594 | BD | PC61 | 562695 | 1:100 |

TABLE 2.2

Flow cytometric analysis of human blood and cultured blood neutrophils and NDDC

| Antibody | Fluorophore | Company | Clone | Cat# | Dilution |
|---|---|---|---|---|---|
| CD80 | APC-H7 | BD | L307.4 | 561134 | 1:100 |
| XCR1 | Pe | BioLegend | S15046E | 762603 | 1:100 |
| CD86 | BV421 | BioLegend | IT2.2 | 305426 | 1:100 |
| CD141 | Pe/Cy7 | BioLegend | M80 | 344109 | 1:100 |
| CD11c | BV421 | BD | 3.9 | 565807 | 1:100 |
| CD14 | APC | BioLegend | M5E2 | 301808 | 1:100 |

TABLE 2.2-continued

| CD15 | BV605 | BioLegend | W6D3 | 323031 | 1:100 |
|---|---|---|---|---|---|
| CD10 | Pe | Ancell Corporation | SN5c/L4-1A1 | 157-050 | 1:100 |
| SiglecH | Pe | eBioscience | eBio440c | 12-0333-80 | 1:100 |
| CD11c | APC/Cy7 | BioLegend | Bu15 | 337218 | 1:100 |
| CD11b | Pe | BioLegend | ICRF44 | 301306 | 1:100 |
| HLA-DR | Bv605 | BioLegend | L243 | 307639 | 1:100 |
| Clec9a | AF488 | R&D Systems | 683409 | FAB6049G | 1:100 |
| CD10 | BV421 | BD | H10a | 562902 | 1:200 |
| CD11c | AF647 | BioLegend | 3.9 | 301619 | 1:100 |
| CD197 | BV421 | BD | 150503 | 562555 | 1:100 |
| CD80 | Pe/Cy7 | BioLegend | 2D10 | 305218 | 1:100 |
| CD86 | PerCP | BioLegend | IT2.2 | 305419 | 1:100 |
| CD11b | Pe/Cy7 | BioLegend | M1/70 | 101216 | 1:100 |
| CD15 | PerCP | BioLegend | W6DE | 323020 | 1:100 |
| Clec9A | Pe | BioLegend | 8F9 | 353803 | 1:100 |
| CD16 | Pe | BD | 3G8 | 555407 | 1:100 |
| CD32 | Pe | BD | FLI8.26 | 550586 | 1:100 |
| CD16 | APC Vio770 | MACS-Miltenyi Biotech | REA589 | 130-109-147 | 1:100 |

For normal and SLE patient blood samples:

| CD11c | PE | BioLegend | 301606 | 3.9 | 1:20 |
|---|---|---|---|---|---|
| CD10 | APC/Cy7 | BioLegend | 312212 | HI10A | 1:20 |
| CD15 | FITC | BioLegend | 301903 | HI98 | 1:100 |
| HLA-DR | PE/Cy7 | BioLegend | 307616 | L243 | 1:100 |
| CD3 | PerCP/Cy5.5 | BioLegend | 300328 | HIT3a | 1:100 |
| CD19 | PerCP/Cy5.5 | BioLegend | 302230 | HIB19 | 1:100 |
| CD56 | PerCP/Cy5.5 | BioLegend | 318322 | HCD56 | 1:100 |
| CD14 | Pacific Blue | BioLegend | 301828 | M5E2 | 1:100 |
| CD197 (CCR7) | Pacific Blue | BioLegend | 353210 | G043H7 | 1:100 |
| CD80 | APC | BioLegend | 305220 | 2D10 | 1:100 |
| CD141 | BV605 | BD OptiBuild | 740421 | 1A4 | 1:100 |
| CD370 (CleC9) | APC | BioLegend | 353806 | 8F9 | 1:100 |

Isotype controls and Fc block reagents

| Human TruStain FcX | | Biolegend | 422302 |
|---|---|---|---|
| Mouse BD Fc Block | | BD | 553141 |
| Mouse IgG1k | | BD | 557273 |
| Mouse IgG1k-FITC | | Invitrogen | 11-4714-81 |

Conjugation Method Used by Biolegend

FITC-OVA conjugation to 3G8 antibody is achieved by click chemistry. FITC-OVA lyophilized powder (Thermofisher, cat #023020) was dissolved in phosphate buffer pH 7.0 and activated with azide containing reagent Azido-PEG4-NHS Ester (Click Chemistry Tools). The azide-activated FITC-OVA is purified by G-25 sephadex resin. The 3G8 antibody is activated by DTT followed by DBCO-PEG4-Maleimide (Click Chemistry Tools). The DBCO-modified 3G8 antibody is incubated with azide-activated FITC-OVA at a molar ratio of 1:3 (Antibody: Dye). The conjugation is quenched with sodium azide and loaded onto a superdex 200 column to separate free antibody from free FITC-OVA. Fractions containing 1:1 and 1:2 (Ab:FITC-OVA) were pooled with the final ratio being approximately 1.4~1.5.

Generation of Model ICs

To generate insoluble immune complexes, solutions containing 2 mg/ml of anti-OVA, anti-NIP-OVA or anti-BSA antibodies were added to 0.2 mg/ml of OVA, FITC-OVA, NIP-OVA or BSA or 0.1 mg/ml of OVA, FITC-OVA, NIP-OVA or BSA in PBS at a 1:1 ratio and incubated overnight at 37° C. to generate IC that are referred to as IC solution 1 and IC solution 2, respectively. The excess antibody in the mixture results in the appearance of a precipitate (insoluble immune complexes).

Sera, IgG Isolation and Generation of Immune Complexes with RNP

Peripheral blood was drawn into BD Vacutainer™ Venous Blood Collection Tubes SST. Tubes were centrifugated at 2500/g for 30 min. Serum was aliquoted and frozen at −80° C. To purify IgG, serum samples were incubated with Protein G high-capacity agarose beads (Genesee Scientific, #20-538). Antibody was eluted with 0.1M Glycine (pH2.7) and the samples were neutralized immediately with the neutralization buffer (1M Tris-HCl, pH 9). The samples were then dialyzed in PBS overnight and concentrated using 100 kDa centrifugal filters (Millipore, UFC910024). To generate SLE-IgG/RNP immune complexes, solutions containing 2 mg/ml of purified SLE IgG or normal human IgG were mixed with equal volumes of 0.3 mg/ml of Sm/RNP complexes (#SRC-3000, Immunovision) in PBS (without Ca, Mg) and incubated for 4 hrs at 37 C. 20 ul/ml of immune complex solutions were added to neutrophils to generate human or murine dendritic cells. RNP was used at 3 ug/ml. SLE-IgG or normal human IgG alone were used at 20 ug/ml.

Isolation, Treatment and Culture of Bone Marrow Derived Murine Neutrophils

Neutrophil isolation: Mice were euthanized and femurs and tibias were flushed with ice-cold RPMI 1640 using a 25-gauge needle attached to a 20 cc syringe and clumps were dispersed by passing the cell suspension through a 1 ml pipet tip several times. Collected cells were filtered through a 70 um strainer into a 50 ml Falcon tube, pelleted and resuspended in PBS containing 2% FBS and 1 mM EDTA at $1 \times 10^8$ cells/ml. Neutrophils were isolated by negative selection using the EasySep Mouse Neutrophil Enrichment Kit 19762 (STEMCELL Technologies). Aliquots of the isolated cells were taken to determine neutrophil count and viability by trypan blue exclusion. Viability was also determined by FACS using the fluorescent viability dye Fixable Viability Dye eFluor 780 (ThermoFisher). Purity was assessed by flow cytometry (see FIG. 6)

Conditions for generating NDDC in vitro: Isolated murine neutrophils were resuspended in RPMI medium (RPMI 1640 with L-glutamine and 25 mM HEPES, supplemented with 10% fetal calf serum and penicillin/streptomycin (50 U/ml penicillin and 50 μg/ml streptomycin). $2 \times 10^6$ cells/well were plated in 6-well plates in 2 ml of RPMI medium and incubated at 37° C. in 5% $CO_2$. Neutrophils were additionally cultured with one or more of the following: GM-CSF (10 ng/ml), SLE patient IgG or normal human IgG (20 ug/ml), with 10 ng/ml of GM-CSF, or with SLE patient sera or normal human sera (50 ul/ml) alone (without GM-CSF). For treatment with ICs, prepared IC containing solutions as described in "Generation of model immune complexes" were mixed thoroughly before use and cells were incubated with 10 μl/ml of IC solution 1 plus 10 μl/ml of IC solution 2 (OVA, FITC-OVA, NIP-OVA or BSA containing ICs). For treatment with antigen alone, soluble OVA, FITC-OVA, NIP-OVA or BSA were used at 1.5 μg/ml, amounts that are equivalent to that contained in their respective ICs. For treatment with antibody alone, cells were incubated with 20 ug/ml anti-OVA, anti-BSA or anti-NIP-OVA. Neutrophils were incubated for 2 hrs at 37C, 5% CO2 in medium in falcon tubes with gentle rocking. Cells were pelleted at 300 g, washed with PBS and cultured in RPMI medium supplemented with 10 ng/ml of GM-CSF. After 3 days of culture, non-adherent and adherent cells were harvested using Accutase (STEMCELL Technologies), washed with PBS and resuspended in FACS buffer for flow cytometric analysis as described. For in vivo injection, only adherent cells harvested with Accutase were used.

Human Neutrophil Treatment and In Vitro Culture Conditions

Peripheral blood was drawn from healthy human volunteers into tubes containing trisodium citrate, citric acid and dextrose (Vacutainer ACD Solution A, BD). Autologous serum, used for culture of cells was obtained by drawing blood into BD Vacutainer™ Venous Blood Collection Tubes SST, centrifuging at 2500×g for 30 min and collecting the supernatant. For generation of NDDC in vitro, blood was supplemented with GM-CSF (10 ng/ml) for 30 min at 37° C. followed by addition of FITC-IgG isotype control or FcγRIIIB (3G8)-FITC-OVA conjugate for 2 h. Blood was then incubated with Hetasep (STEMCELL Technologies) according to manufacturer protocols to deplete red blood cells and enrich leukocytes. The leukocyte-rich plasma layer was washed with PBS and the residual red blood cells were lysed using ammonium chloride solution for 10 minutes on ice, washed with PBS and resuspended in RPMI 1640 with L-glutamine and 25 mM HEPES, which was supplemented with 2.5% autologous serum and penicillin/streptomycin (50 U/ml penicillin and 50 ng/ml streptomycin). $2 \times 10^6$ cells were plated in 6-well plates in 2 ml of medium supplemented with 10 ng/ml of GM-CSF or 50 μl/ml of serum from healthy donors of from SLE patients. After 48 hours, cells were harvested using Accutase and evaluated for dendritic cell differentiation by flow cytometry as described.

Flow Cytometry

Flow cytometry was performed on either a FACSCanto II or LSRFortessa-12-color analyzers. FCS (flow cytometry standard format) 3.0 data file was used to export data that was analyzed using FlowJo (Mac version 10.5). Compensation controls were created for each fluorochrome. BD multicolor compensation beads were stained as compensation controls for FITC, Pe, Pe/Cy7, PerCP Cy5.5, APC, APC/Cy7, BV421 and BV605. For all experiments, cells were stained with the Fixable Viability Dye eFluor 780 (ThermoFisher) to gate out dead cells. Forward and side scatter gates were used to discriminate doublets and debris (FSC-A, FSC-H, SSC-A×SSC-H). Matched isotypes were used as controls, negative gating was based on FMO (fluorescence minus one) strategy. Only viable cells were included for the studies.

For surface staining, single cell suspensions in FACS buffer (PBS supplemented with 2% FCS and 2 mM EDTA) were incubated with mouse BD Fc block or human TruStain FcX for 20 min at 4 C. Samples were incubated with the indicated fluorochrome-conjugated antibodies for 30 min at 4 C, washed with PBS and fixed with 1% paraformaldehyde.

Flow Cytometric Analysis of Murine Bone Marrow Derived Neutrophils and NDDCs

For phenotypic and functional analysis of bone marrow derived neutrophils and NDDC, antibodies for the following cell surface markers were used: CD11c, MHC-II, Ly6G, CD80, CD86 and CCR7 (see Table 2.1 for details). Within the viable population of lineage negative (CD3, NK1.1 and CD19), CD11c$^+$ and MHC-II$^+$ events were gated and Ly6G expression was analyzed. The CD11c$^+$MHC-II$^+$ and Ly6G$^+$ population was further analyzed for expression of co-stimulatory molecules CD80, CD86 and the migratory marker CCR7. The CD11c gates were based on FMO controls and CD80, CD86 and CCR7 were based on isotype and FMO controls. Displayed numbers are CD11c$^+$, MHC-II$^+$ and Ly6G$^+$ events expressed as %. The subset DC markers XCR1, CD103 and CD8a were analyzed further on CD11c$^+$, MHC-II$^+$ and Ly6G$^+$ population. For uptake analysis, FITC and Ly6G gates were set based on isotype control. Anti-Ly6G was coupled with APC fluorochrome. For OT-I and OT-II experiments, anti-CD3, -CD4 and -CD8 antibodies were used. Singlets of CD3$^+$, CD4$^+$ or CD8$^+$ viable cells were gated for further analysis. Histograms are from one representative donor, display populations of CFSE+ events (filled histogram) and were set based on isotype controls. Clear histograms indicate day 0 staining of CFSE$^+$ events.

For intracellular staining, fixed cells were stained for surface markers and permeabilized with BD perm/wash buffer (BD Biosciences). Cells were then stained with the following antibodies: anti-Foxp3, -T-bet and -Ki-67. Cells were washed again with permeabilization buffer and analyzed by flow cytometry Flow Cytometric Analysis of Human Blood Neutrophils and Dendritic Cells To evaluate cell markers in circulating leukocytes in whole blood of SLE patients and paired normal controls, 100 μL of blood was incubated with antibodies for the following surface markers: CD10, CD15, CD11c, MHC-II, CD80, CCR7 (see Table 2.2). Within the viable population of lineage negative (CD3, CD19 and CD56), CD11c$^+$ and MHC-II$^+$ events were gated and CD10 and CD15 expression was analyzed. The CD11c$^+$MHC-II$^+$, CD10$^+$ and CD15+ population was further analyzed for CD80 and CCR7 markers. The DC subset markers Clec9a, XCR1 and CD141 were also evaluated. Red blood cells were lysed using lysis buffer (BD Pharm Lyse) and the samples were analyzed by flow cytometry in an LSR Fortessa cytometer (BD bioscience).

Analysis of FITC-OVA, FITC-OVA/Anti-OVA and Anti-FcγRIII-FITC-OVA Uptake in vitro.

For murine neutrophil uptake experiments, cells from the indicated genotypes were cultured with FITC-OVA or FITC-OVA-anti-OVA model immune complexes generated as detailed above. At the indicated times, cells were collected, stained with anti-Ly6G and subjected to FACs analysis.

For human neutrophil uptake measurements, blood was incubated at 37C with FITC-IgG isotype control or anti-FcγRIIIB (3G8)-FITC-OVA antibody conjugate (8.5 to 12.5 μg/ml) with gentle agitation on a rocking table for the indicated times. Samples were then treated with ammonium chloride solution (STEMCELL Technologies #07800) for 10 minutes on ice to lyse red blood cells, washed with PBS and subjected to FACS analysis with the indicated antibodies: anti-CD10, -CD15-CD16 (REA-589) -CD16(3G8) and -CD32 (IV3).

Immunization with NDDC or FcγRIIIB-FITC-OVA

Neutrophils isolated from WT or MyD88/TRIF–/mice were incubated with PBS (vehicle), OVA or OVA-anti-OVA ICs for 2 hrs and cultured in RPMI medium (RPMI 1640 with L-glutamine and 25 mM HEPES, supplemented with 10% fetal calf serum and penicillin/streptomycin (50 U/ml penicillin and 50 μg/ml streptomycin) with 10 ng/ml GM-CSF. After 3 days, non-adherent cells were gently removed and the remaining adherent cells were detached with Accutase. $1 \times 10^6$ cells were injected intravenously into Isofluorane anesthetized mice 7 days prior to inoculation of B16F10-OVA cells. For immunization studies, 100 μl of PBS solution containing the 3G8 (anti-FcγRIIIB)-FITC-OVA (30 μg) or FITC-OVA (12 μg), was injected i.v. into mice 6 hrs after an intraperitoneal injection of 5 μg of GM-CSF. 4 additional daily injections of GM-CSF were given. 10 days after 3G8-OVA conjugate or FITC-OVA injection, mice were challenged with a subcutaneous injection of $2 \times 10^5$ B16F10-OVA cells.

Blood and Spleen Analysis for Detection of Ag Uptake and Neutrophil-DC Markers.

γ–/–, 3B γ–– and 2A3B γ–/– mice were injected retro orbitally with 30 μg of 3G8 (anti-FcγRIIIB)-FITC-OVA. Blood samples were taken at the indicated times and subjected to red blood cell lysis using ACK lysis buffer, washed with PBS and analyzed by FACS with antibodies for the following markers: Ly6G, CD11c, CD11b, MHC-II, CD80 and CCR7 (FIG. 4A; Ly6C, CD115, CD16 (REA-589) and CD32 (FIG. 7). were harvested after 3 days and processed as described in organ harvest section.

OTI and DTII Proliferation Assays In Vitro and In Vivo:

In vitro: T-cells from the ovalbumin specific transgenic OT-I and OT-II mice were isolated from spleen and lymph nodes by positive selection. Cells were enriched with microbeads conjugated to anti-mouse CD8a (Ly-2) (Miltenyi) for enrichment of CD8+ T-cells or anti-mouse CD4 (L3T4) (Miltenyi) for CD4+ T-cell enrichment. Final preparations contained 85-90% CD8+ or CD4+ T-cells. $0.5 \times 10^6$ bone marrow neutrophils from the indicated genotypes were loaded with OVA, OVA-IC or vehicle control as described earlier, seeded in 96-well microplates in RPMI medium (10% FCS) supplemented with GM-CSF and cultured for 3 days to generate NDDC. As a positive control, NDDC were pulsed with 1μ/ml OVA$_{257-264}$ 24 hrs prior to the addition of T cells.

Cells were CFSE labeled to assess proliferation. For this, OT-I and OT-II cells were resuspended in PBS ($10^7$ cells/ml) containing 0.1% bovine serum albumin (Sigma) and incubated with CellTrace Violet at 5 μM for 20 min at 37 C. The reaction was stopped with 10% FCS and the cells were washed twice with cold PBS and resuspended in RPMI supplemented with 10% FCS, L-glutamine and pen/strep. NDDC were co-incubated with 2×105 CellTrace Violet-labeled OT-I or OT-II cells. After 3 days of culture with OT-I or 5 days with OT-II, cells were washed with PBS and stained for analysis by flow cytometry.

In vivo: Enriched OT-I and OT-II cells were labeled with CellTrace Violet dye as described for in vitro assays. Cells were resuspended in PBS and injected i.v. ($3 \times 10^6$ cells/mouse) into recipient mice that had received an i.v. injection of 30 ug of FcγRIIIB-FITC-OVA conjugate at day –10. At day 4 after priming, mice were euthanized and cells from the spleen were harvested and stained for flow cytometry analysis.

CTL Assay

Recipient mice were injected with 30 ug of FcγRIIIB-FITC-OVA at day –7. At day 0, target splenocytes were generated by harvesting spleens from WT naïve mice and incubating half the cells with ("pulsed") half without ("unpulsed") 1 μg/ml OVA$_{257-264}$ (SIINFEKL (SEQ ID NO: 1) Analytical Biotechnology Services, Boston) for 1 hr at 37C in RPMI supplemented with 10% FCS. The cells were washed and resuspended in PBS and the pulsed and unpulsed cells were labelled with 6 μM CellTrace Violet (Thermofisher, C34557) (pulsed) or 1 μM CellTrace Violet (unpulsed) respectively for 20 min at 37 C. The cells were washed and resuspended in PBS, and $1 \times 10^6$ pulsed and $1 \times 10^6$ unpulsed cells were injected i.v. into the indicated recipient mice. 16 hours later, spleens from recipient mice were harvested and assessed for loss of pulsed targets by flow cytometry. The following equations were used to determine the actual value of cell specific lysis[6]: Ratio=Irrelevant Percentage: Epitope Specific Percentage ([unpulsed] peak: [pulsed] peak), Percent Specific Lysis= [1–(Non-transferred control ratio/experimental ratio)]×100.

B16F10-OVA Tumor Challenge, Organ Harvest and flow Cytometric Analysis

B16F10 cells expressing soluble OVA were cultured in vitro in DMEM/high glucose supplemented with 10% fetal calf serum and maintained at sub-confluent density. Mice were anesthetized with an intraperitoneal injection of a ketamine/xylazine cocktail (90 mg/kg ketamine, 10 mg/kg xylazine), shaved and injected in the flank subcutaneously with $2 \times 10^5$ tumor cells in 100 μl HBSS. Tumors were measured with a caliper every 1-2 days once palpable in any one group (long diameter and short diameter) and tumor volume was calculated using an ellipsoid formula ($\frac{1}{2} \times D \times d^2$) where D and d are the longer and shorter diameter respectively. For antibody treatments, mice were given 100 μg of the anti-CD4 or anti-CD8 antibody or isotype controls via an intraperitoneal injection at the indicated days. Organs and tumors were surgically removed and processed within 30 minutes of removal.

Briefly, on ice, all excess fat was removed. The organs were gently dissociated in FACS buffer (PBS supplemented with 2% FCS and 2 mM EDTA) by shearing the tissue on a 70 μm nylon cell strainer (FisherBrand) using a 3 ml syringe plunger. Cells from draining and non-draining lymph nodes and tumors were washed with PBS and stained with antibodies for analysis by flow cytometry. Cells from spleens were subjected to red blood cell lysis using ACK lysis buffer solution (Lonza Cat 10-548E) for 2 min. at room temperature, washed once with PBS and resuspended in FACS buffer. Blood was collected from the retroorbital plexus of isofluorane anesthetized mice using micro-hematocrit capillary tubes into EDTA tubes (final 5 mM). Samples were subjected to red blood cell lysis using ACK lysis buffer for 10 min at room temperature, washed with PBS and resuspended in FACS buffer. For flow cytometric analysis, cells were analyzed for expression of CD4, CD8, CD44, CD62L, HLA-DR tet (H-2 $K^b$ OVA Tetramer (OVA257-264)), CD69, CD25, PD-1, Foxp3, Ki-67 and T-bet.

Delayed Type Hypersensitivity (DTH) Responses:

OVA-IC or OVA fed neutrophils were cultured in the presence of GM-CSF. 3 days later, non-adherent cells were discarded and adherent cells were harvested using Accutase and $1 \times 10^6$ NNDC were injected i.v. into wild type recipient mice. 7 days after immunization, 50 µg of soluble OVA in 100 µl PBS was injected into the right rear foot pad and an equal volume of PBS was injected in the left rear foot pad and served as a control. Paw swelling was measured on day 0 before OVA injection and 24 hours after OVA challenge using digital calipers. The magnitude of the DTH response was calculated as the thickness after and before OVA challenge. For histological analyses of the DTH response, paws were collected, fixed in formalin solution, neutral buffered, 10% (Sigma, HT-50-14-120 ml) and processed for H&E staining using standard histopathological methods. Inflammatory score was determined blindly.

Anti-GBM Nephrotoxic Nephritis 12-weeks-old mice were preimmunized subcutaneously with 0.05 mg of rabbit IgG (Thermofisher #31235) with incomplete Freund's adjuvant (Thermo) and nonviable desiccated Mycobacterium tuberculosis H37Ra (Difco, Michigan) at day −3 and given an intravenous injection of 100 µL nephrotoxic serum (NTS) at day 0. Control animals received an injection of PBS at day −3 and an intravenous injection of PBS at day 0. Spot urine samples were collected at the indicated time points and mice were euthanized for histological and FACS analysis at day 14. Kidneys were harvested using Collagenase Type II/Hyaluronidase (StemCell Technologies) and draining lymph nodes, non-draining lymph nodes and spleen were harvested as described above for the B16F10 tumor model. Td-tomato+ cells were gated, analyzed for CD11c and MHC-II expression and positive cells were evaluated for CD80 and CD86 expression. Subset DC marker analysis included CD8a, XCR1 and CD103.

Intravital Microscopy of Popliteal Lymph Node

Approximately $5 \times 10^5$ NDDCs generated with OVA-IC as described for the DTH model were resuspended in 25 µl of PBS and injected into the right hind footpad of wild-type C57Bl/6 mice at day 0. (10-10.5)$\times 10^6$ OT-1 β-actin-GFP cells in 200 µl PBS were injected i.v. 30 minutes before NDDC injection. At day 3 after NDDC injection, mice were anesthetized with a mixture of ketamine (50 mg kg−1) and xylazine (10 mg kg−1) injected intraperitoneally. The jugular vein of the anesthetized mice was cannulated to allow intravenous delivery of Qtracker 655 Vascular dye as well as additional anesthetics if required. The right popliteal lymph node was prepared microsurgically and positioned on a custom-made microscope stage for intravital microscopy. During microsurgery, attention was given to spare blood vessels and afferent lymph vessels. The exposed lymph node was submerged in normal saline, covered in glass coverslip with a thermocouple placed next to the lymph node to monitor local temperature which was maintained at 37° C. Two-photon intravital imaging was performed with an upright microscope (Prairie Technologies) and a water-immersion 20× objective (0.95 numerical aperture). A Mai-Tai Ti:sapphire laser (Spectra-Physics) was tuned to 870 nm and 900 nm for two-photon excitation and second harmonic generation. Images of xy sections (512×512 pixels) were acquired every 1.5-2 seconds for 5 minutes (analysis) or 10 minutes (videos) with electronic zoom varying from 1× to 3×. Emitted light and second-harmonic signals were directed through 450/80-nm, 525/50-nm and 630/120-nm bandpass filters and detected with non-descanned detectors. Files were saved as multiple TIF images and imported into FIJI (Schindelin et al., Nat Methods 9, 676-682 (2012)) for analysis or Imaris software (Bitplane) for export as videos Statistics Statistical analyses were performed using Graphpad prism 8 (LaJolla, California), STATA 13 (StataCorp. 2013. College Station, TX) and JMP10 software (SAS Institute, Inc, USA). All the data included in the studies are expressed as mean±SEM. For group analysis, one-way ANOVA with Dunnett's multiple comparison was used. If only two groups were compared, a two-tailed students t-test with Bonferoni correction was used. The statistical significance of the differences for SLE patient and SLEDAI scores was determined by a nonparametric test using Mann-Whitney analysis. Correlation was analyzed using Spearman test. *$P<0.05$ and **$P<0.005$ was considered significant.

Figure 4D:
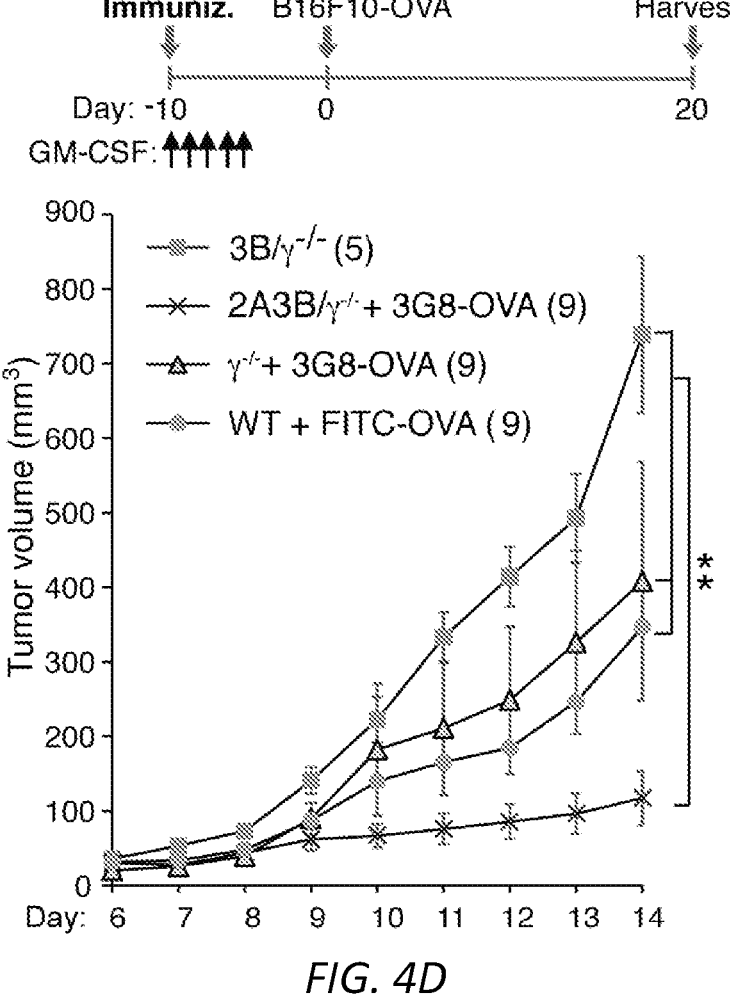

For statistical analysis of tumor growth in FIG. 4D, the change in volume over time from day 7 to day 14 was estimated in each animal controlling for group and the repeated measures of the same animal through use of a mixed-effects regression model with a random subject effect. The model considered separate intercepts and slopes for animals in each of the four groups. An additional model considered possible non-linear relationships of volume with time in each animal through inclusion of a quadratic effect in time. For estimation, this effect was centered at the mean time of 12.5 days. Models were fitted using maximum likelihood, and likelihood ratio tests were used to test whether slopes differed across groups and whether inclusion of quadratic terms improved model fit. Models were fitted using the Mixed routine in STATA version 13. A model adding the quadratic term was not significantly better than the model assuming linearity over time with separate slopes per group.

Example 1

Figures 1A, 1B:
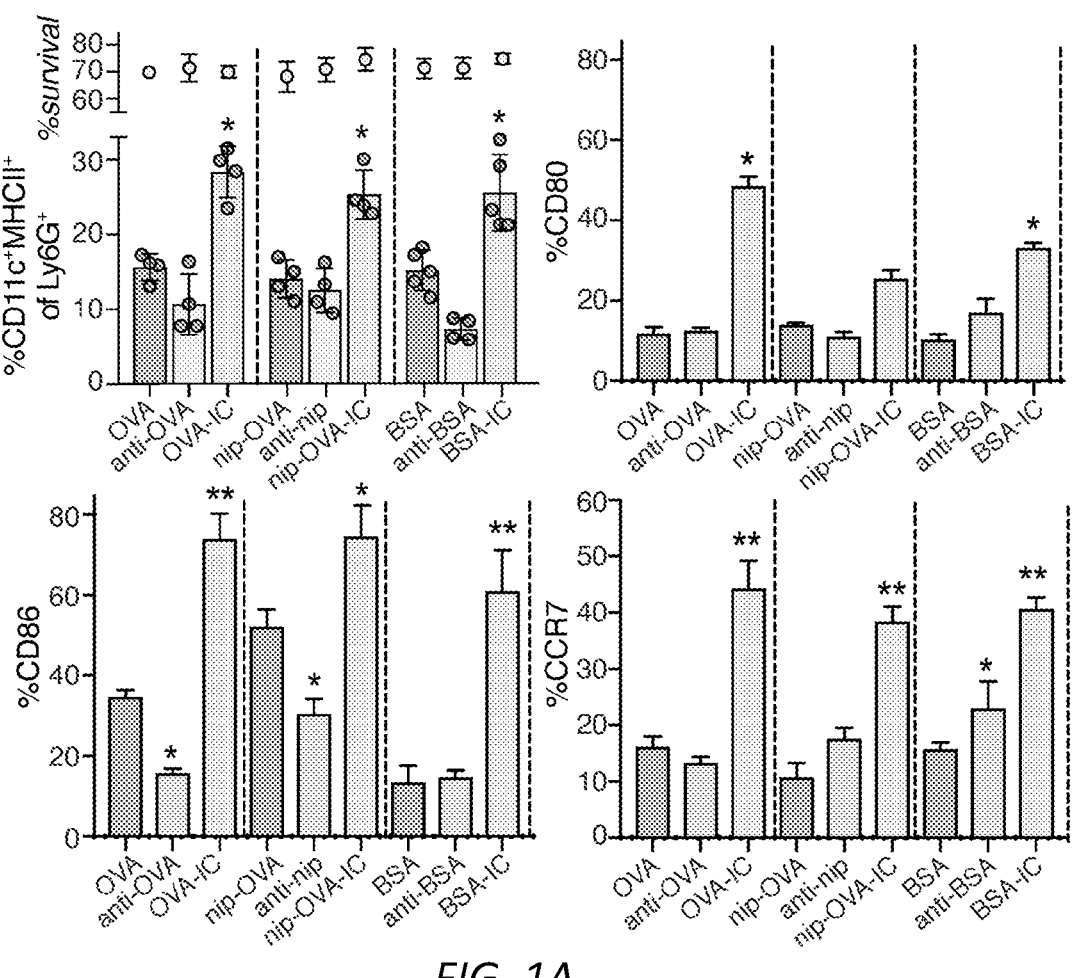
FIGS. 1A-G: FcγR engagement by immune complexes promotes neutrophil differentiation into dendritic cells. A-B) Mature neutrophils isolated from wild-type mice were incubated with indicated model immune complexes (ICs) composed of OVA-anti-OVA, Nip-OVA-anti-Nip or BSA-anti-BSA or individual components for 2 hrs, washed and cultured with GM-CSF (A), or treated with SLE patient or normal (NH) sera, or ICs generated with IgG from anti-RNP positive SLE sera and RNP (SLE-IgG+RNP) or IgG from normal sera plus RNP (NHS-IgG+RNP) and cultured in media without GM-CSF (B). After 3 days, cells were retrieved, evaluated for survival and analyzed for markers of neutrophils (Ly6G) and DCs (CD11c, MITCH) by flow cytometry. This population was analyzed for additional DC markers, CD80, CD86 and CCR7. Data is mean±s.e.m. P-values are calculated by a one-way ANOVA and Dunnett's multiple comparison test in A) and multiple t-tests in B). *P<0.05 and **P<0.005. C-D) Blood samples from normal human controls (N) and SLE patients were analyzed for the indicated neutrophil (CD10, CD15) and DC (CD11c, MHCII) markers on lineage negative (Lin−; CD3⁻CD19⁻CD56⁻) cells (C), and SLE samples were further evaluated for CD80, CCR7 and dendritic subset markers (Clec9A, CD141) (D) and correlated with clinical SLE disease activity index (SLEDAI) scores. Statistical significance was determined by a non-parametric test using Mann-Whitney analysis and correlation was analyzed by a Spearman test, *P<0.05. E) Mice with knock-in of tdTomato in the Ly6G locus were subjected to anti-GBM nephritis. At day 14, indicated tissues were isolated from naïve mice (Control) and mice subjected to anti-GBM nephritis and CD45⁺, Lin− and tdTomato positive cells were evaluated for DC markers (CD11c⁺MHCII⁺). This population was further analyzed for DC markers (middle panel) and DC subset markers (bottom panel) were additionally evaluated in mice subjected to anti-GBM nephritis. The student t-test for unpaired comparisons with Dunn-Bonferoni was used to compare the mean percentages of tdTomato⁺CD11c⁺MHCII⁺, CD86⁺ or CCR7⁺ events in control versus anti-GBM nephritic animals. *P<0.05 and P<0.005. F-G) Neutrophils from wild-type, γ⁻/⁻, FcγRIIA(2A)/γ⁻/⁻ and FcγRIIIB(3B)/γ⁻/⁻ mice were incubated with SLE ICs (F) or FcgRIIIB-antibody-antigen conjugate (3G8-OVA) (G) and analyzed as in A). Multiple t-test was used to determine significance between OVA and OVA-IC or normal (N) and SLE(S) serum, P<0.005.
Figure 1C:
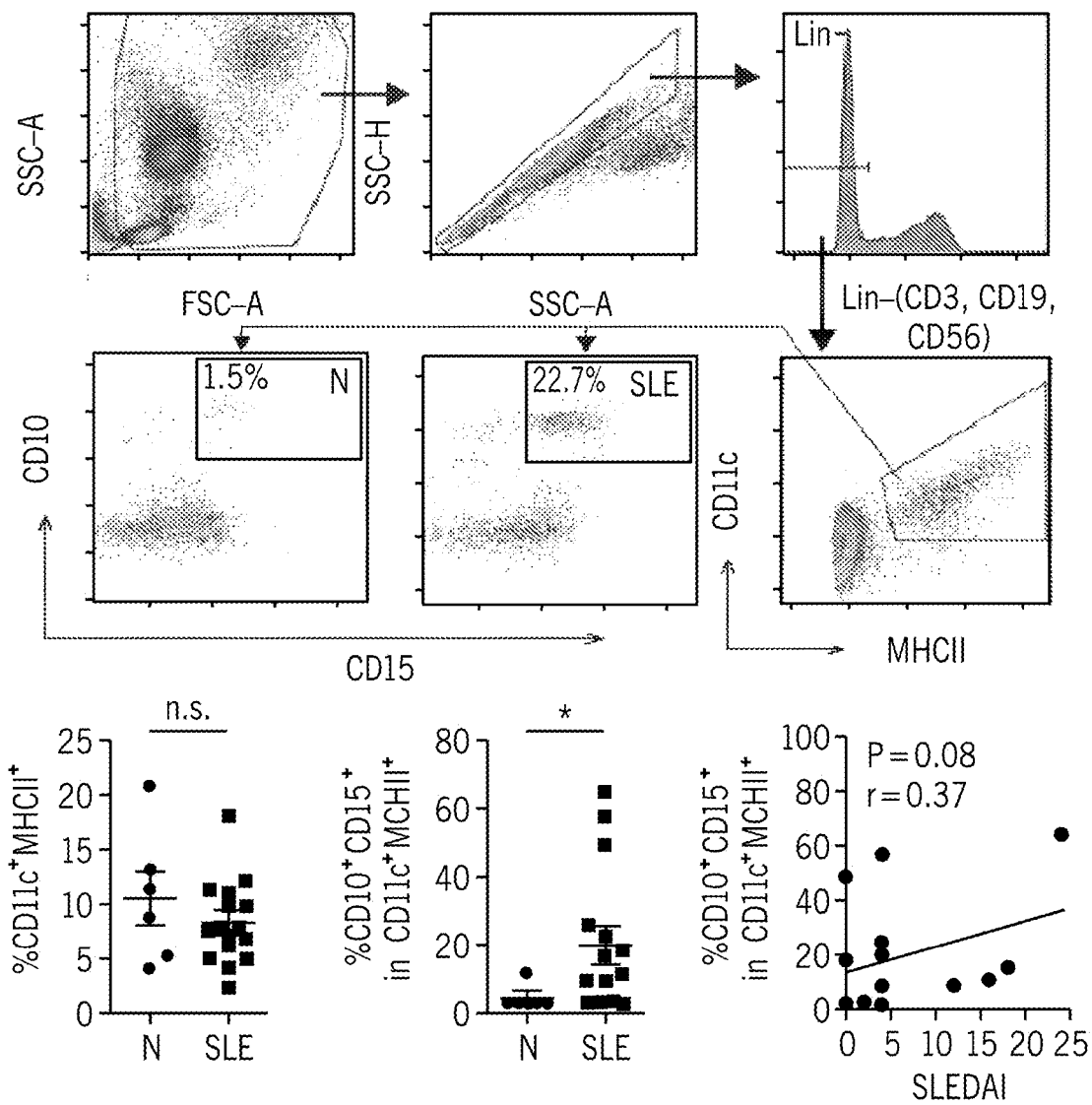
Figure 1D:
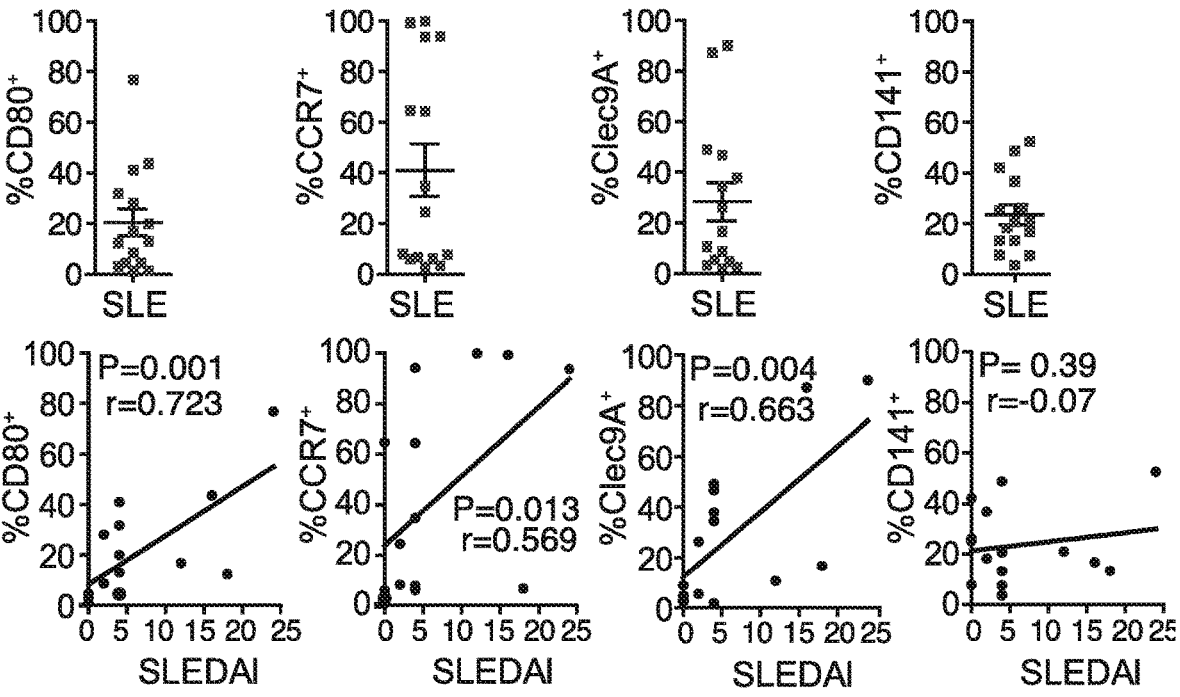
Figure 1E:
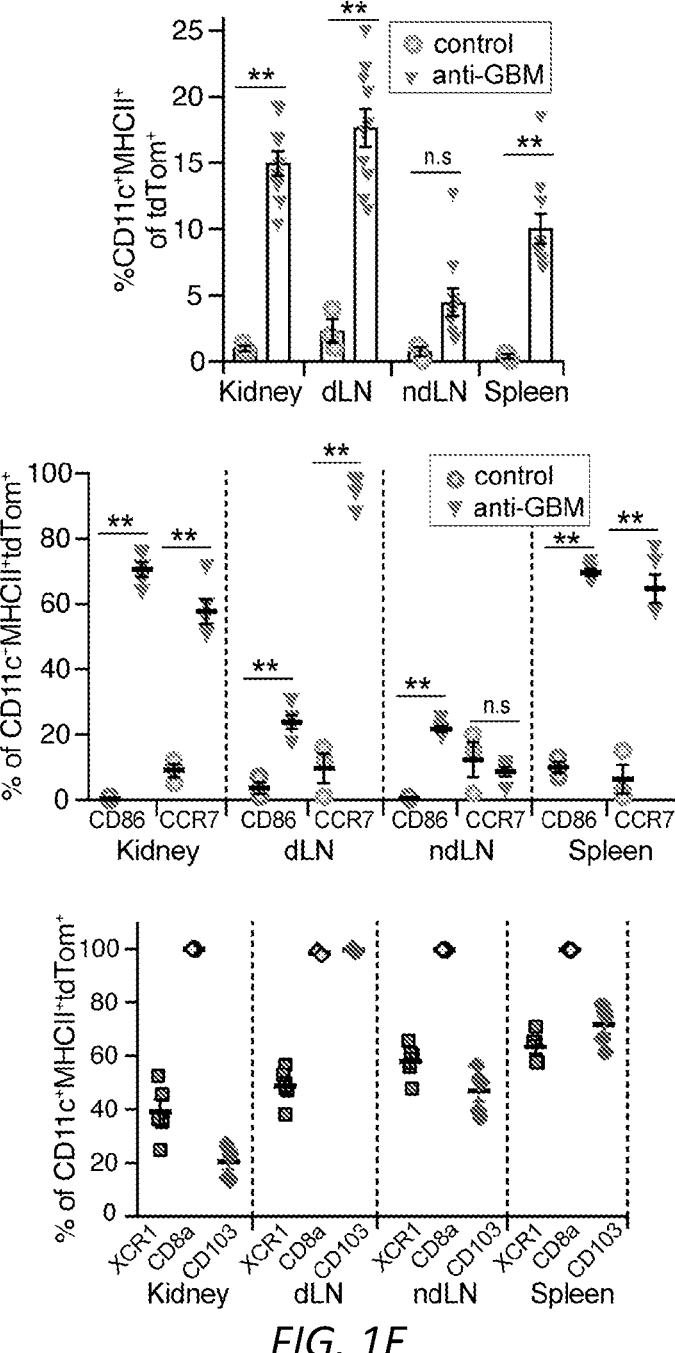
Figure 5A:
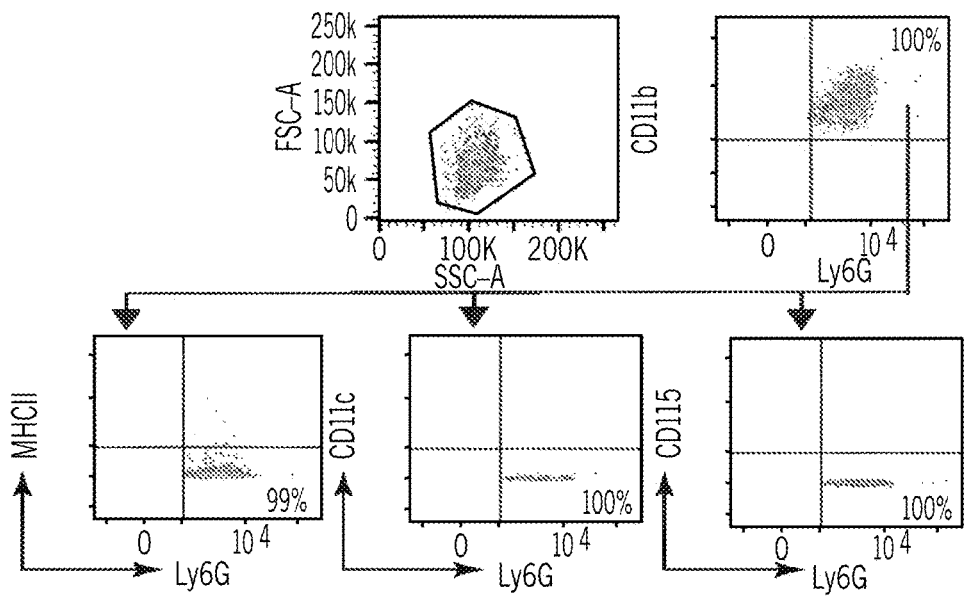
Figure 5B:
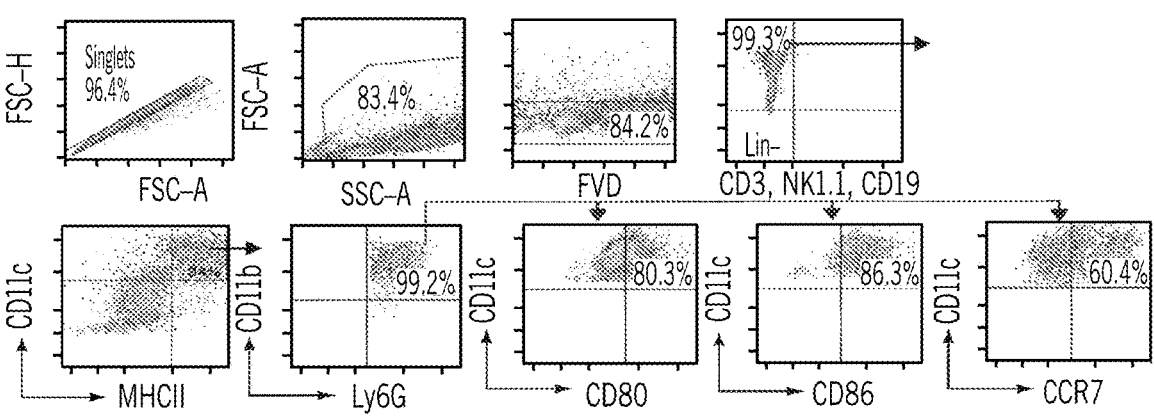
Figure 5C:
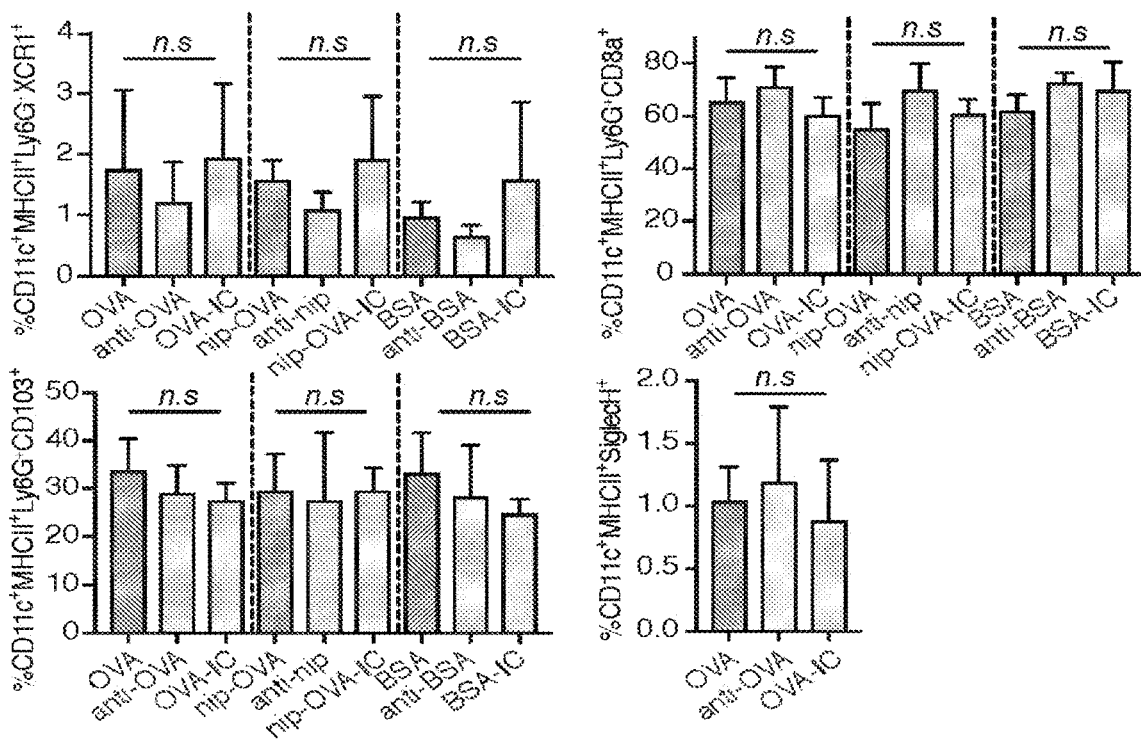
Figure 5D:
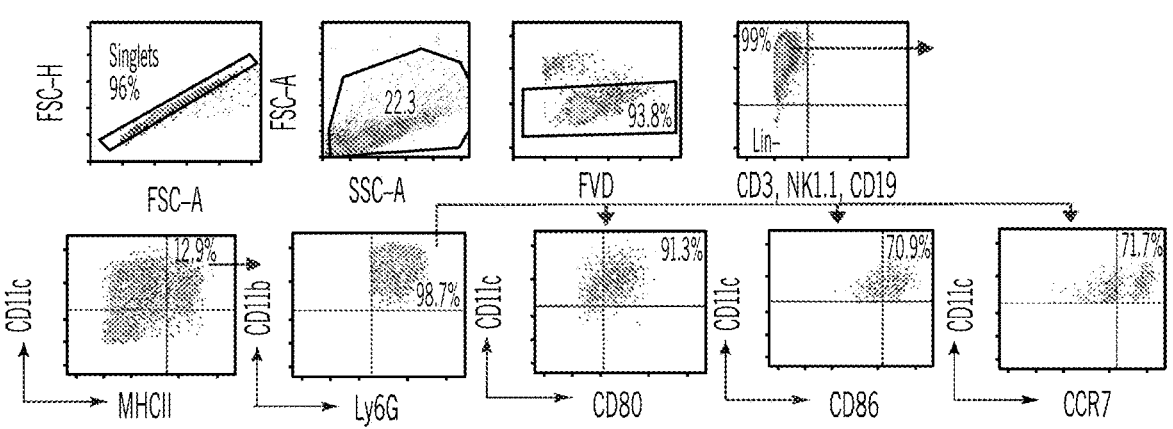
Figure 5E:
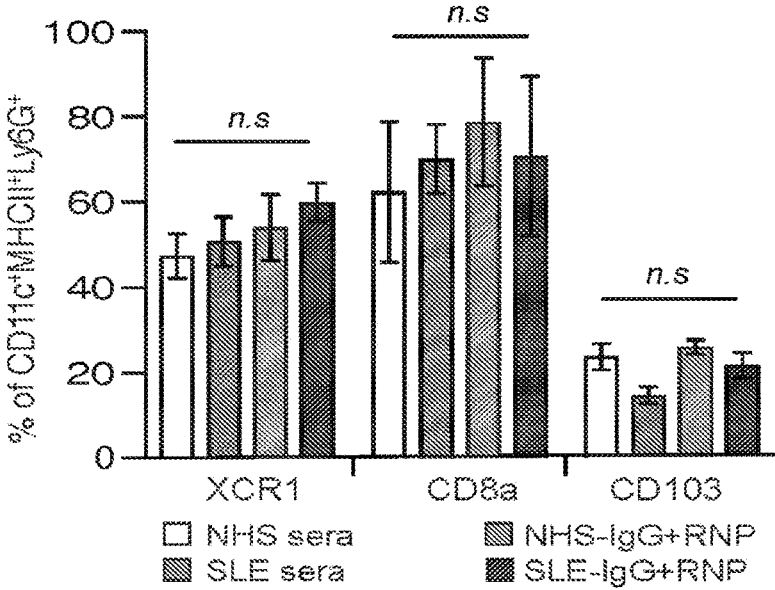
Figure 5F:
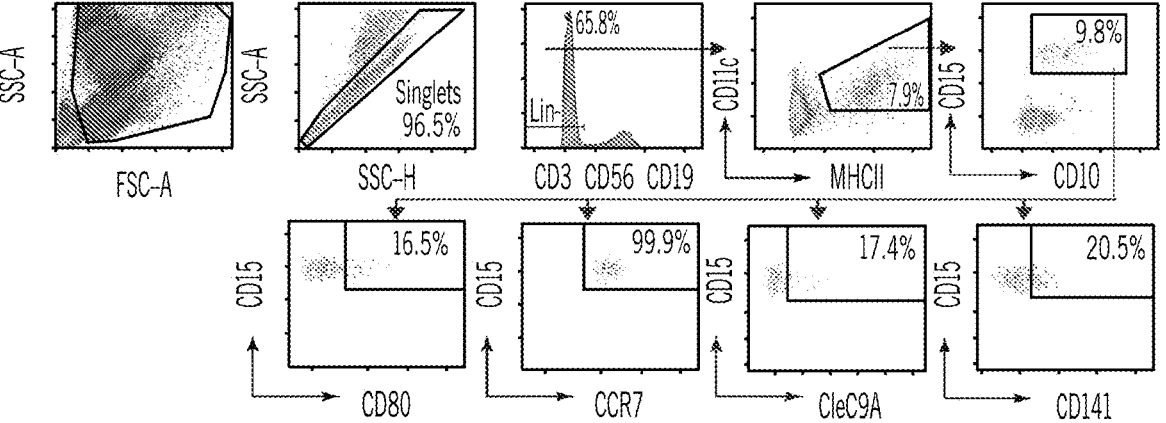

FcγRIIIB Targeted Antigen Uptake Converts Neutrophils into Immunogenic Dendritic-Like Cells As shown herein, purified murine bone marrow derived neutrophils (FIG. 5A) incubated with immune-complexes (IC) in the presence of GM-CSF assumed a phenotype similar to DCs ($CD11c^+MHCII^+$) at a significantly higher frequency than neutrophils cultured in GM-CSF alone while retaining their expression of the neutrophil marker, Ly6G (FIG. 1A and FIG. 5B). ICs also enhanced maturation, which was characterized by increased expression of co-stimulatory molecules (CD80, CD86) and CCR7 (FIG. 1A) required for optimal T cell responses and DC migration to secondary lymphoid organs, respectively[16]. XCR1, CD103 and CD8α, surface markers of the so-called DC1 subset, which is specialized to cross-present exogenous antigens to CD8 T cells[2] were detected on DCs generated in the presence of GM-CSF alone and were not further enhanced by ICs (FIG. 5C). Siglec-A, a marker of plasmacytoid DCs was not observed in any of the groups (FIG. 5C). The acquisition of DC-like features was also enhanced when murine neutrophils were incubated with ICs present in sera from patients with systemic lupus erythematosus (SLE) (FIG. 1B, FIG. 5D), an autoimmune disease with abundant circulating ICs[17], and ICs generated with IgG isolated from sera of anti-ribonucleoprotein (RNP) seropositive SLE patients and RNP. Differentiation was not observed with normal sera or IgG isolated from anti-RNP negative normal individuals plus RNP (FIG. 1B, FIG. 5E). In concordance with these findings, neutrophil-derived DCs (NDDC) that express CD11c, MHCII and the neutrophil markers CD10 and CD15 were increased in the blood of lupus patients compared to normal volunteers. The frequency of NDDC that expressed the co-stimulatory molecule CD80, CCR7 and DC subset marker Clec9A, but not CD141, correlated with lupus clinical scores (FIGS. 1C-D, FIG. 5F). In neutrophil reporter mice[18] subjected to anti-glomerular basement (anti-GBM) mediated glomerulonephritis[13] (FIG. 1E), a surrogate of lupus nephritis, NDDCs were increased in renal tissue, draining lymph nodes and spleen compared to naïve animals.

Figure 1F:
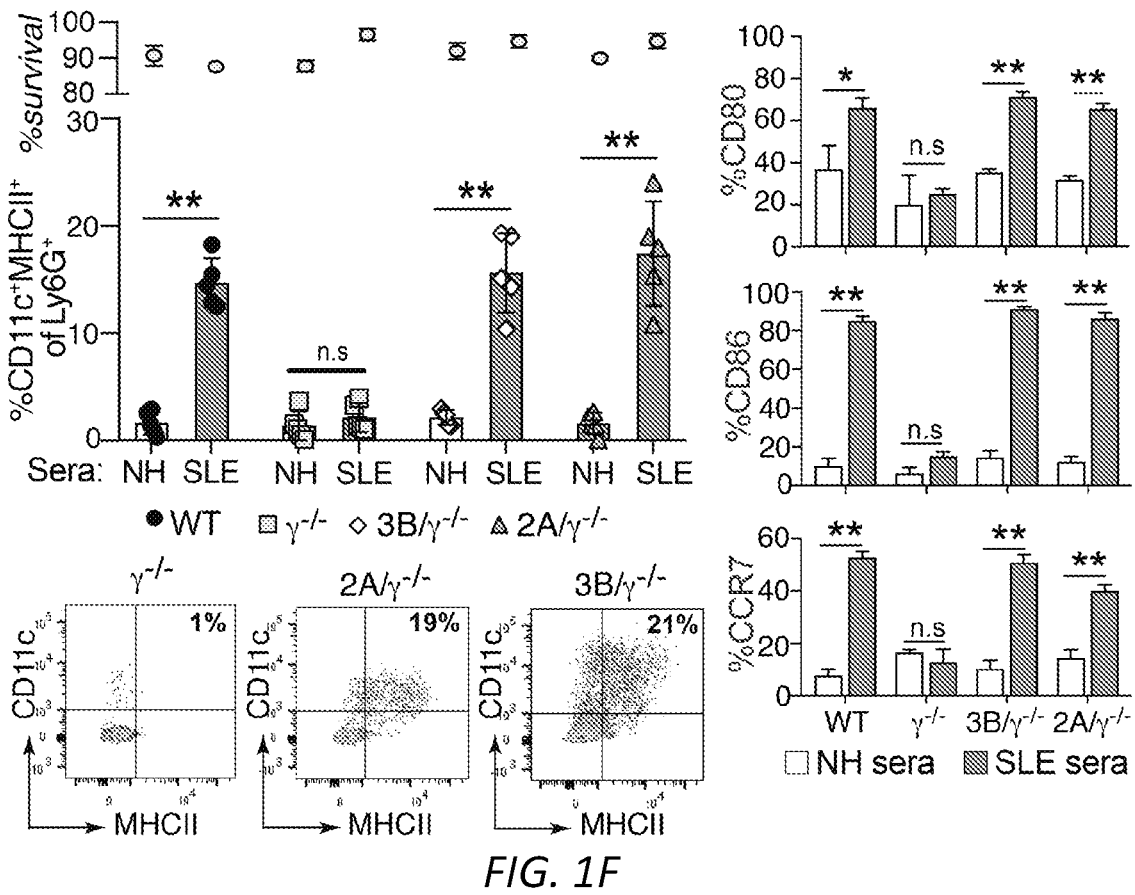
Figure 1G:
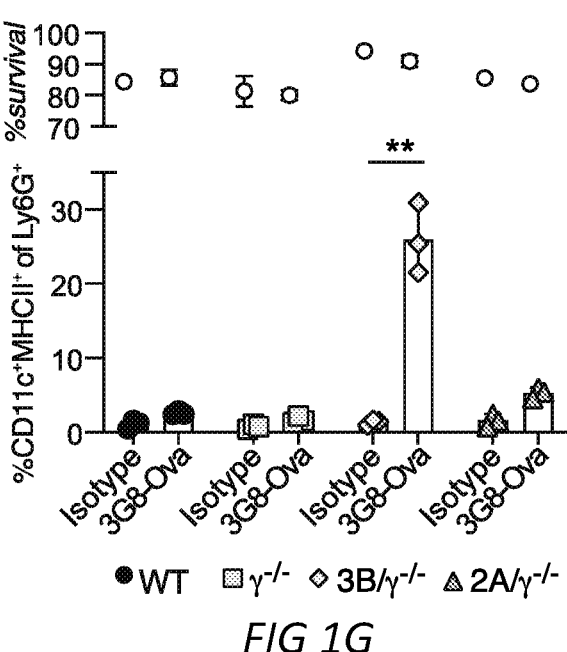
Figure 5G:
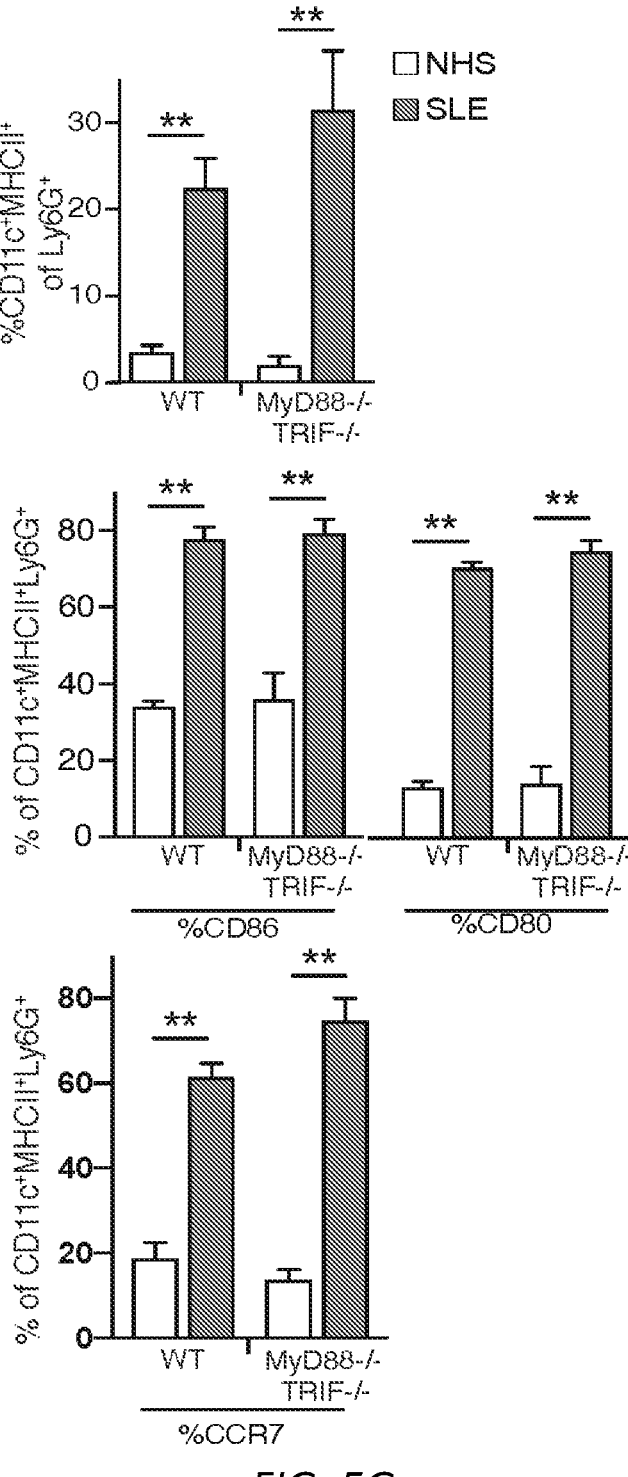

Neutrophils from FcR γ-chain deficient mice ($\gamma^{-/-}$) failed to differentiate in response to SLE serum demonstrating a requirement for activating FcγRs in the process (FIG. 1F). Notably, differentiation to NDDC was observed in neutrophils isolated from $\gamma^{-/-}$ mice expressing human FcγRIIA (FcγRIIA/$\gamma^{-/-}$) or FcγRIIIB (FcγRIIIB/$\gamma^{-/-}$) selectively on neutrophils[13] (FIG. 1F), suggesting that either of the two human activating FcγRs support neutrophil conversion into DCs. Remarkably, NDDCs remained viable for at least 9 days in culture (FIG. 1F). Anti-FcγRIIIB-OVA (vaccine) treatment of neutrophils isolated from $\gamma^{-/-}$ mice expressing human FcγRIIIB (FcγRIIIB/$\gamma^{-/-}$) converted the neutrophils to NDDCs. Similarly treated neutrophils from $\gamma^{-/-}$ mice or $\gamma^{-/-}$ mice expressing human FcγRIIA (FcγRIIA/$\gamma^{-/-}$) showed no conversion (FIG. 1G). Although adjuvants play an important role in DC maturation and sera from SLE patients are highly enriched in autoantibodies complexed to Toll-like receptor (TLR) ligands such as RNP and DNA[17], neutrophils from WT and Myd88/TRIF[-/-] mice that lack canonical and non-canonical TLR signaling[19] exhibited comparable NDDC differentiation following incubation with SLE ICs (FIG. 5G).

Figure 2A:
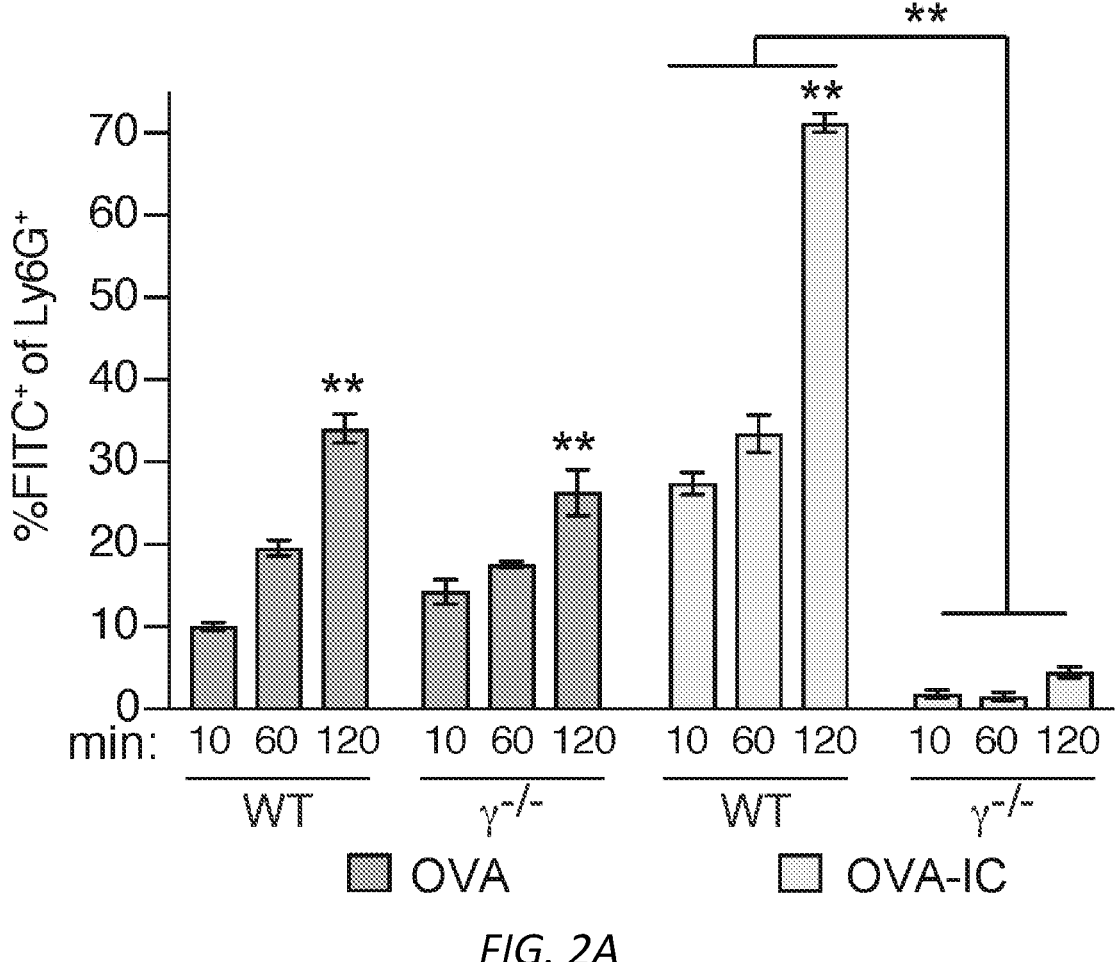
FIGS. 2A-D: Antigen uptake by neutrophil FcγRIIA or FcγRIIIB generates DCs that activate CD4 and CD8 cells. A) Isolated WT and γ⁻/⁻ neutrophils were incubated with FITC-OVA or FITC-OVA-IC for the indicated times. The FITC positive signal is a measure of FITC-OVA uptake. Mean % positive cells±s.e.m. are given. n=5 per group. Unpaired student t-test was used to compare the mean percentage of Ly6G⁺FITC⁺ events between WT and γ⁻/⁻ at different time points, **P<0.005. B-C) NDDCs were generated with GM-CSF alone (−), OVA or OVA-ICs. After 3 days in culture, adherent cells were incubated with CFSE labeled CD8 T cells, OT-I, which recognize OVA²⁵⁷⁻²⁶⁴ peptide in the context of H2Kb-MHC class I. As a positive control GM-CSF generated NDDC were pulsed with the OVA peptide SIINFEKL (SEQ ID NO: 1) (B), or CD4 Tcells, OT-II, which recognize OVA$^{323-339}$ peptide in the context of I-Ab-MHC class II (C). CFSE dye dilution represents distinct generations of proliferating cells. Graphs show mean % cells dividing±s.e.m. One way ANOVA with Dunnett multiple comparisons was used to compare the mean percentages of GM-CSF (–), OVA and OVA-ICs in different genotypes as indicated. *P<0.05 and **P<0.005. D) Neutrophils isolated from MyD88/TRIF–/– mice were treated as in B-C and OTI and OTII proliferation were evaluated (n=2).
Figure 2B:
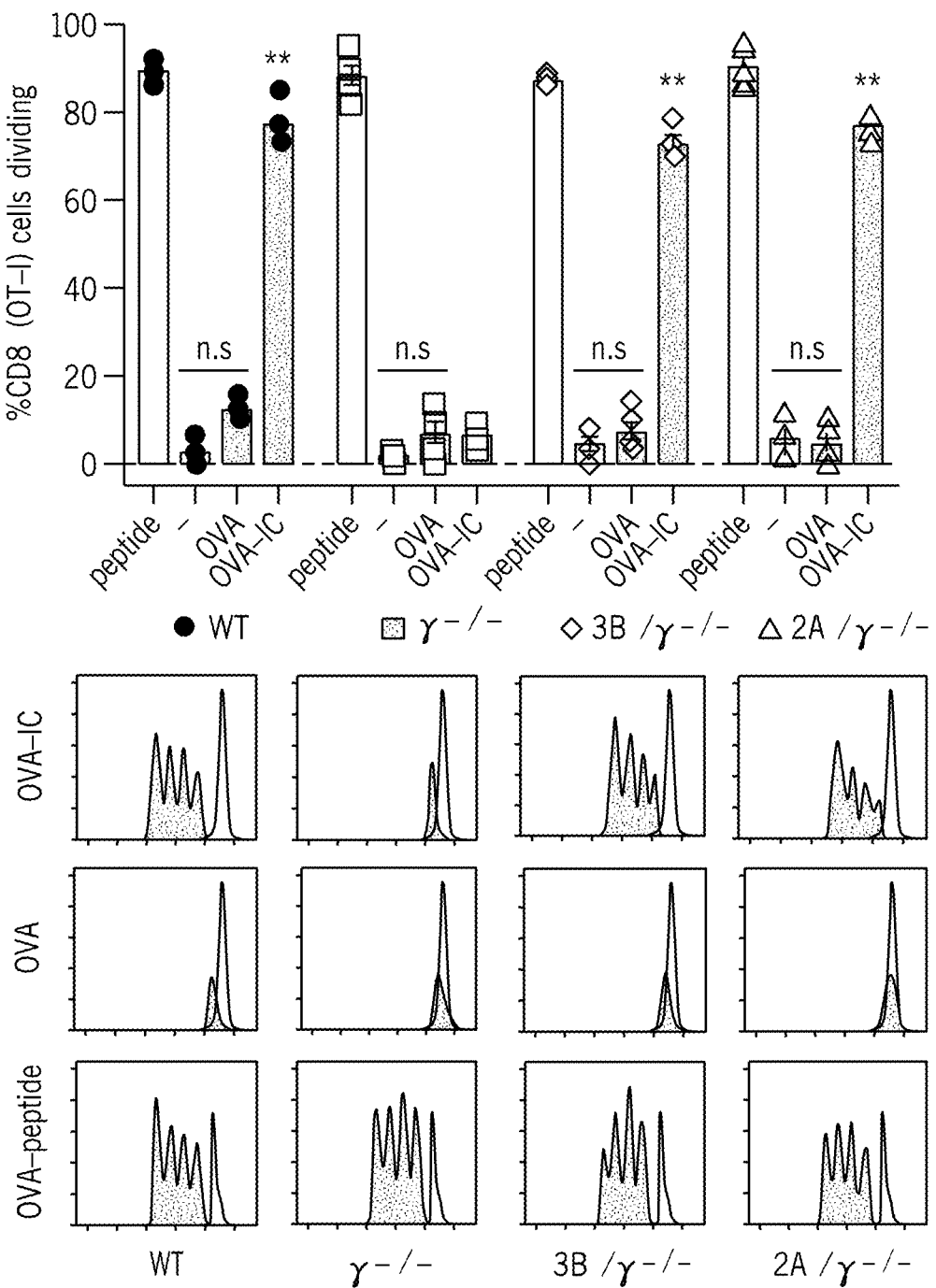
Figure 2C:
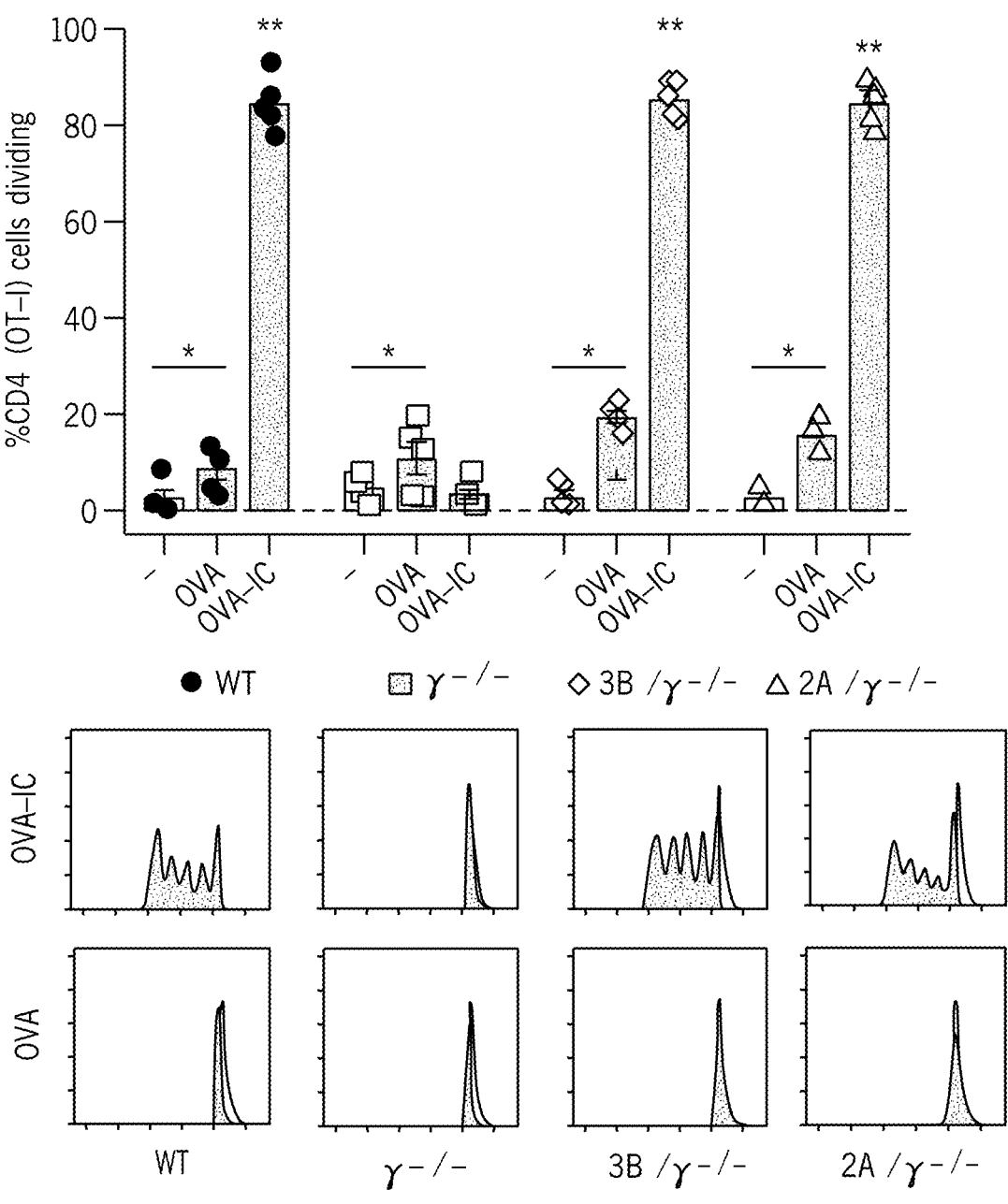
Figure 2D:
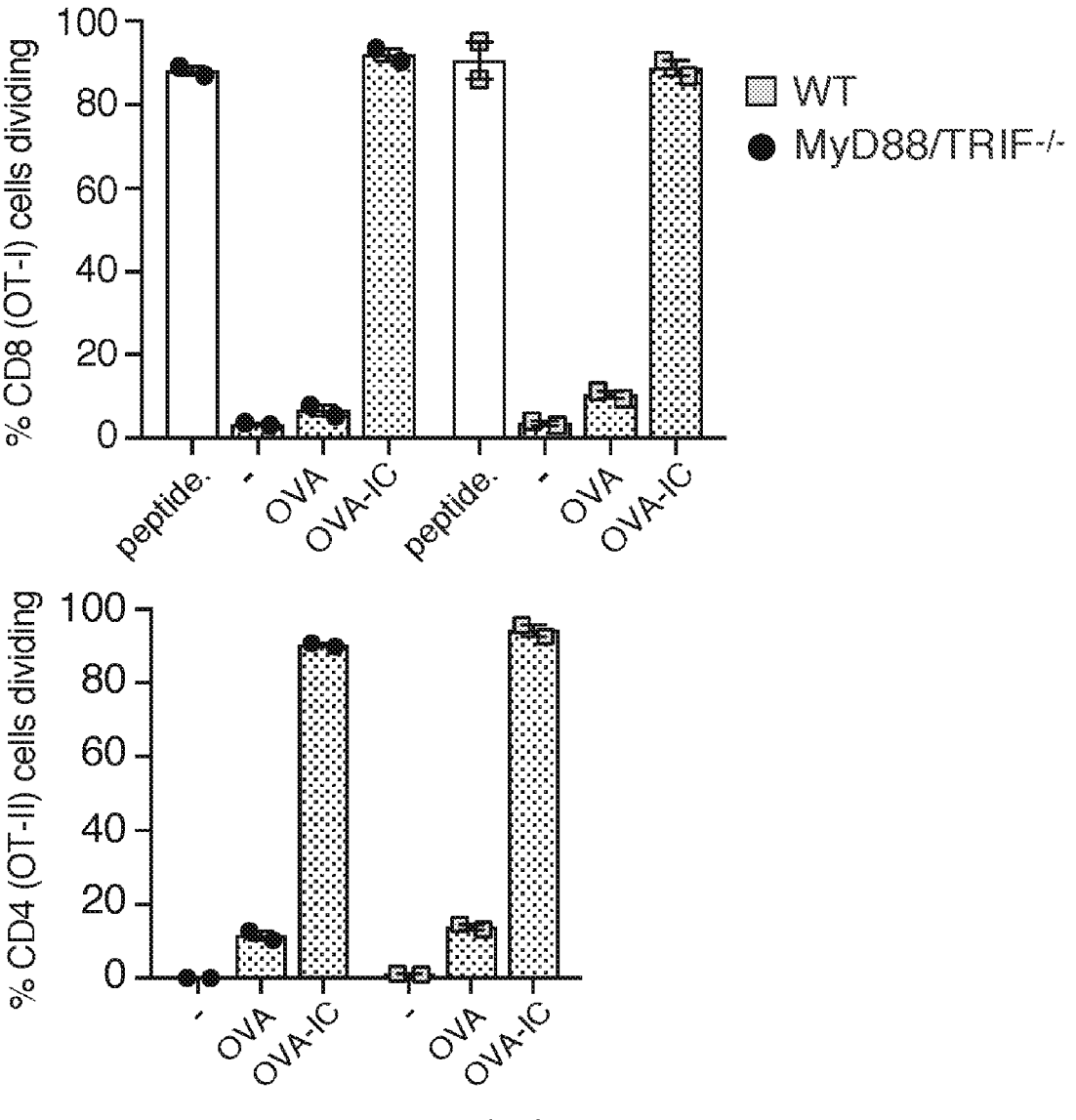

Classical DC activation of naïve CD8 T cells requires several fold lower concentrations of antigen in ICs than soluble antigen[2, 20, 21]. This correlates with antigen trafficking into specific early or late endosomes versus degradative lysosomes rather than the amount of antigen internalized[2, 22, 23]. Neutrophil uptake of OVA in ICs was enhanced 2-fold compared to soluble OVA after two hours of incubation and this was FcγR dependent (FIG. 2A). NDDCs derived from neutrophils fed OVA-IC exhibited a robust capacity to cross-prime OVA-specific CD8 T cells, while those from neutrophils fed soluble OVA failed to do so (FIG. 2B). Neutrophils from mice deficient in β2 microglobulin, required for MHCI expression on the surface, failed to activate CD8 T cells (FIG. 6). NDDCs derived from neutrophils fed OVA-IC also robustly activated naïve CD4 T cells and these were more effective than those derived from neutrophils fed soluble OVA (FIG. 2C). DCs differentiated from $\gamma^{-/-}$ neutrophils were defective in OVA-IC dependent activation of CD4 and CD8 T cells while the same directly loaded with OVA peptide exhibited normal CD8 T cell proliferation. NDDCs from $\gamma^{-/-}$ neutrophils expressing either FcγRIIA or FcγRIIIB supported activation of both T cell subsets (FIGS. 2B-C). TLRs were not required as T cell proliferation was similar in DCs originated from OVA-IC loaded WT and MyD88/TRIF[-/-] neutrophils (FIG. 2D).

Figure 3A:
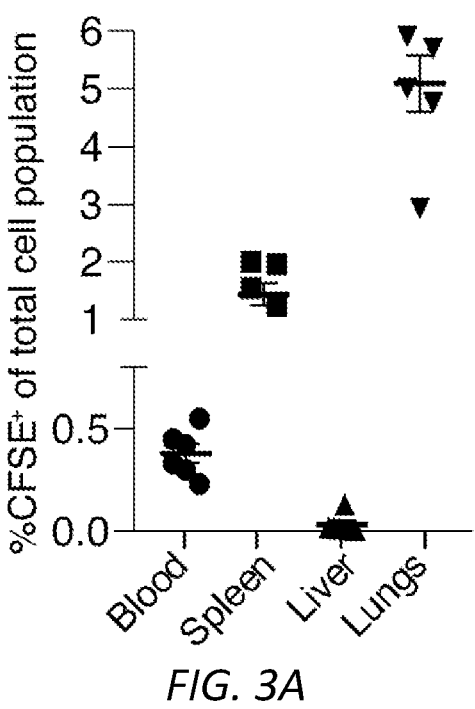
FIGS. 3A-E: Neutrophil derived DCs are migratory and promote an antigen dependent delayed type hypersensitivity response and B16F10 tumor immunity. OVA-IC or OVA-fed neutrophils from wild-type (A, C-E) or β-actin-RFP (B) mice were cultured ex vivo to generate NDDC. A) NDDCs were CFSE labeled and injected i.v. at day –3. At day 0, their presence in blood, spleen, liver and lung was determined by flow cytometry. B) Mice were injected with OVA-IC β-actin-RFP$^+$ NDDC in the footpad at day –7 and at day 0, intravital microscopy was performed on the popliteal lymph node. Dwell time in seconds, the number of OT-I cells in field of view (FOV) in the presence or absence of NDDC and the number of OT-I cells interacting with RFP$^+$-NDDC was evaluated. Data was averaged from three fields of view per mouse, n=3 mice, *P<0.05, **P<0.005. Representative images of the clustering of OT-I-GFP CD8$^+$ T cells around NDDC and random distribution of CD8$^+$ T cells in areas without NDDC are shown. Scale bar: 15 uM. C) OVA or OVA-IC generated NDDC were injected i.v. day –7. On day 0, soluble OVA (+) or PBS (–) was injected in right or left footpad, respectively. On day 1, footpad swelling was evaluated in both footpads and feet were harvested for histological analysis. Inflammation scores are shown in the right panel. Unpaired student t-test was used to compare the mean percentages of footpad thickness and inflammation scores. Significance was assessed by t-test, *P<0.05 and **P<0.005. D) NDDCs (no OVA), or NDDC loaded with OVA or OVA-IC from WT or MyD88-TRIF$^{-/-}$ were injected i.v. on day –7. B16F10-0VA cells were implanted s.c. at day 0 and tumor volumes were measured over time. The number of mice per group is in parenthesis. One way ANOVA was used for the data comparison of tumor volume in OVA-IC versus all other groups, *P<0.05 and P<0.01. At harvest, OVA peptide-specific CD8 T cells in the spleen (top) and draining lymph nodes (bottom) of OVA (left) and OVA-IC (right) groups were quantitated by FACs using OVA-peptide tetrameric complexes. Mean±s.e.m. Unpaired student t-test was used to compare OVA versus OVA-IC samples. P<0.01. E) Recipient WT mice were injected with OVA-IC loaded NDDCs i.v. and B16F10-0VA s.c. as in D) and subjected to treatments with anti-CD4 or anti-CD8 depleting antibodies or isotype control as depicted in the time line. Tumor growth was assessed over time. Number of mice per group is in parenthesis. The tumor volume was compared between anti-CD8 and anti-CD4 or isotype using one way ANOVA, *P<0.05 and P<0.01. CD8 and CD4 T cell depletion was confirmed by FACs analysis of blood samples (right panels). Unpaired student t-test was performed and compared to isotype, P<0.01.
Figure 3B:
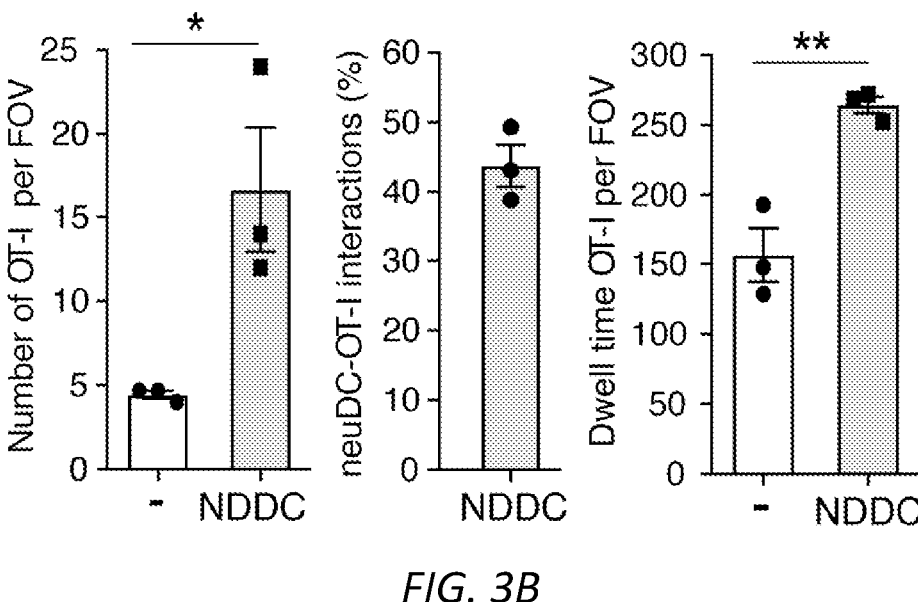
Figure 3C:
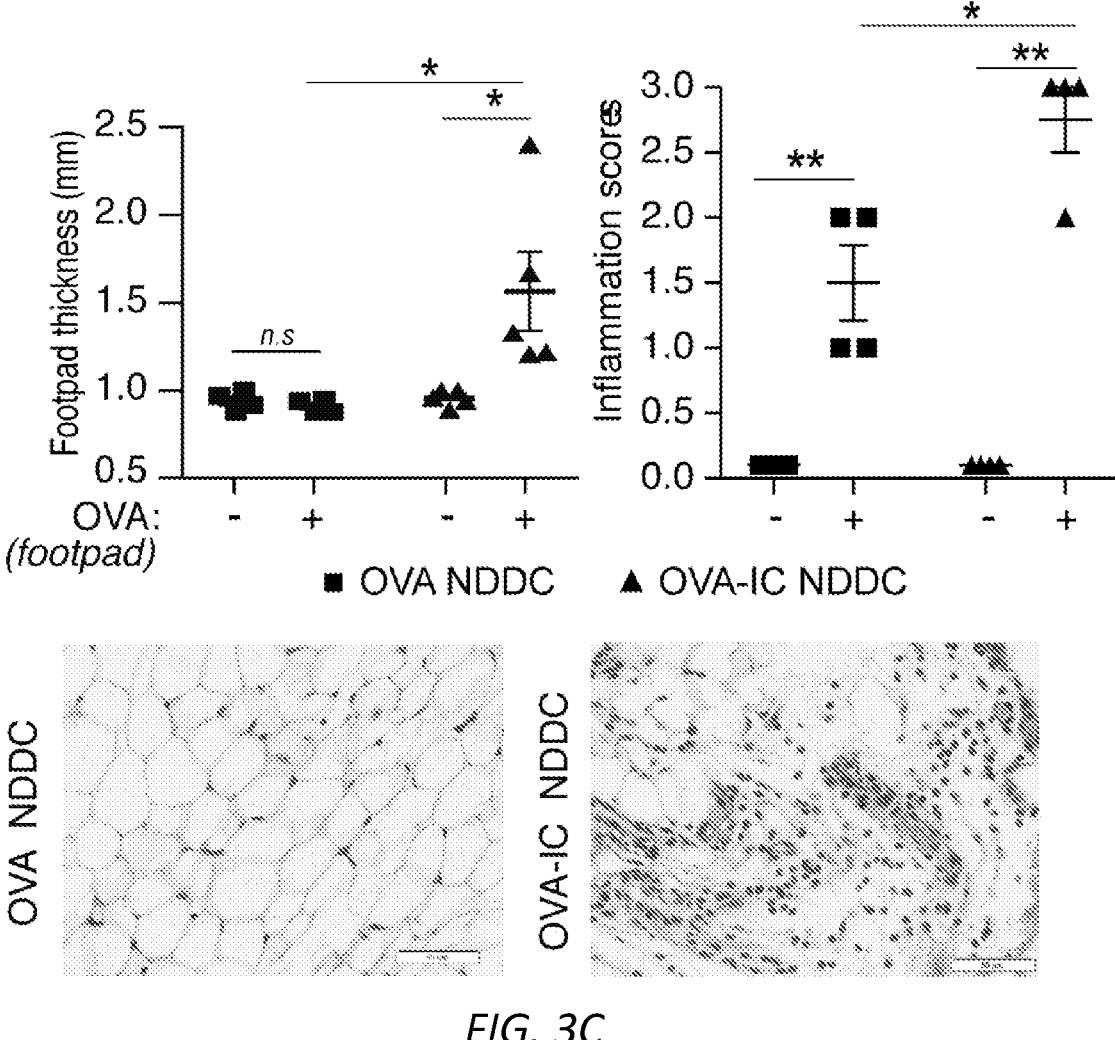
Figure 3D:
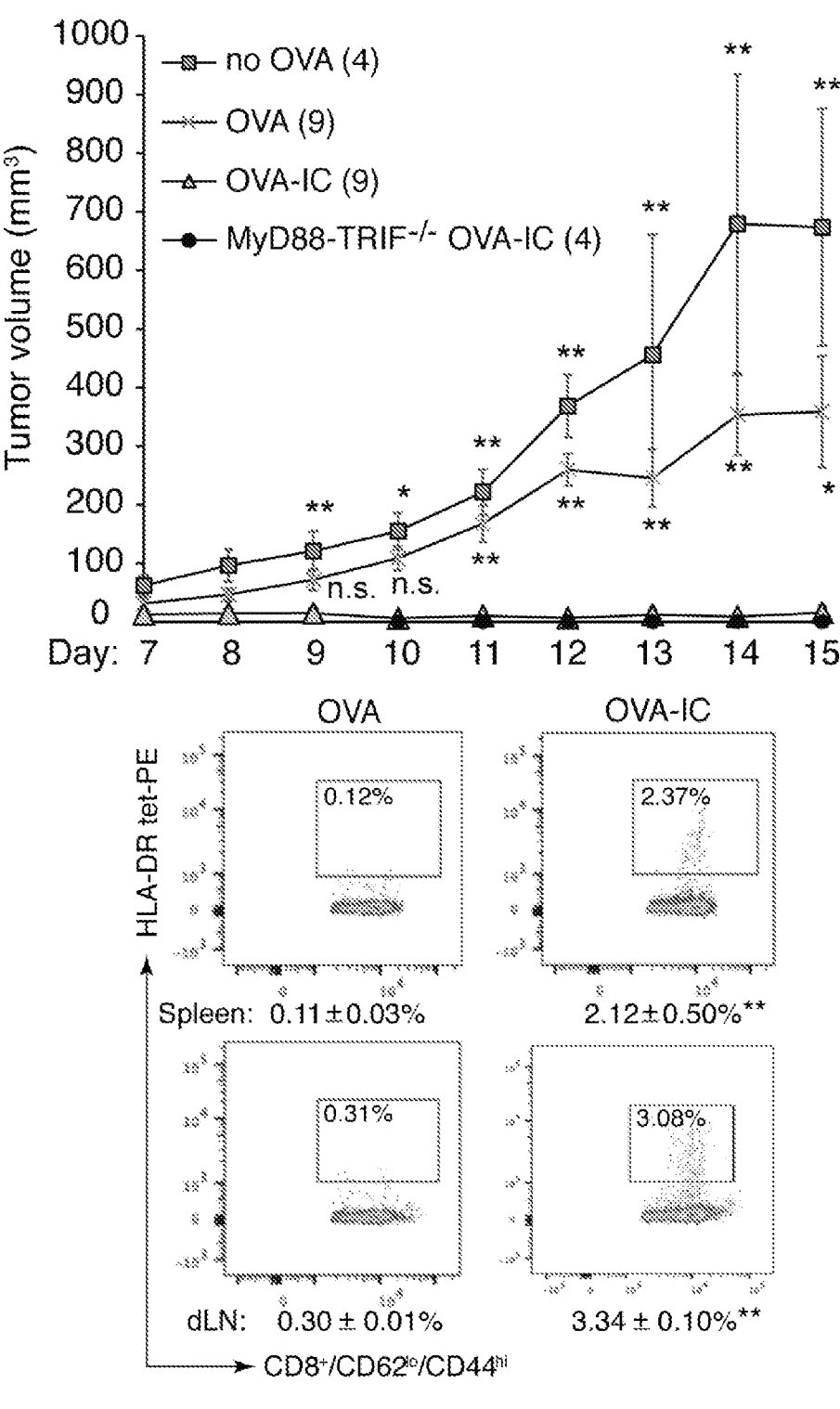
Figure 3E:
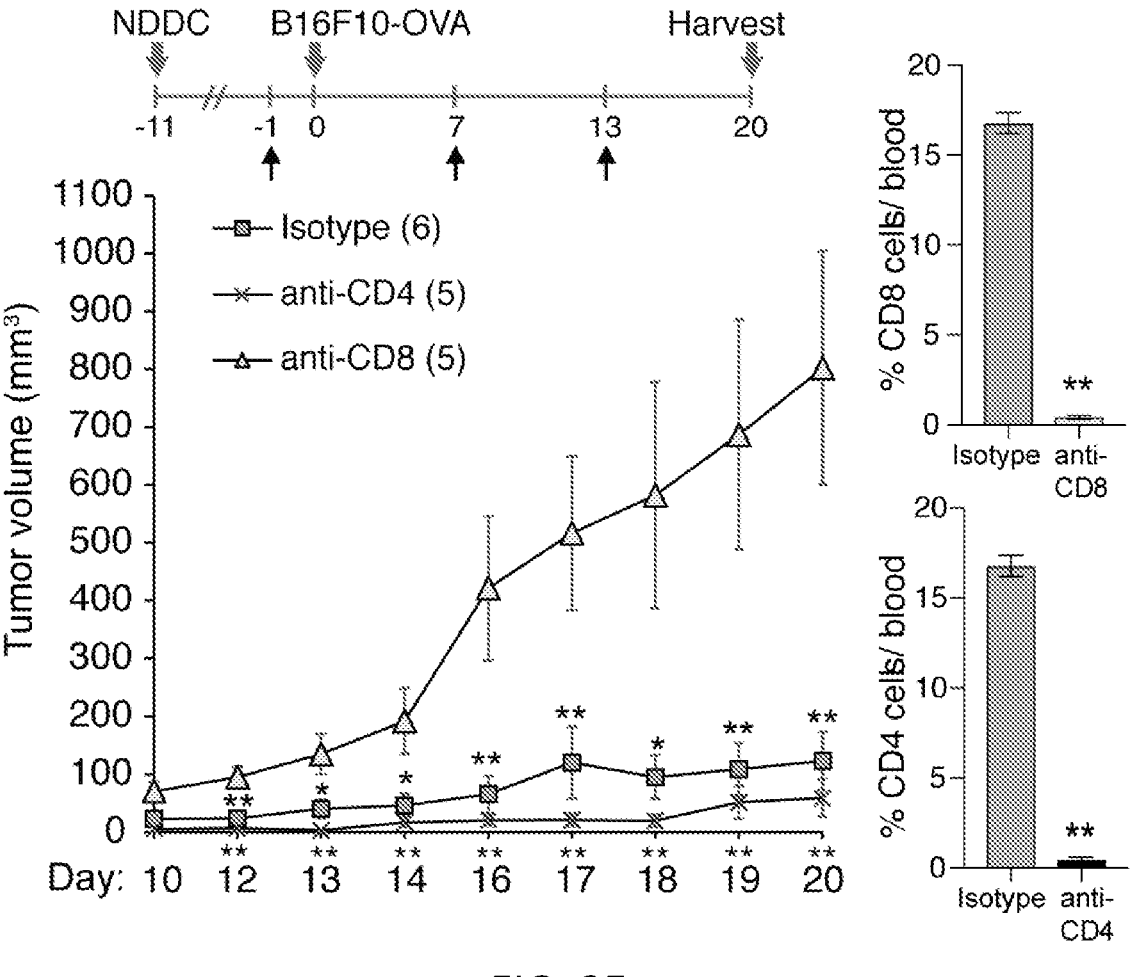

Capture of blood borne antigens by DCs in the spleen, and migration of antigen-loaded DCs from tissues into lymph nodes are both critical for initiation of T cell-mediated immune responses[16]. Intravenously injected NDDCs generated ex vivo from OVA-IC generated neutrophils accumulated in the spleen and lung (FIG. 3A), as has been described in melanoma patients injected intravenously with autologous DCs[24]. Furthermore, OVA-IC generated NDDCs injected locally into the footpad of mice accumulated in the draining popliteal LN where they displayed active dendrite extensions and prolonged contacts with CD8$^+$ T cells (FIG. 3B). Thus, OVA-IC generated NDDCs exhibited the capacity to accumulate in secondary lymphoid organs where they activate T cell function. Indeed, OVA-IC generated NDDCs were active in a delayed type hypersensitivity (DTH) model[25], which has been reported to rely on a CD4 Th1-driven recall response to antigen and subsequent neutrophil-rich inflammatory response[26]. That is, mice receiving OVA-IC generated NDDCs i.v. followed 7 days later by soluble OVA subcutaneously in the footpad developed tissue swelling and immune cell infiltration. Notably, this exceeded the response observed in mice given OVA generated NDDCs (FIG. 3C). OVA-IC generated NDDC were also effective in eliciting a CD8 T cell response, which is critical for tumor immunity. Following the subcutaneous implantation of B16F10 melanoma cells expressing OVA[27], mice prophylactically immunized with OVA generated NDDCs developed large tumors with volumes that were slightly reduced compared to mice receiving no OVA immunization (FIG. 3D). In contrast, tumor growth was completely inhibited in mice given OVA-IC generated NDDC (FIG. 3D). The anti-tumor response in the latter was associated with the accumulation of OVA specific CD8$^+$ T cells in the spleen and draining lymph node (FIG. 3D). Tumor growth in immunized mice was dependent solely on CD8 and not CD4 T cells as assessed with immunodepleting antibodies (FIG. 3E).

Figure 4E:
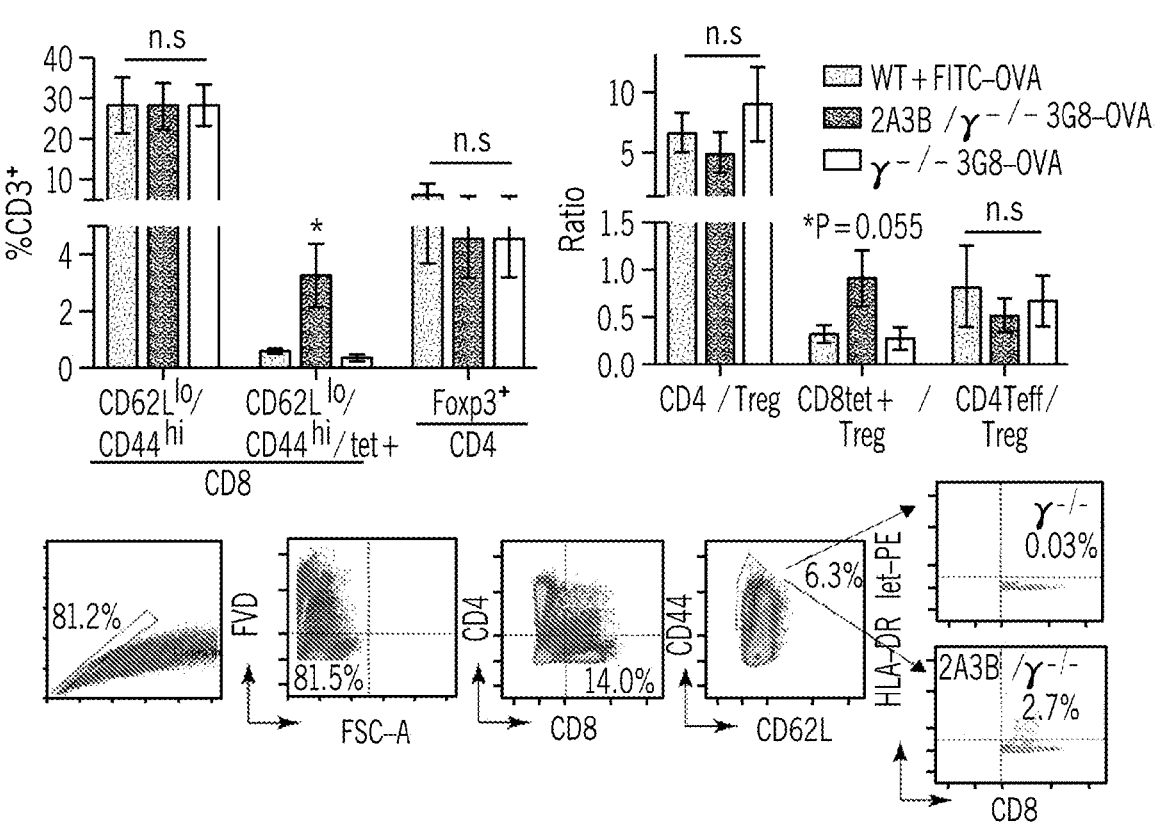
Figure 4F:
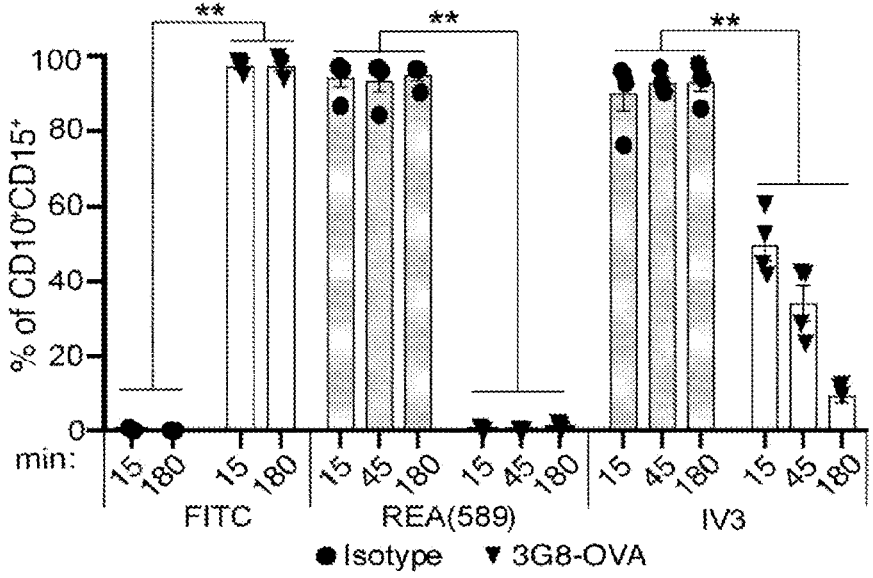
Figure 4G:
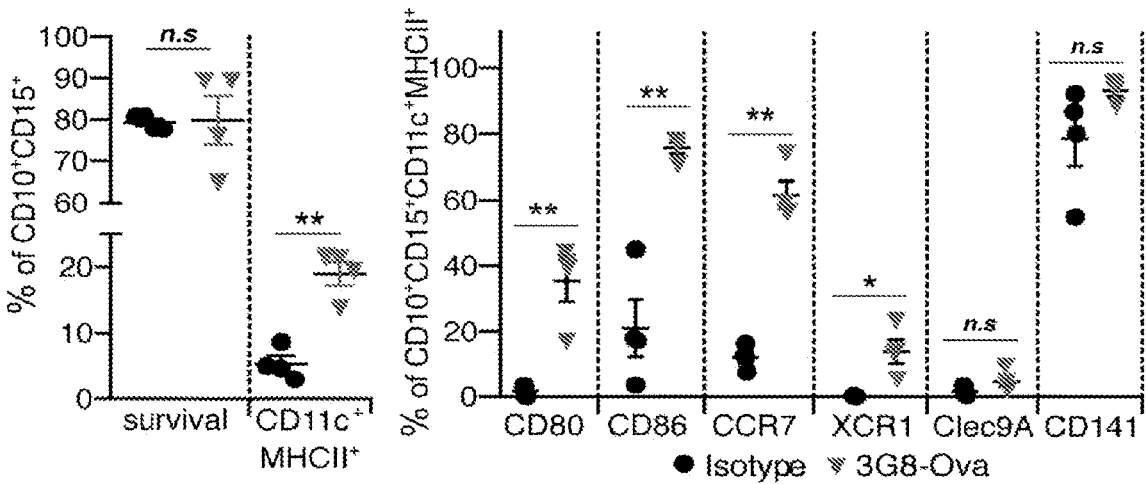
Figure 7A:
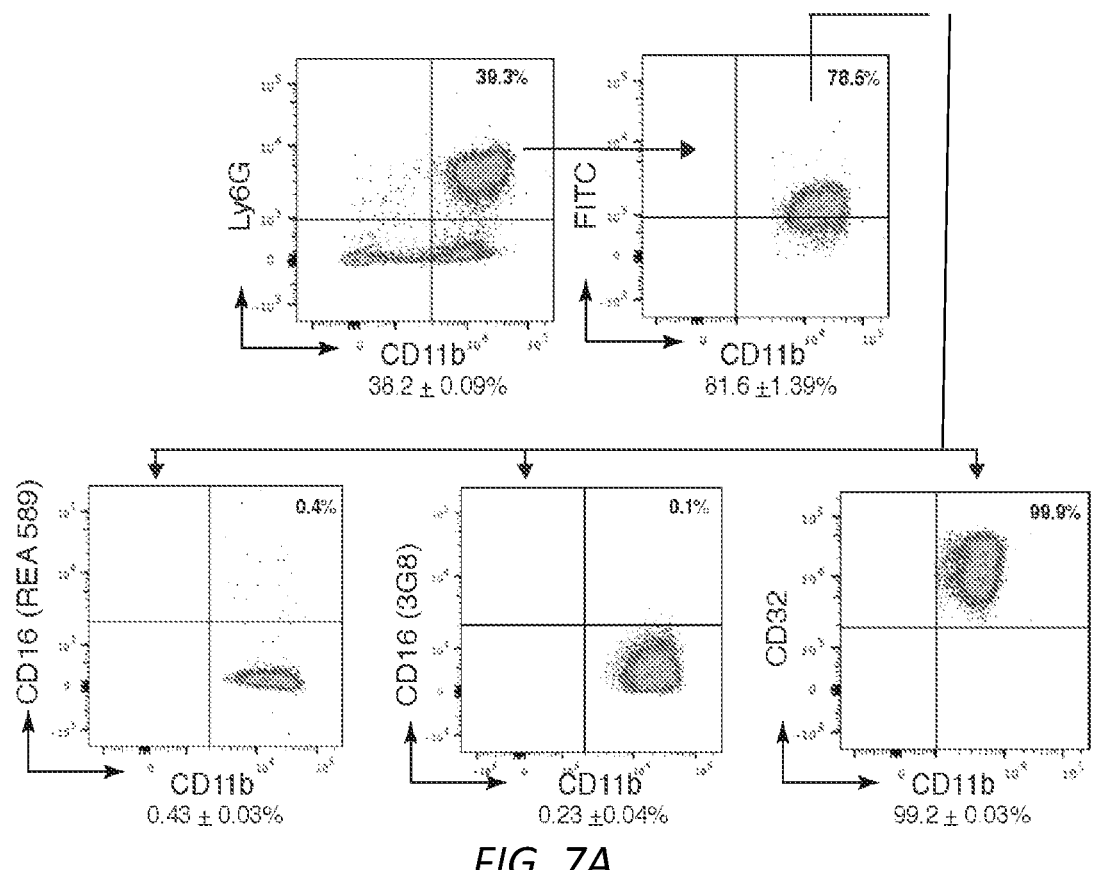
Figure 7B:
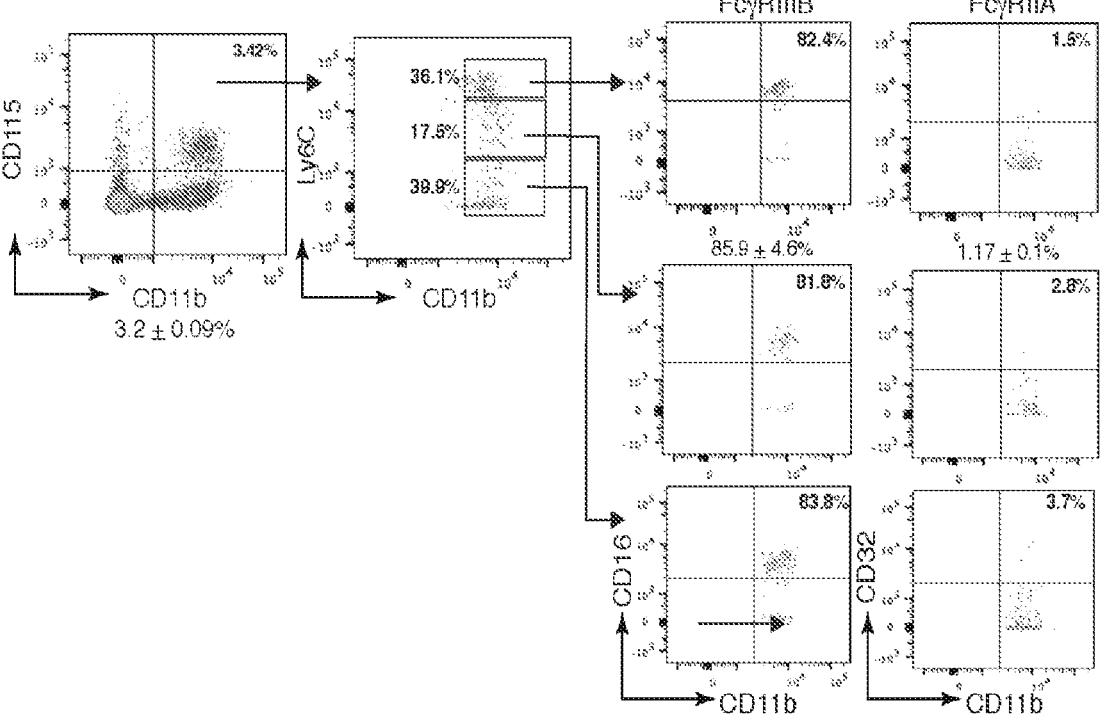
Figure 7C:
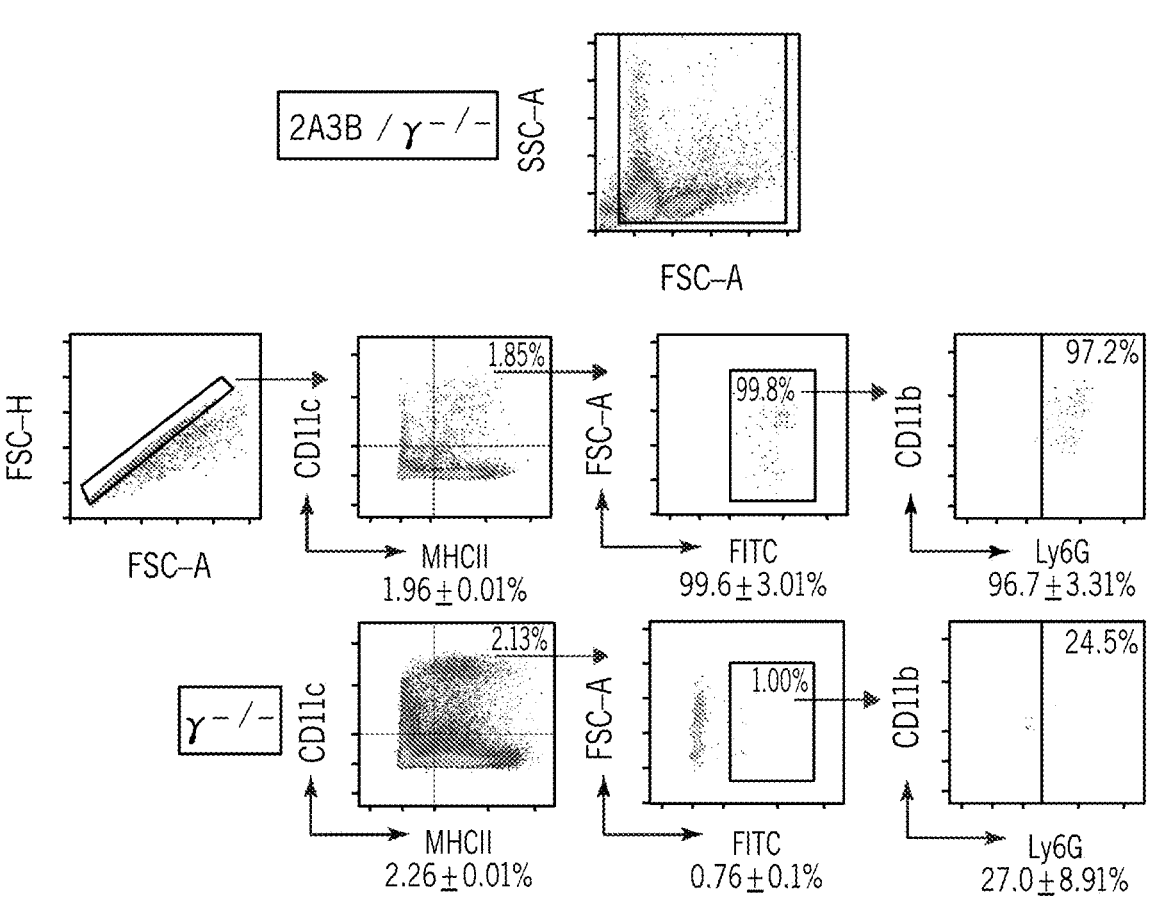
Figure 7D:
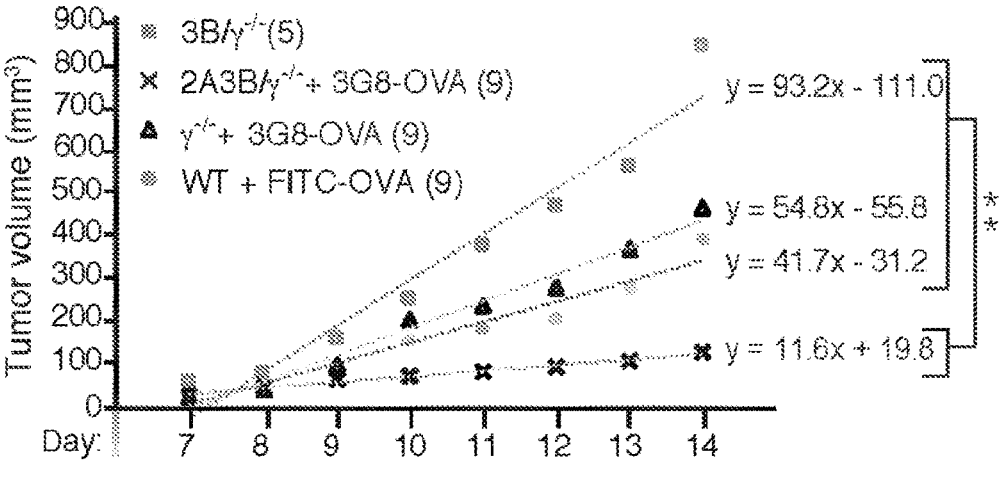

Antigen conjugated to antibody that targets endocytic receptors on classical, monocyte derived DCs can induce antigen specific T cell responses and immunity in mice when combined with TLRs[1]. We reasoned that targeting FcγRIIIB on blood neutrophils would deliver DC differentiation signals specifically to neutrophils to both generate large numbers of antigen-presenting cells and deliver antigen via an FcγR that promotes antigen cross-presentation. A single intravenous injection of FITC-OVA conjugated to the FcγRIIIB antibody, 3G8 (3G8-OVA), a mouse IgG1 with an expected half-life of 6-8 days[28] into FcγRIIIB/$\gamma^{-/-}$ and FcγRIIIB+FcγRIIA/$\gamma^{-/-}$ mice resulted in the selective labeling of neutrophils in the blood (FIG. 4A). Analysis of blood within 3.5 hrs of 3G8-OVA injection revealed internalization of the conjugate and FcγRIIIB in neutrophils as assessed by evaluating surface levels of the receptor, while FcγRIIA remained at the surface (FIG. 7A). Within 24 hrs, Ly6G$^+$ cells that expressed CD11c and MHCII, co-stimulatory markers and CCR7 were detected in the blood while 3G8-OVA labelling and DC differentiation markers were not observed in similarly treated $\gamma^{-/-}$ mice (FIG. 4A). 3G8-OVA conjugate also resulted in NDDCs in the spleen, assessed 72 hrs after i.v. injection (FIG. 4A). In humanized transgenic mice, FcγRIIIB and FcγRIIA expressed downstream of the MRP8 promoter was detected on a proportion of CD115$^+$ monocytes[13] that are also Ly6C$^+$ (FIG. 7B). However, >98% of 3G8-OVA positive CD11c$^+$MHCII$^+$ cells in the spleen expressed Ly6G suggesting that they were primarily NDDCs (FIG. 7C) These in vivo generated splenic NDDCs promoted the proliferation of OVA-specific CD8 T cells (FIG. 4B) and antigen-specific target cell killing[29] (FIG. 4C). Next, the ability of 3G8-OVA to promote anti-tumor immunity was tested. 3G8-OVA pre-immunization alone had no effect on growth of a subcutaneously implanted B16F10-OVA melanoma cells but did generate OVA-specific CD8 T cells in the tumor draining lymph node and spleen. Given the anti-tumorigenic capacity of ex vivo generated OVA-IC loaded neutrophils cultured with GM-CSF (FIG. 3D), and the success of GM-CSF-based vaccines[30] we treated mice i.v. with recombinant GM-CSF for five consecutive days that began on the day of 3G8-OVA immunization. We found that GM-CSF rendered the B16F10-OVA tumor responsive to the 3G8-OVA conjugate (FIG. 4D, FIG. 7D) that correlated with the generation of OVA-specific CD8 effector T cells, an increase of the CD8 to Treg ratio in the spleen (FIG. 4E, FIG. 7E) and enhanced CD8 T cell infiltration in the tumor compared to wild-type mice immunized with OVA alone or $\gamma^{-/-}$ mice immunized with 3G8-OVA. These findings with 3G8-OVA may have relevance in humans as peripheral blood human neutrophils treated with the conjugate rapidly internalized OVA and the targeted Fc$\gamma$RIIIB Fc$\gamma$RIIA internalization was also observed over time (FIG. 4F) and may be important for optimal generation of NDDC as discussed in the section below. This differs from the lack of Fc$\gamma$RIIA internalization in mice 3 hrs after 3G8-OVA administration (FIG. 7A). It is possible that Fc$\gamma$RIIA internalization in vivo may occur over a longer time period. Within 2 days of culture, neutrophils given 3G8-OVA had significantly greater expression of CD11c, MHCII, co-stimulatory molecules and CCR7 compared to those treated with isotype control (FIG. 4G). Human DC subsets with antigen cross-presenting capabilities express XCR1, CD141 and Clec9A[31]. XCR1 was increased in neutrophils given 3G8-OVA versus isotype control while CD141 expression was high but comparable between the two groups and the small increase in Clec9A was not statistically significant (FIG. 4H).

Example 2

Figure 9C:
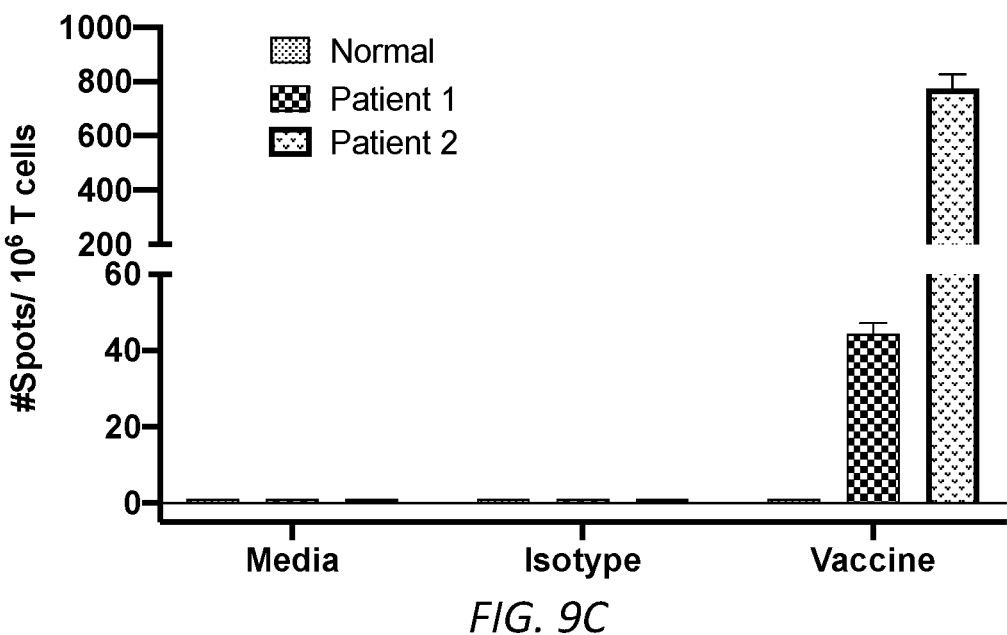
Figure 9D:
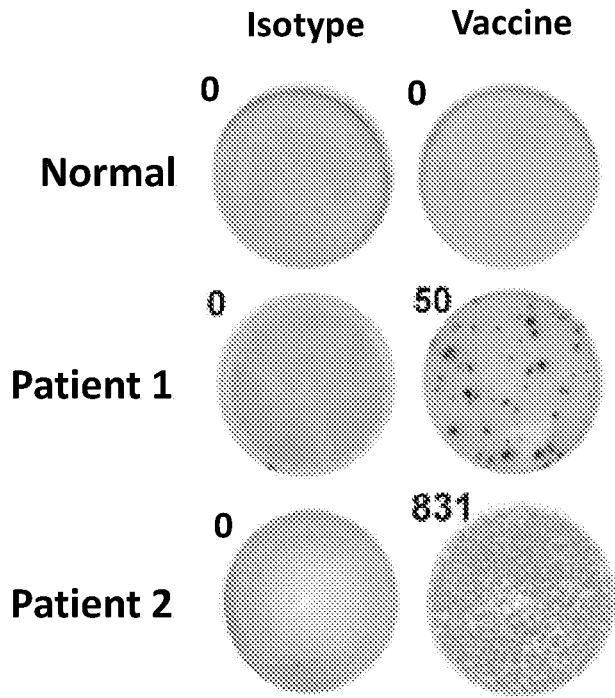

Anti-Fc$\gamma$RIIIB Antibody Alone Converts Neutrophils into Immunogenic Dendritic-Like Cells Malignancies of the innate immune system as in myeloid neoplasms, cancers of the innate immune cells that harbor driver mutations and subsequently express neoantigens. To determine whether neutrophils from these patients can be converted to NDDC that present the antigens to autologous T cells, we treated neutrophils isolated from patients with two different types of myeloid neoplasias with an anti-FcgRIIIB-OVA conjugate or isotype control. Notably, the OVA is irrelevant in this experiment; this conjugate was used as sufficient amount of antibody alone was not immediately available. Neutrophils were isolated from a normal human volunteer (normal), Patient 1 (diagnosed with acute myeloid leukemia) or Patient 2 (diagnosed with myeloid dysplastic syndrome, with driver mutations as determined by a rapid heme panel) and autologous peripheral blood mononuclear cells (PBMC) were frozen down. The isolated neutrophils were incubated with media alone, anti-Fc$\gamma$RIIIB-OVA conjugate (Vaccine) or the isotype control of non-Fc$\gamma$RIIIB binding antibody (Isotype) in the presence of GM-CSF. After 2 days, PBMCs were defrosted, T cells were isolated and autologous T cells were incubated with cognate cultures of neutrophils/NDDCs at a ratio of 4:1. Co-cultures were done in triplicates. After 18 hrs of co-culture, an IFN$\gamma$ ELISPOT assay, which detects IFN generation by activated T cells was performed. Each spot represented an individual cell secreting cytokine. NDDCs were generated in these patients, as assessed by the expression of DC markers outlined in FIG. 1. The NDDCs were incubated with autologous T cells from the same patient, which would be predicted to have T cells reactive against tumor neoantigens albeit in low abundance. Successful antigen presentation by the NDDC to T cells results in T cell activation and subsequent generation of IFN$\gamma$ as assessed in the Elispot assay, which allowed the quantitation of the frequency of individual cells secreting cytokines. We observed significant generation of IFN$\gamma$ in samples with anti-FcgRIIIB-OVA generated nDCs and T cells in the two patients (FIGS. 9C-9D). No IFN$\gamma$ was observed with nDC or T cells alone or with neutrophils incubated with the isotype antibody control. Furthermore, no response was observed in neutrophils from two normal human volunteers treated with anti-FcgRIIIB (FIGS. 9C-9D) as well as two additional patients that were screened.

REFERENCES

1. Lehmann C H, et al. Direct Delivery of Antigens to Dendritic Cells via Antibodies Specific for Endocytic Receptors as a Promising Strategy for Future Therapies. Vaccines (Basel) 4, (2016).
2. Macri C, Dumont C, Johnston A P, Mintern J D. Targeting dendritic cells: a promising strategy to improve vaccine effectiveness. Clin Transl Immunology 5, e66 (2016).
3. Phillips B E, Garciafigueroa Y, Trucco M, Giannoukakis N. Clinical Tolerogenic Dendritic Cells: Exploring Therapeutic Impact on Human Autoimmune Disease. Front Immunol 8, 1279 (2017).
4. Mayadas T N, Cullere X, Lowell C A. The multifaceted functions of neutrophils. Annu Rev Pathol 9, 181-218 (2014).
5. Takashima A, Yao Y. Neutrophil plasticity: acquisition of phenotype and functionality of antigen-presenting cell. J Leukoc Biol 98, 489-496 (2015).
6. Fites J S, et al. An unappreciated role for neutrophil-DC hybrids in immunity to invasive fungal infections. PLoS Pathog 14, e1007073 (2018).
7. Rogers K A, Scinicariello F, Attanasio R. IgG Fc receptor III homologues in nonhuman primate species: genetic characterization and ligand interactions. J Immunol 177, 3848-3856 (2006).
8. Nimmerjahn F, Ravetch J V. Fcgamma receptors as regulators of immune responses. Nat Rev Immunol 8, 34-47 (2008).
9. Gillis C, Gouel-Cheron A, Jonsson F, Bruhns P. Contribution of Human FcgammaRs to Disease with Evidence from Human Polymorphisms and Transgenic Animal Studies. Front Immunol 5, 254 (2014).
10. Unkeless J C, Shen Z, Lin C W, DeBeus E. Function of human Fc gamma RIIA and Fc gamma RIIIB Semin Immunol 7, 37-44 (1995).
11. Bournazos S, Ravetch J V. Fcgamma Receptor Function and the Design of Vaccination Strategies. Immunity 47, 224-233 (2017).
12. Wen Y M, Mu L, Shi Y. Immunoregulatory functions of immune complexes in vaccine and therapy. EMBO Mol Med 8, 1120-1133 (2016).
13. Tsuboi N, Asano K, Lauterbach M, Mayadas T N. Human neutrophil Fcgamma receptors initiate and play specialized nonredundant roles in antibody-mediated inflammatory diseases. Immunity 28, 833-846 (2008).
14. Chen K, et al. Endocytosis of soluble immune complexes leads to their clearance by FcgammaRIIIB but induces neutrophil extracellular traps via FcgammaRIIA in vivo. Blood 120, 4421-4431 (2012).
15. Su K, et al. Expression profile of FcgammaRIIb on leukocytes and its dysregulation in systemic lupus erythematosus. J Immunol 178, 3272-3280 (2007).

16. Alvarez D, Vollmann E H, von Andrian U H. Mechanisms and consequences of dendritic cell migration. Immunity 29, 325-342 (2008).

17. Tsokos G C, Lo M S, Costa Reis P, Sullivan K E. New insights into the immunopathogenesis of systemic lupus erythematosus. Nat Rev Rheumatol 12, 716-730 (2016).

18. Hasenberg A, et al. Catchup: a mouse model for imaging-based tracking and modulation of neutrophil granulocytes. Nat Methods 12, 445-452 (2015).

19. Yamamoto M, et al. Role of adaptor TRIF in the MyD88-independent toll-like receptor signaling pathway. Science 301, 640-643 (2003).

20. Schuurhuis D H, et al. Immune complex-loaded dendritic cells are superior to soluble immune complexes as antitumor vaccine. J Immunol 176, 4573-4580 (2006).

21. Regnault A, et al. Fcgamma receptor-mediated induction of dendritic cell maturation and major histocompatibility complex class I-restricted antigen presentation after immune complex internalization. J Exp Med 189, 371-380 (1999).

22. Palucka K, Banchereau J. Dendritic-cell-based therapeutic cancer vaccines. Immunity 39, 38-48 (2013).

23. Blander J M. Regulation of the Cell Biology of Antigen Cross-Presentation. Annu Rev Immunol 36, 717-753 (2018).

24. Mackensen A, Krause T, Blum U, Uhrmeister P, Mertelsmann R, Lindemann A. Homing of intravenously and intralymphatically injected human dendritic cells generated in vitro from CD34+ hematopoietic progenitor cells. Cancer Immunol Immunother 48, 118-122 (1999).

25. Rafiq K, Bergtold A, Clynes R. Immune complex-mediated antigen presentation induces tumor immunity. J Clin Invest 110, 71-79 (2002).

26. Abbas A K, Murphy K M, Sher A. Functional diversity of helper T lymphocytes. Nature 383, 787-793 (1996).

27. van Elsas A, Hurwitz A A, Allison J P. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 190, 355-366 (1999).

28. Vieira P, Rajewsky K. The half-lives of serum immunoglobulins in adult mice. Eur J Immunol 18, 313-316 (1988).

29. Burleson G R, Burleson F G, Dietert R R. Evaluation of Cell-Mediated Immune Function Using the Cytotoxic T-Lymphocyte Assay. Methods Mol Biol 1803, 199-208 (2018).

30. Yan W L, Shen K Y, Tien C Y, Chen Y A, Liu S J. Recent progress in GM-CSF-based cancer immunotherapy. Immunotherapy 9, 347-360 (2017).

31. Radford K J, Tullett K M, Lahoud M H. Dendritic cells and cancer immunotherapy. Curr Opin Immunol 27, 26-32 (2014).

32. Treffers L W, Hiemstra I H, Kuijpers T W, van den Berg T K, Matlung H L. Neutrophils in cancer. Immunol Rev 273, 312-328 (2016).

33. Cassidy, L. F., Lyles, D. S., and Abramson, J. S. (1988). Synthesis of viral proteins in polymorphonuclear leukocytes infected with influenza A virus. J Clin Microbiol 26, 1267-1270.

34. Hufford, M. M., Richardson, G., Zhou, H., Manicassamy, B., Garcia-Sastre, A., Enelow, R I., and Braciale, T. J. (2012). Influenza-infected neutrophils within the infected lungs act as antigen presenting cells for anti-viral CD8(+) T cells. PLoS One 7, e46581.

35. Larochelle, B., Flamand, L., Gourde, P., Beauchamp, D., and Gosselin, J. (1998). Epstein-Barr virus infects and induces apoptosis in human neutrophils. Blood 92, 291-299.

36. Lindsley, R. C., and Ebert, B. L. (2013). The biology and clinical impact of genetic lesions in myeloid malignancies. Blood 122, 3741-3748.

37. Rosenblatt, J., Stone, R. M., Uhl, L., Neuberg, D., Joyce, R., Levine, J. D., Arnason, J., McMasters, M., Luptakova, K., Jain, S., et al. (2016). Individualized vaccination of AML patients in remission is associated with induction of antileukemia immunity and prolonged remissions. Sci Transl Med 8, 368ra171.

38. Rungelrath, V., Kobayashi, S. D., and DeLeo, F. R. (2020). Neutrophils in innate immunity and systems biology-level approaches. Wiley Interdiscip Rev Syst Biol Med 12, e1458.

39. Saez-Lopez, C., Ngambe-Tourere, E., Rosenzwajg, M., Petit, J. C., Nicolas, J. C., and Gozlan, J. (2005). Immediate-early antigen expression and modulation of apoptosis after in vitro infection of polymorphonuclear leukocytes by human cytomegalovirus. Microbes Infect 7, 1139-1149.

40. Shi, Y., Dincheva-Vogel, L., Ayemoba, C. E., Fung, J. P., Bergamaschi, C., Pavlakis, G. N., Farzaneh, F., and Gaensler, K. M. L. (2018). IL-15/IL-15Ralpha/CD80-expessing AML cell vaccines eradicate minimal residual disease in leukemic mice. Blood Adv 2, 3177-3192.

41. Van Acker, H. H., Versteven, M., Lichtenegger, F. S., Roex, G., Campillo-Davo, D., Lion, E., Subklewe, M., Van Tendeloo, V. F., Berneman, Z. N., and Anguille, S. (2019). Dendritic Cell-Based Immunotherapy of Acute Myeloid Leukemia. J Clin Med 8.

42. Wang, J. P., Bowen, G. N., Padden, C., Cerny, A., Finberg, R. W., Newburger, P. E., and Kurt-Jones, E. A. (2008). Toll-like receptor-mediated activation of neutrophils by influenza A virus. Blood 112, 2028-2034.

43. Webster, J. A., and Pratz, K. W. (2018). Acute myeloid leukemia in the elderly: therapeutic options and choice. Leuk Lymphoma 59, 274-287.

44. Zhao, Y., Lu, M., Lau, L. T., Lu, J., Gao, Z., Liu, J., Yu, A. C., Cao, Q., Ye, J., McNutt, M. A., et al. (2008). Neutrophils may be a vehicle for viral replication and dissemination in human H5N1 avian influenza. Clin Infect Dis 47, 1575-1578.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of generating a population of neutrophil-derived dendritic cells (NDDCs), the method consisting of:

providing a population of neutrophils comprising neutrophils that express one or both of FcγRIIA and/or FcγRIIIB;

contacting the neutrophils in culture with Granulocyte-macrophage colony-stimulating factor (GM-CSF) and an immune complex (IC) comprising an antigen and an antibody, wherein the antibody comprises an antigen binding portion that binds to the antigen and an Fc region that binds to FcγRIIA and/or FcγRIIIB; and maintaining the population of neutrophils in culture in the presence of GM-CSF together with IC for at least two days such that the neutrophils differentiate into NDDCs.

2. The method of claim 1, wherein the antigen comprises a tag portion, and wherein the antibody binds to the tag portion of the antigen.

3. The method of claim 1, wherein the antigen is a tumor antigen.

4. A method of treating a subject who has cancer, the method comprising administering to the subject an effective amount of the cells generated by the method of claim 3.

5. The method of claim 1, wherein the antigen is from a pathogen.

6. A method of treating a subject who is infected with a pathogen, the method comprising administering to the subject an effective amount of the cells generated by the method of claim 5, wherein the antigen is from the pathogen with which the subject is infected.

7. A composition comprising the NDDCs of claim 1, GM-CSF and a conjugate wherein the conjugate comprises an antigen and an antibody comprising an antigen-binding domain that binds to FcγRIII, wherein the conjugate is a fusion protein or chemical conjugate.

8. A method of treating a subject, the method comprising administering to the subject an effective amount of the composition of claim 7.

9. The method of claim 8, wherein the subject has cancer, and the antigen is a tumor antigen.

10. The method of claim 8, wherein the subject has an infection with a pathogen, and the antigen is from the pathogen.

11. A population of neutrophil-derived dendritic cells generated by the method of claim 1.

12. A method of treating a subject, the method comprising administering to the subject an effective amount of the population of claim 11.

13. The method of claim 1, wherein the population of neutrophils was obtained from a subject, and the method further comprises administering the NDDCs to the subject from whom the population of neutrophils was obtained.

14. The method of claim 13, wherein the subject has a myeloid neoplasm or an infection.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Ile Ile Asn Phe Glu Lys Leu
1               5
```